US009683240B2

(12) United States Patent
Bovet et al.

(10) Patent No.: US 9,683,240 B2
(45) Date of Patent: Jun. 20, 2017

(54) MODULATING BETA-DAMASCENONE IN PLANTS

(71) Applicant: PHILIP MORRIS PRODUCTS S.A., Neuchatel (CH)

(72) Inventors: Lucien Bovet, La Chaux de Fonds (CH); Jeremy Catinot, Fribourg (CH); Joanne Schwaar, La Chaux de Fonds (CH)

(73) Assignee: Philip Morris Products S.A., Neuchatel (CH)

( * ) Notice: Subject to any disclaimer, the term of this patent is extended or adjusted under 35 U.S.C. 154(b) by 0 days.

(21) Appl. No.: 14/354,971

(22) PCT Filed: Oct. 30, 2012

(86) PCT No.: PCT/EP2012/071488
§ 371 (c)(1),
(2) Date: Apr. 29, 2014

(87) PCT Pub. No.: WO2013/064499
PCT Pub. Date: May 10, 2013

(65) Prior Publication Data
US 2014/0289901 A1  Sep. 25, 2014

(30) Foreign Application Priority Data

Oct. 31, 2011 (EP) .................................... 11187332
Jan. 25, 2012 (EP) .................................... 12152508

(51) Int. Cl.
*C12N 15/82* (2006.01)
*C07K 14/415* (2006.01)
*C12N 9/90* (2006.01)

(52) U.S. Cl.
CPC .......... *C12N 15/825* (2013.01); *C07K 14/415* (2013.01); *C12N 9/90* (2013.01); *C12N 15/8243* (2013.01); *C12N 15/8271* (2013.01)

(58) Field of Classification Search
None
See application file for complete search history.

(56) References Cited

U.S. PATENT DOCUMENTS

| 3,940,499 A | 2/1976 | Pittet |
| 2001/0051713 A1 | 12/2001 | An |
| 2006/0265784 A1 | 11/2006 | Hauptman |

FOREIGN PATENT DOCUMENTS

| CN | 101624556 | 1/2010 |
| EP | 1818536 A2 | 8/2007 |
| EP | 1 867 723 | 12/2007 |
| EP | 2290224 A2 | 3/2011 |
| KZ | 8528 B | 2/2000 |
| RU | 2245921 | 2/2005 |
| SU | 988175 | 1/1983 |
| WO | WO 00/08920 | 2/2000 |

OTHER PUBLICATIONS

North, H.M. et al. The Plant Journal (2007) vol. 50, pp. 810-824.*
Guo et al. 2004, PNAS 101(25) pp. 9205-9210.*
Al-Babili, S. et al. (2000) FEBS Letters, vol. 485, pp. 168-172.*
Office Action issued in Singapore for Application No. 11201401858Y dated Jan. 30, 2015 (12 pages).
Office Action issued in New Zealand for Application No. 624229 dated Feb. 26, 2015 (2 pages).
International Preliminary Report on Patentability for PCT/EP2012/071488 dated May 14, 2014 (10 pages).
PCT International Search Report and Written Opinion for International Application No. PCT/EP2012/071488 dated Mar. 14, 2013 (14 pages).
Walter, Michael et al., "Carotenoids and Their Cleavage Products: Biosynthesis and Functions", *Natural Product Reports Apr 2011 LNKD-PUBMED:21321752*, vol. 28, No. 4, Apr. 2011, pp. 663-692.
Bouvier et al., "Identification of Neoxanthin Synthase as a Carotenoid Cyclase Paralog", *European Journal of Biochemistry*, vol. 267, No. 21, Nov. 2000, pp. 6346-6352.
North, Helen et al., "The Arabidopsis ABA-Deficient Mutant aba4 Demonstrates that the Major Route for Stress-Induced ABA Accumulation is Via Neoxanthin Isomers", *Plant Journal*, vol. 50, No. 5, Jun. 2007, pp. 810-824.
Walter, Michael et al., "Carotenoids and Their Cleavage Products: Biosynthesis and Functions", *Natural Product Reports Apr. 2011 LNKD-PUBMED:21321752*, vol. 28, No. 4, Apr. 2011, pp. 663-692.
Database EMBL [Online], Apr. 15, 2006, XP02671508, Database Accession No. EB426201.
Extended European Search Report for Application No. 12833002.4 dated Nov. 26, 2015 (6 pages).
Examination Report issued in Australia for Application No. 2012331235 dated Jun. 2, 2016 (7 pages).
Examination Report issued in Japan for Application No. 2014-539311dated Aug. 23, 2016 (4 pages). English translation only.
Office Action issued in Kazakhstan for Application No. 2014/1602.1 dated Feb. 24, 2016 (8 pages). English translation included.

(Continued)

*Primary Examiner* — Russell Kallis
(74) *Attorney, Agent, or Firm* — Mueting, Raasch & Gebhardt, P.A.

(57) ABSTRACT

A mutant, non-naturally occurring or transgenic plant cell comprising: (i) a polynucleotide comprising, consisting or consisting essentially of a sequence encoding a neoxanthin synthase and having at least 60% sequence identity to SEQ ID NO:1 or SEQ ID No. 6; (ii) a polypeptide encoded by the polynucleotide set forth in (i); (iii) a polypeptide having at least 66% sequence identity to SEQ ID NO:2 or at least 60% sequence identity to SEQ ID No. 7; or (iv) a construct, vector or expression vector comprising the isolated polynucleotide set forth in (i), and wherein the expression or activity of the neoxanthin synthase is modulated as compared to a control or wild type plant.

31 Claims, 8 Drawing Sheets

(56) References Cited

OTHER PUBLICATIONS

Office Action issued in Israel for Application No. 232220 dated Jul. 17, 2016 (4 pages). English translation included.
Office Action issued in China for Application No. 201280064294.3 dated Mar. 31, 2016 (4 pages). English translation included.
Examination Report issued in Russia for Application No. 2014121656 dated Aug. 1, 2016 (12 pages). English translation included.
Papula, Andrew A., "Genetic Analysis of Protein Stability and Function," *Anna. Rev. Genet.*, 1989, vol. 23, pp. 289-310.
Third Office Action issued in China for Application No. 2016121501618760 dated Dec. 20, 2016 (4 pages). English translation included.

* cited by examiner

FIGURE 2

A
atgtcactttcttttaattcttcttgtttttgtcccctcttaataagtcaagtatggacttctcttcttcttgcttctgctactc
tcacatctcactcaagatgaactgcagggcacctgccttgatgtccaggagaaccagcctacctcttatactttctagaaaaga
attctgacattgtaaatcaacaagtagtggaattcggaaccaagtttagaagtggagcgaatttcctggaggatcaagagtcatt
attcaacttaatcttcaaacaactcttgctcaaagaaaaagctccagggtgactgcttgtttgccaagttctgaaattgcttctac
tgttttcacactgggaacagcagcagttcttccgttttatactctcatggttgtggctcctaaaactgaacttaccagaaaagtga
tgaaaagcagcatacccaatattggctttggacttctgtacacatatctagtatacctctcttggacaccagatacagttcggctg
atgtttgctagtaaatactggcttcggagctgccggcataactaagatgttctccasgcagatgacattagcttctgcatggat
tcacttgttggctgtagatcttttgctgcaaggcaggtttatcatgatggatgcaaaatgatattgaaaccgccattctgtgt
ctctgtgcttgctgttttgccccgtcggaattgttactcacttcatcaccaaagctctagccagtagcccagaaaagagacagcat
aggactcattaa   (SEQ ID NO: 1)

B
MSLSPNSSCFCSPLNKSSMDFSSSCFCYSRISLMMCRAPALMSRRNQPTSYTFLEKNSDIVNQQVVEFGTKFRSGANFLGGSRVI
IQLNLQTTLAQRKSSRVTACLPSSEIASTVFTLGTAAVLPFYTLMVVAFKTELTRKVMKSSIPNIGPGLLYTLVYLSWTPDTVRL
MFASKYWLPELPGITKMFSNEMTLASAWIHLLAVDLFAARQVYHDGLQNDIETRHSVSLCLLFCPVGIVTHFTTKALASSPEKRQH
RT     (Amino acids 1-260 of SEQ ID NO: 2)

C
NtABA4-F     caccatgtcactttcttttaattcttcttgt   (SEQ ID NO: 3)
NtABA4-R     ttaatgagtcctatgctgtctcttc   (SEQ ID NO. 5)

A
ATGGAAACTCTTCTCAAACCTTTTCCATCTCCTTTACTTTTCACTCCTACACCTCACAGGTCTATTTTTCAACTGAAT
TCTACTTTTCTGAATCCAACCACCCAGAACTTTTCAAGAAAAGTTCATCGCAGAAACAAAAGTAGTAGTAACAAATTT
TGTAGCTTTCTTGACTTAGCACCCACATCAAAACCAGAGTCTTTAGATGTTGACATCTCATGGGTTGATCCTAATTCG
GGCCGGGCTCTATTCGACGTGATCATCATCGGAGCTGGTCCTGCGGGCCTCCGGCTAGCTGAGCAAGTATCAAGATAT
GGTATTAAGGTATGTTGTGTTGACCCTTCACCACTTTCCATGTGGCCAAATAATTATGGTGTTTGGGTTGATGAGTTT
GAGAAGTTAGGATTGGAACATTGTTTAGATCATAAGTGGCCTATGACTTGTGTTCATATAAATGATAACAAGACTAAG
TATTTGGGAAGACCATATGGTAGAGTCAGTAGAAAAAGTTGAAGTTGAAATTGTTGAATAGTTGTGTTGATAATGGA
GGGAAGTTTTATAAAGCCAAGGTTTGGAAAGTGGAGCATGAAGAATTTGAGTCTCAGTTGTTTGTGATGATGGTAGG
AAGATAAGGGGTAGTTTGATTGTAGATGCAAGTGGTTTTGCTAGTCCTTTTATAGAATATCACAAGCCAAGAAACCAT
GGTTATCAAATAGCTCATGGGATTTTAGCACAAGTGGATAATCATCCATTTGATTTGGATAAAATGGTGCTTATGGAT
TGGAGGGATTCTCATCTGGGAAATGAGCCATATTTGAGGGTGAACAATACTAAAGAACCAACATTCTTGTATGTGATG
CCATTTGATAGGAATTTGGTATTCTTGGAAGAGACTTCTTTGGTGAGTCGGCCTGTGCTATCGTATAGGGAAGTGAAA
AATAGGATGGTGGCAAGGTTAAGGCATTTGGGGATCAAAGTGACAAGTGTTATTGAGGATGAGAAATGTGTGATCCCC
ATGGGACGACCACTTCCGCGGATCCCTCAAAATGTTATGGCAATTGGTGGAAATTCAGGGATAGTTCATCCATCGACA
GGGTACATGGTGGCTCGGAGCATGGCATTGGCACCAGTTTTGGCTGAGGCCATTGCTGAGAGCCTCGGCACAACCAGA
ATGATAAGAGGATCTCCACTTTACCATAAAGTTTGGAATGGTTTGTGGCCTCTAGAGAGAAGAAGTGTGAGAGAATGT
TACTCTTTTGGGATGGAGACTTTGTTGAAGCTTGATTTGAAAGGGACTAGGAGATTGTTTGATGCTTTCTTTGATCTT
GATCCCAAATACTGGCAAGGGTTCCTTTCCTCAAGGTTGTCTGTCAAAGAACTTGCTATGCTTAGCTTGTACCTTTTT
GGGCATGCCTCAAATTTGGCTAGGTTGGATATTGTTACAAAATGCCCGGTGCCCTTGGTTAAAATGATGGAAATCTAG
(SEQ ID NO: 8)

B
METLLKPFPSPLLFTPTPHRSIFQLNSTFLNPTTQNFSRKVHRRNKSSSNKFCSFLDLAPTSKPESLDVDISWVDPNS
GRALFDVIIGAGPAGLRLAEQVSRYGIKVCCVDPSPLSMWFNNYGVWVDEFEKLGLEDCLDHKWPMTCVHINDNKTK
YLGRPYGRVSRKKLKLRLLNSCVDNGGKFYKAKVWKVEHEEFESSVVCDDGRKIRGSLIVDASGPASPFIEYDKPRNH
GYQIAHGILAQVDNHPFDLDKMVLMDWRDSHLGNEPYLRVNNTKEPTFLYVMPFDRNLVFLEETSLVSRPVLSYREVK
NRMVARLRHLGIKVTSVIEDEKCVIPMGGPLPRIPQNVMAIGGNSGIVHPSTGYMVARSMALAPVLAEAIAESLGTTR
MIRGSPLYHKVWNGLWPLERRSVRECYSFGMETLLKLDLKGTRRLFDAFFDLDPKYWQGFLSSRLSVKELAMLSLYLF
GHASNLARLDIVTKCPVPLVKMMEI SEQ ID NO: 9

C
NeSY-F    CACCATGGAAACTCTTCTCAAACCTTTTC (SEQ ID NO: 10)
NeSY-R    CTAGATTTCCATCATTTTAACCAAG (SEQ ID NO: 12)

ACACAAGCTTGGCTTTATTCGGAGGCAAACTATTCGCTCTTGGTGAATCTGATTTACCGTATGCAGTAAAATTAGCCCCAGATGGT
GATATTATTACCCTCGGCCGTTACGATTTCGACGGAAAACTTTTCATGAGCATGACGGCACATCCCAAAATTGACCCAGATACTAA
CGAGGCTTTTGCTTTCCGTTACGGTCCAATGCCTCCTTTTTTAACTTACTTTAGAATCGAACCAAATGGTACAAAAACACCAGACG
TGCCAATATTTCTATGACACGTCCGTCATTTCTTCATGACTTTGCAATTACAAATAAATTGCGATATTCTCGGACATACAAATA
GGAATGAACCCACTTGAGTTCATCACCGGTGGTTCACCGGTGAGTTCAGACTCGGGAAAATC (SEQ ID NO: 13)

B
NtCED2_RNAi-F:   caccacacaagcttggctttattcg (SEQ ID NO: 14)
NtCED2_RNAi-R:   gattttcccgagtctgaact (SEQ ID NO: 16)

MODULATING BETA-DAMASCENONE IN PLANTS

This application is a U.S. National Stage Application of International Application No. PCT/ep2012/071488, filed Oct. 30, 2012, which was published in English on May 10, 2013, International Patent Publication WO 2013/064499 A1. International Application No. PCT/EP2012/071488 claims priority to European Application No. 11187332.9, filed Oct. 31, 2011 and European Application No. 12152508.3, filed Jan. 25, 2012.

FIELD OF THE INVENTION

The present invention discloses the polynucleotide sequences of neoxanthin synthase, lycopene beta cyclase and 9-cis-epoxycarotenoid dioxygenase from *Nicotiana tabacum* and variants, homologues and fragments thereof. In particular, there is described the modification of the expression of neoxanthin synthase or the activity of the protein encoded thereby to modulate the amount of beta-damascenone that is detectable in the aerosol of heated tobacco resulting in new flavour profiles in tobacco.

BACKGROUND OF THE INVENTION

Beta-damascenone is an aroma factor in the distillation aerosol of cured tobacco. It has a typical fruity and cooked apple flavor, which can also be found naturally in *Rosa damascena* Mill (the Damask rose), thereby indicating the existence of an enzymatic pathway leading to its synthesis in some plants. The flowers of *Rosa damascena* are renowned for their fine fragrance, and are commercially harvested for rose oil used in perfumery and to make rose water. The flower petals are also sometimes used directly to flavor food or drink and are considered safe for human consumption.

Carotenoids are potential precursors for beta-damascenone production. Thermal oxidation of neoxanthin leads to the formation of beta-damascenone. Neoxanthin is an oxygenated carotenoid derivative belonging to the class of xanthophylls and consists of eight isoprenoid units. In senescent and cured leaves, free neoxanthin is not present or is only detected at very low levels. Within the plant carotenoid pathway which occurs in the plastids—such as chloroplasts—enzymes known to form neoxanthin belong to the class of neoxanthin synthases. Neoxanthin synthase catalyses the formation of neoxanthin from violaxanthin and is encoded by the ABA4 polynucleotide. Lycopene beta cyclase also catalyses the formation of neoxanthin from violaxanthin and is encoded by the NeSy polynucleotide. 9-cis-epoxycarotenoid dioxygenase(s) catalyses the cleavage of cis-neoxanthin in $C_{25}$-allenic-apo-aldehyde and xanothin and is encoded by the NCED2 polynucleotide.

There is a continuing need in the art for plant materials—such as tobacco—with modified flavour profiles. It is an object of the present invention to satisfy this need.

SUMMARY OF THE INVENTION

The corresponding ABA4, NeSy and NCED2 genes have been cloned and sequenced from *Nicotiana tabacum* and the effect of the modulated expression of these genes has been investigated. The enzymes encoded by the NeSy and NCED2 polynucleotides are believed to be components of the carotenoid biosynthetic pathway and upregulating the expression of the NeSy polynucleotide and downregulating the expression of the NCED2 polynucleotide in a plant was found to increase carotenoid content. However, altered production of beta-damascenone was not detected. Surprisingly, the inventors discovered that increasing the expression of the ABA4 polynucleotide not only increased the carotenoid content but also significantly increased the beta-damascenone content in aerosol formed after heating cured tobacco prepared from a tobacco plant. This finding was even more surprising since the NeSy polynucleotide encodes an enzyme which acts at the same point in the carotenoid biosynthetic pathway as the ABA4 polynucleotide but the NeSy polynucleotide was found to have no significant effect on beta-damascenone levels. Without wishing to be bound by any particular theory, this finding suggests that a neoxanthin synthase encoded by the ABA4 polynucleotide plays a central role in beta-damascenone synthesis in *Nicotiana tabacum*. This allows plants to be produced in which the levels of beta-damascenone are modulated and thus have altered flavour profiles. Plants can be engineered in which the carotenoid content thereof is modulated. Such plants may have nutritional benefits to the consumer. In addition, modulating the carotenoid content of a plant may be used to generate plants that are resistant to herbicides that inhibit carotenoid biosynthesis, which may extend the use of carotenoid inhibitors as herbicides for crops that are currently sensitive to these compounds. Advantageously, these changes do not substantially alter the visual appearance of the plants which is an important criterion for acceptance by industry and for maximising plant yields and the like.

ASPECTS AND EMBODIMENTS OF THE INVENTION

Aspects and embodiments of the present invention are set forth in the accompanying claims.

In one aspect there is provided an isolated polynucleotide comprising, consisting or consisting essentially of a sequence encoding neoxanthin synthase and having at least 60% sequence identity to SEQ ID NO:1 or SEQ ID No. 6.

In another aspect there is provided an isolated polypeptide encoded by the polynucleotide.

In another aspect there is provided an isolated polypeptide having at least 66% sequence identity to SEQ ID NO:2 or at least 60% sequence identity to SEQ ID No. 7.

In another aspect there is provided a construct, vector or expression vector comprising the isolated polynucleotide(s).

In another aspect there is provided a mutant, non-naturally occurring or transgenic plant cell comprising the isolated polynucleotide(s), the polypeptide or the construct, vector or expression vector described herein and wherein the expression or activity of neoxanthin synthase is modulated as compared to a control or wild type plant.

In one embodiment, the mutant, non-naturally occurring or transgenic plant comprises the plant cell.

In another aspect there is provided a method for modulating the carotenoid content of a plant, comprising the steps of: (i) modulating the expression or activity of a neoxanthin synthase in the plant, preferably, wherein the neoxanthin synthase comprises the polynucleotide sequence or the polypeptide sequence set forth herein; (ii) measuring the carotenoid content in at least a part of the mutant, non-naturally occurring or transgenic plant obtained in step (i); and (iii) identifying a mutant, non-naturally occurring or transgenic plant in which the carotenoid content therein has changed in comparison to a control plant in which the expression or activity of neoxanthin synthase has not been modulated.

In one embodiment, the expression or activity of lycopene beta cyclase or 9-cis-epoxycarotenoid dioxygenase or a combination thereof is also modulated in the plant.

In one embodiment, the lycopene beta cyclase comprises the polynucleotide sequence set forth in SEQ ID NO:8 or has at least 60% sequence identity thereto or the polypeptide sequence comprises the set forth in SEQ ID NO:9 or has at least 60% sequence identity thereto and wherein the 9-cis-epoxycarotenoid dioxygenase comprises the polynucleotide sequence set forth in SEQ ID NO:13 or has at least 60% sequence identity thereto.

In another aspect there is provided a method for modulating the beta-damascenone content of a plant, comprising the steps of: (i) modulating the expression or activity of a neoxanthin synthase in the plant, preferably, wherein the neoxanthin synthase comprises the polynucleotide sequence or the polypeptide sequence described herein; (ii) measuring the beta-damascenone content in at least a part of the mutant, non-naturally occurring or transgenic plant obtained in step (i); and (iii) identifying a mutant, non-naturally occurring or transgenic plant in which the beta-damascenone content therein has changed in comparison to a control plant in which the expression or activity of neoxanthin synthase has not been modulated.

In another aspect there is provided a mutant, non-naturally occurring or transgenic plant or plant material derived or derivable therefrom that is obtained or obtainable by the method(s) described herein.

In another aspect there is provided a mutant, non-naturally occurring or transgenic plant, wherein expression of a neoxanthin synthase or the activity of the protein encoded thereby has been increased; wherein the green leaf lutein content or the beta-carotene content or the combined lutein and beta-carotene content of the plant is higher than a control plant in which the expression or the activity of neoxanthin synthase has not been increased; and wherein the beta-damascenone content in aerosol of cured plant material is at least 10% higher than the aerosol from the control plant, preferably, wherein: (i) the green leaf lutein content of the plant is at least about 18 mg/100 g; (ii) wherein the beta-carotene content of the plant is at least about 12 mg/100 g; and (iii) wherein the beta-damascenone content in aerosol upon heating leaf biomass from the plant is at least about 1 ng/mg.

In another aspect there is provided plant material including biomass, seed or leaves from the plant described herein.

In another aspect there is provided a tobacco product comprising the plant cells, at least a part of the plant or plant material described herein.

In another aspect there is provided a method for producing beta-damascenone comprising the steps of: (a) providing at least part of a plant, plant material or the tobacco product as described herein; and (b) providing heat thereto to produce an aerosol comprising beta-damascenone.

Further aspects include the following.

A chimeric gene comprising one or more of the isolated polynucleotides described herein operably linked to one or more regulatory sequences.

A polynucleotide construct comprising one or more of the isolated polynucleotides described herein and comprising, consisting or consisting essentially of at least 15-30 nucleotides, 30-50 nucleotides, 50-100 nucleotides, 100-150 nucleotides, 150-200 nucleotides, 200-300 nucleotides, 300-400 nucleotides, 400-500 nucleotides, 500-600 nucleotides or 600-700 nucleotides.

A consumable product incorporating or utilising plant material, biomass, seed or leaves as described herein.

A cell line comprising the isolated polynucleotide, the chimeric gene, the polynucleotide construct, the double-stranded RNA, the conjugate or the expression vector and the like as described herein.

A method for modulating the expression of one or more the polynucleotides described herein or the activity of one or more the polypeptides encoded thereby in a cell, said method comprising administering the chimeric gene, the polynucleotide construct, the double-stranded RNA, the conjugate or the expression vector as described herein.

A method for detecting, isolating, amplifying or analysing one or more the polynucleotides described herein, the method comprising the step of providing a sample comprising a polynucleotide and hybridising said polynucleotide to a polynucleotide molecule comprising a nucleotide sequence of at least 10 contiguous nucleotides from the isolated nucleotide sequence.

A method for modulating the carotenoid content and the beta-damasceonone content or the carotenoid content or the beta-damasceonone content in at least a part of a plant as compared to a control plant comprising the use of an agent that modulates the expression of one or more the polynucleotides described herein or the activity of the protein encoded thereby.

Use of agent that modulates the expression of one or more the polynucleotides described herein or the activity of the protein encoded thereby for modulating the carotenoid content and the beta-damasceonone content or the carotenoid content or the beta-damasceonone content in at least a part of a plant as compared to a control plant.

In one embodiment, the agent is or is derived from, a chimeric polynucleotide gene, a polynucleotide construct comprising one or more the polynucleotides, an antisense RNA, a double-stranded RNA, a cDNA, a conjugate comprising one or more of the polynucleotides or at least one non-nucleotide or non-polynucleotide moiety covalently attached thereto, a ribozyme, a mutagen, a zinc finger, a small molecule or a meganuclease.

In another embodiment, the polynucleotide fragment(s) encodes an antisense nucleic acid, a ribozyme, an RNA that effects spliceosome-mediated trans-splicing, an interfering RNA, a guide RNA, or other non-translated RNA and the like. In another embodiment, the polynucleotide fragment(s) encodes an interfering RNA.

BRIEF DESCRIPTION OF THE DRAWINGS

FIG. 2. (A) NtABA4 cDNA sequence amplified from K326 used to engineer 35S::NtABA4 plants; (B) NtABA4 translated sequence; (C) Forward (F) and reverse (R) primers used to amplify the NtABA4 sequence. The 5' cacc sequence in the F primer is required for cloning into pENTER Gateway vectors.

FIG. 4. (A) NtNeSy cDNA sequence amplified from K326 used to engineer 35S::NtNeSy plants; (8) NtNeSy translated sequence; (C) Forward (F) and reverse (R) primers used to amplify the NtNeSy sequence. The 5' cacc sequence in the F primer is required for cloning into pENTER Gateway vectors.

FIG. 5. (A) NtNCED2 partial cDNA sequence used to engineer NtNCED2-interfering RNA plants. (B) Forward (F) and reverse (R) primers used to amplify the NtNCED2 partial sequence. The 5' cacc sequence in the F primer is required for cloning into pENTER Gateway vectors.

DEFINITIONS

Figure 1:
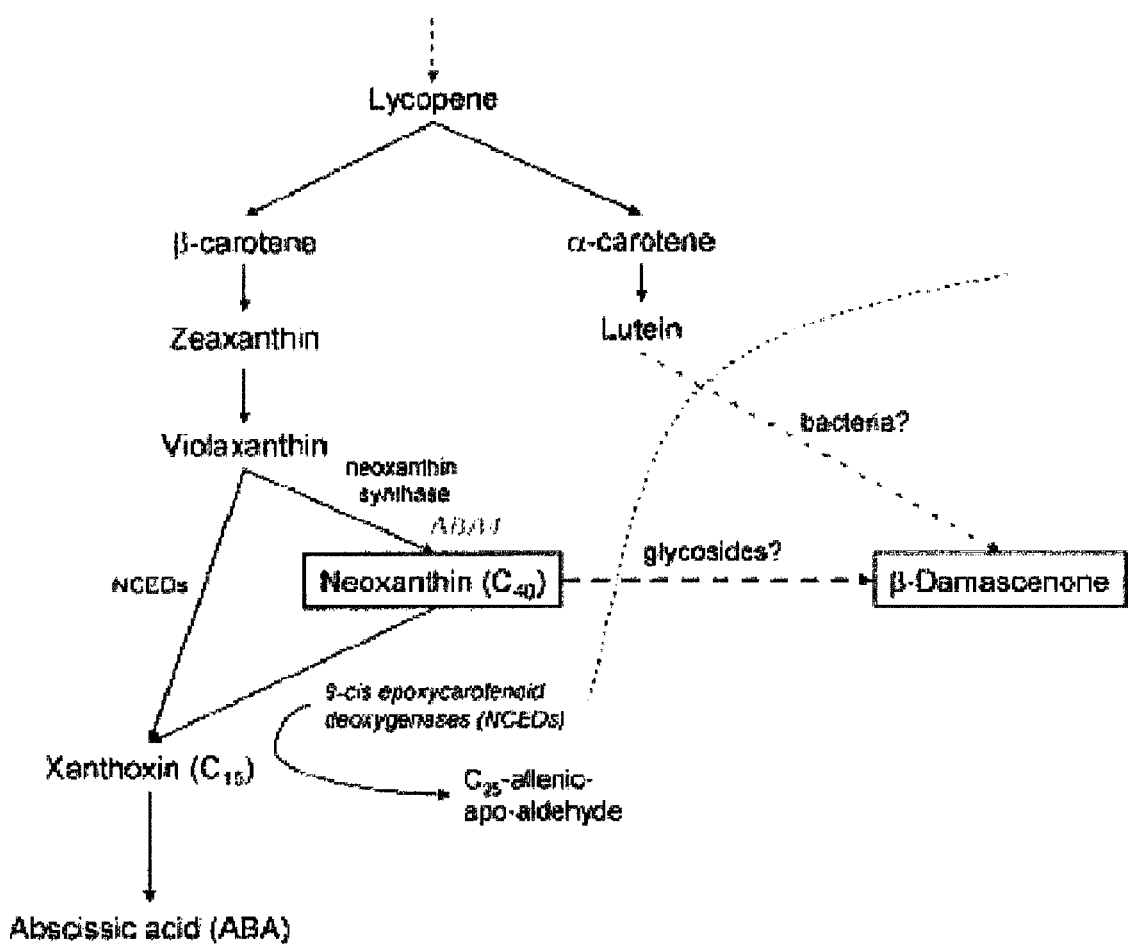
FIG. 1. Simplified version of the carotenoid pathway in plants. Neoxanthin and lutein are precursor candidates contributing to the formation of beta-damascenone in leaves. Additional, but so far uncharacterized steps include glycoside formation and bacterial degradation during curing, respectively.

The technical terms and expressions used within the scope of this application are generally to be given the meaning commonly applied to them in the pertinent art of plant and molecular biology. All of the following term definitions apply to the complete content of this application. The word "comprising" does not exclude other elements or steps, and the indefinite article "a" or "an" does not exclude a plurality. A single step may fulfil the functions of several features recited in the claims. The terms "about", "essentially" and "approximately" in the context of a given numerate value or range refers to a value or range that is within 20%, within 10%, or within 5%, 4%, 3%, 2% or 1% of the given value or range.

The term "isolated" refers to any entity that is taken from its natural milieu, but the term does not connote any degree of purification.

A "vector" refers to a nucleic acid vehicle that comprises a combination of nucleic acid components for enabling the transport of nucleic acid, nucleic acid constructs and nucleic acid conjugates and the like. Suitable vectors include episomes capable of extra-chromosomal replication such as circular, double-stranded nucleic acid plasmids; linearized double-stranded nucleic acid plasmids; and other vectors of any origin.

An "expression vector" is a nucleic acid vehicle that comprises a combination of nucleic acid components for enabling the expression of nucleic acid—such as the ABA4 polynucleotide, nucleic acid constructs and nucleic acid conjugates and the like. Suitable expression vectors include episomes capable of extra-chromosomal replication such as circular, double-stranded nucleic acid plasmids; linearized double-stranded nucleic acid plasmids; and other functionally equivalent expression vectors of any origin. An expression vector comprises at least a promoter positioned upstream and operably-linked to a nucleic acid, nucleic acid constructs or nucleic acid conjugate, as defined below.

The term "construct" refers to a double-stranded, recombinant nucleic acid fragment comprising one or more polynucleotides. The construct comprises a "template strand" base-paired with a complementary "sense or coding strand." A given construct can be inserted into a vector in two possible orientations, either in the same (or sense) orientation or in the reverse (or anti-sense) orientation with respect to the orientation of a promoter positioned within a vector—such as an expression vector.

A "promoter" refers to a nucleic acid element/sequence, typically positioned upstream and operably-linked to a double-stranded DNA fragment. Promoters can be derived entirely from regions proximate to a native gene of interest, or can be composed of different elements derived from different native promoters or synthetic DNA segments.

The terms "homology, identity or similarity" refer to the degree of sequence similarity between two polypeptides or between two nucleic acid molecules compared by sequence alignment. The degree of homology between two discrete nucleic acid sequences being compared is a function of the number of identical, or matching, nucleotides at comparable positions. The percent identity may be determined by visual inspection and mathematical calculation. Alternatively, the percent identity of two nucleic acid sequences may be determined by comparing sequence information using a computer program such as—ClustalW, BLAST, FASTA or Smith-Waterman.

The term "plant" refers to any plant at any stage of its life cycle or development, and its progenies. In one embodiment, the plant is a "tobacco plant", which refers to a plant belonging to the genus *Nicotiana*. Preferred species of tobacco plant are described herein.

A "plant cell" refers to a structural and physiological unit of a plant. The plant cell may be in the form of a protoplast without a cell wall, an isolated single cell or a cultured cell, or as a part of higher organized unit such as but not limited to, plant tissue, a plant organ, or a whole plant.

The term "plant material" refers to any solid, liquid or gaseous composition, or a combination thereof, obtainable from a plant, including biomass, leaves, stems, roots, flowers or flower parts, fruits, pollen, egg cells, zygotes, seeds, cuttings, secretions, extracts, cell or tissue cultures, or any other parts or products of a plant. In one embodiment, the plant material comprises or consists of biomass, seed or leaves. In another embodiment, the plant material comprises or consists of leaves.

The term "variety" refers to a population of plants that share constant characteristics which separate them from other plants of the same species. While possessing one or more distinctive traits, a variety is further characterized by a very small overall variation between individuals within that variety. A variety is often sold commercially.

The term "line" or "breeding line" as used herein denotes a group of plants that are used during plant breeding. A line is distinguishable from a variety as it displays little variation between individuals for one or more traits of interest, although there may be some variation between individuals for other traits.

The term "modulating" may refer to reducing, inhibiting, increasing or otherwise affecting the expression or activity of a polypeptide. The term may also refer to reducing, inhibiting, increasing or otherwise affecting the activity of a gene encoding a polypeptide which can include, but is not limited to, modulating transcriptional activity.

The term "reduce" or "reduced" as used herein, refers to a reduction of from about 10% to about 99%, or a reduction of at least 10%, at least 20%, at least 25%, at least 30%, at least 40%, at least 50%, at least 60%, at least 70%, at least 75%, at least 80%, at least 90%, at least 95%, at least 98%, at least 99%, or at least 100% or more of a quantity or an activity, such as but not limited to polypeptide activity, transcriptional activity and protein expression.

The term "inhibit" or "inhibited" as used herein, refers to a reduction of from about 98% to about 100%, or a reduction of at least 98%, at least 99%, but particularly of 100%, of a quantity or an activity, such as but not limited to polypeptide activity, transcriptional activity and protein expression.

The term "increase" or "increased" as used herein, refers to an increase of from about 5% to about 99%, or an increase of at least 5%, at least 10%, at least 20%, at least 25%, at least 30%, at least 40%, at least 50%, at least 60%, at least 70%, at least 75%, at least 80%, at least 90%, at least 95%, at least 98%, at least 99%, or at least 100% or more of a quantity or an activity, such as but not limited to polypeptide activity, transcriptional activity and protein expression.

The term "control" in the context of a control plant means a plant or plant cell in which the expression or activity of an enzyme has not been modified (for example, increased or reduced) and so it can provide a comparison with a plant in which the expression or activity of the enzyme has been modified. The control plant may comprise an empty vector. The control plant may correspond to a wild-type plant.

DETAILED DESCRIPTION

In one embodiment, there is provided an isolated polynucleotide comprising, consisting or consisting essentially of a polynucleotide sequence having at least 60% sequence identity to any of the sequences described herein, including any of polynucleotides shown in the sequence listing. Suitably, the isolated polynucleotide comprises, consists or consists essentially of a sequence having at least 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99% or 100% sequence identity thereto.

In another embodiment, there is provided an isolated polynucleotide comprising, consisting or consisting essentially of a polynucleotide sequence encoding a neoxanthin synthase and having at least 60% sequence identity to SEQ ID No.1. Suitably, the isolated polynucleotide comprises, consists or consist essentially of a sequence having at least about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99% or 100% sequence identity to SEQ ID No. 1.

In another embodiment, there is provided an isolated polynucleotide comprising, consisting or consisting essentially of a polynucleotide sequence encoding a lycopene beta cyclase and having at least 60% sequence identity to SEQ ID No.8. Suitably, the isolated polynucleotide comprises, consists or consist essentially of a sequence having at least about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99% or 100% sequence identity to SEQ ID No. 8.

In another embodiment, there is provided an isolated polynucleotide comprising, consisting or consisting essentially of a polynucleotide sequence encoding a 9-cis-epoxy-carotenoid dioxygenase and having at least 60% sequence identity to SEQ ID No.13. Suitably, the isolated polynucleotide comprises, consists or consist essentially of a sequence having at least about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99% or 100% sequence identity to SEQ ID No. 13.

As used herein, the term "polynucleotide" refers to a polymer of nucleotides, which may be unmodified or modified deoxyribonucleic acid (DNA) or ribonucleic acid (RNA). Accordingly, a polynucleotide can be, without limitation, a genomic DNA, complementary DNA (cDNA), mRNA, or antisense RNA or a fragment(s) thereof. Moreover, a polynucleotide can be single-stranded or double-stranded DNA, DNA that is a mixture of single-stranded and double-stranded regions, a hybrid molecule comprising DNA and RNA, or a hybrid molecule with a mixture of single-stranded and double-stranded regions or a fragment(s) thereof. In addition, the polynucleotide can be composed of triple-stranded regions comprising DNA, RNA, or both or a fragment(s) thereof. A polynucleotide can contain one or more modified bases, such as phosphothioates, and can be a peptide nucleic acid. Generally, polynucleotides can be assembled from isolated or cloned fragments of cDNA, genomic DNA, oligonucleotides, or individual nucleotides, or a combination of the foregoing. Although the polynucleotide sequences described herein are shown as DNA sequences, the sequences include their corresponding RNA sequences, and their complementary (for example, completely complementary) DNA or RNA sequences, including the reverse complements thereof.

The term "NtABA4 polynucleotide", relates to polynucleotides encoding neoxanthin synthase from *Nicotiana tabacum* and includes other polynucleotides comprising, consisting or consisting essentially of polynucleotides with substantial homology (that is, sequence similarity) or substantial identity to SEQ ID NO:1 or SEQ ID NO:6; polynucleotide variants that have at least about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98% or 99% sequence identity to the sequence of SEQ ID NO:1 or SEQ ID NO: 6; fragments of the NtABA4 polynucleotide including fragments of SEQ ID NO:1 or SEQ ID NO:6; fragments of SEQ ID NO:1 or SEQ ID NO:6 with substantial homology (that is, sequence similarity) or substantial identity thereto that have at least about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99% or 100% sequence identity to the corresponding fragments of SEQ ID NO:1 or SEQ ID NO:6. The NtABA4 polynucleotide also includes sequences comprising a sufficient or substantial degree of identity or similarity to SEQ ID NO:1 or SEQ ID NO: 6 to encode a polypeptide that functions as a neoxanthin synthase. In one embodiment, the term "NtABA4 polynucleotide" refers to a polymer of nucleotides which comprises, consists or consists essentially of a polynucleotide designated herein as SEQ ID NO:1 or SEQ ID NO: 6.

The term "NtNeSY polynucleotide", relates to polynucleotides encoding lycopene beta cyclase from *Nicotiana tabacum* and includes other polynucleotides comprising, consisting or consisting essentially of polynucleotides with substantial homology (that is, sequence similarity) or substantial identity to SEQ ID NO:8; fragments of the NtNeSy polynucleotide including fragments of SEQ ID NO:8; polynucleotide variants that have at least about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96% 97%, 98% or 99% sequence identity to the sequence of SEQ ID NO:8; fragments of SEQ ID NO:8 with substantial homology (that is, sequence similarity) or substantial identity thereto that have at least about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99% or 100% sequence identity to the corresponding fragments of SEQ ID NO:8; and fragments of SEQ ID NO:8 with substantial homology (that is, sequence similarity) or substantial identity thereto that have at least about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99% or 100% sequence identity to the corresponding fragments of SEQ ID NO:8. The NtNeSy polynucleotide also includes sequences comprising a sufficient or substantial degree of identity or similarity to SEQ ID NO:8 to encode a polypeptide that functions as a lycopene beta cyclase. In one embodiment, the term "NtNeSy polynucleotide" refers to a polymer of nucleotides which comprises, consists or consists essentially of a polynucleotide designated herein as SEQ ID NO:8 that has 100% sequence identity thereto. The term "NtNCED2 polynucleotide", relates to polynucleotides encoding 9-cis-epoxycarotenoid dioxygenase from *Nicotiana tabacum* and includes other polynucleotides comprising, consisting or consisting essentially of polynucleotides with substantial homology (that is, sequence similarity) or substantial identity to SEQ ID NO:13; polynucleotide variants that have at least about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98% or 99% sequence identity to SEQ ID NO:13; fragments of the NtNeSy polynucleotide including fragments of SEQ ID NO:13; fragments of SEQ ID NO:13 with substantial homology (that is, sequence similarity) or substantial identity thereto that have at least about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99% or 100% sequence identity to the corresponding fragments of SEQ ID NO:13. The NtNCED2 polynucleotide also includes sequences comprising a sufficient or substantial degree of identity or similarity to SEQ ID NO:13 to encode a polypeptide that functions as a 9-cis-epoxycarotenoid dioxygenase. In one embodiment, the term "NtNCED2 polynucleotide" refers to a polymer of nucleotides which comprises, consists or consists essentially of a polynucleotide designated herein as SEQ ID NO:13 with 100% sequence identity thereto.

A polynucleotide as described herein will generally contain phosphodiester bonds, although in some cases, polynucleotide analogs are included that may have alternate backbones, comprising, for example, phosphoramidate, phosphorothioate, phosphorodithioate, or O-methylphosphoroamidite linkages; and peptide polynucleotide backbones and linkages. Other analog polynucleotides include those with positive backbones; non-ionic backbones, and non-ribose backbones. Modifications of the ribose-phosphate backbone may be done for a variety of reasons, for example, to increase the stability and half-life of such molecules in physiological environments or as probes on a biochip. Mixtures of naturally occurring polynucleotides and analogs can be made; alternatively, mixtures of different polynucleotide analogs, and mixtures of naturally occurring polynucleotides and analogs may be made.

A variety of polynucleotide analogs are known, including, for example, phosphoramidate, phosphorothioate, phosphorodithioate, O-methylphosphoroamidite linkages and peptide polynucleotide backbones and linkages. Other analog polynucleotides include those with positive backbones, non-ionic backbones and non-ribose backbones. Polynucleotides containing one or more carbocyclic sugars are also included.

Other analogs include peptide polynucleotides which are peptide polynucleotide analogs. These backbones are substantially non-ionic under neutral conditions, in contrast to the highly charged phosphodiester backbone of naturally occurring polynucleotides. This may result in advantages. First, the peptide polynucleotide backbone may exhibit improved hybridization kinetics. Peptide polynucleotides have larger changes in the melting temperature for mismatched versus perfectly matched basepairs. DNA and RNA typically exhibit a 2-4° C. drop in melting temperature for an internal mismatch. With the non-ionic peptide polynucleotide backbone, the drop is closer to 7-9° C. Similarly, due to their non-ionic nature, hybridization of the bases attached to these backbones is relatively insensitive to salt concentration. In addition, peptide polynucleotides may not be degraded or degraded to a lesser extent by cellular enzymes, and thus may be more stable.

Among the uses of the disclosed polynucleotides, and combinations of fragments thereof, is the use of fragments as probes in nucleic acid hybridisation assays or primers for use in nucleic acid amplification assays. Such fragments generally comprise at least about 10, 11, 12, 13, 14, 15, 16, 17, 18, 19 or 20 or more contiguous nucleotides of a DNA sequence. In other embodiments, a DNA fragment comprises at least about 10, 15, 20, 30, 40, 50 or 60 or more contiguous nucleotides of a DNA sequence. Thus, in one aspect, there is also provided a method for detecting an ABA4 polynucleotide comprising the use of the probes or primers or both. Exemplary primers are set forth in SEQ ID NOs: 3 to 5. In another aspect, there is also provided a method for detecting a NeSy polynucleotide comprising the use of the probes or primers or both. Exemplary primers are set forth in SEQ ID NOs: 10 to 12. In another aspect, there is also provided a method for detecting a NCED2 polynucleotide comprising the use of the probes or the primers or both. Exemplary primers are set forth in SEQ ID NOs: 14 to 16.

The basic parameters affecting the choice of hybridization conditions and guidance for devising suitable conditions are described by Sambrook, J., E. F. Fritsch, and T. Maniatis (1989, *Molecular Cloning: A Laboratory Manual*, Cold Spring Harbor Laboratory Press, Cold Spring Harbor, N.Y.). Using knowledge of the genetic code in combination with the amino acid sequences described herein, sets of degenerate oligonucleotides can be prepared. Such oligonucleotides are useful as primers, for example, in polymerase chain reactions (PCR), whereby DNA fragments are isolated and amplified. In certain embodiments, degenerate primers can be used as probes for genetic libraries. Such libraries would include but are not limited to cDNA libraries, genomic libraries, and even electronic express sequence tag or DNA libraries. Homologous sequences identified by this method would then be used as probes to identify homologues of the sequences identified herein.

Also of potential use are polynucleotides and oligonucleotides (for example, primers or probes) that hybridize under reduced stringency conditions, typically moderately stringent conditions, and commonly highly stringent conditions to the polynucleotide(s) as described herein. The basic parameters affecting the choice of hybridization conditions and guidance for devising suitable conditions are set forth by Sambrook, J., E. F. Fritsch, and T. Maniatis (1989, *Molecular Cloning: A Laboratory Manual*, Cold Spring Harbor Laboratory Press, Cold Spring Harbor, N.Y. and can be readily determined by those having ordinary skill in the art based on, for example, the length or base composition of the polynucleotide.

One way of achieving moderately stringent conditions involves the use of a prewashing solution containing 5× Standard Sodium Citrate, 0.5% Sodium Dodecyl Sulphate, 1.0 mM Ethylenediaminetetraacetic acid (pH 8.0), hybridization buffer of about 50% formamide, 6× Standard Sodium Citrate, and a hybridization temperature of about 55° C. (or other similar hybridization solutions, such as one containing about 50% formamide, with a hybridization temperature of about 42° C.), and washing conditions of about 60° C., in 0.5× Standard Sodium Citrate, 0.1% Sodium Dodecyl Sulphate. Generally, highly stringent conditions are defined as hybridization conditions as above, but with washing at approximately 68° C., 0.2× Standard Sodium Citrate, 0.1% Sodium Dodecyl Sulphate. SSPE (1×SSPE is 0.15M sodium chloride, 10 mM sodium phosphate, and 1.25 mM Ethylenediaminetetraacetic acid, pH 7.4) can be substituted for Standard Sodium Citrate (1× Standard Sodium Citrate is 0.15M sodium chloride and 15 mM sodium citrate) in the hybridization and wash buffers; washes are performed for 15 minutes after hybridization is complete. It should be understood that the wash temperature and wash salt concentration can be adjusted as necessary to achieve a desired degree of stringency by applying the basic principles that govern hybridization reactions and duplex stability, as known to those skilled in the art and described further below (see, for example, Sambrook, J., E. F. Fritsch, and T. Maniatis (1989, *Molecular Cloning: A Laboratory Manual*, Cold Spring Harbor Laboratory Press, Cold Spring Harbor, N.Y.). When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity. The hybridization temperature for hybrids anticipated to be less than 50 base pairs in length should be 5 to 10° C. less than the melting temperature of the hybrid, where melting temperature is determined according to the following equations. For hybrids less than 18 base pairs in length, melting temperature (° C.)=2(number of A+T bases)+4(number of G+C bases). For hybrids above 18 base pairs in length, melting temperature (° C.)=81.5+16.6(log 10 [Na+])+0.41(% G+C)−(600/N), where N is the number of bases in the hybrid, and [Na+] is the concentration of sodium ions in the hybridization buffer ([Na+] for 1× Standard Sodium Citrate=0.165M). Typically, each such hybridizing polynucleotide has a length that is at least 25% (commonly at least 50%, 60%, or 70%, and most commonly at least 80%) of the length of a polynucleotide to which it hybridizes, and has at least 60% sequence identity (for example, at least 70%, 75%, 80%, 85%, 90%, 95%, 96%, 97%, 98%, 99% or 100%) with a polynucleotide to which it hybridizes.

As will be understood by the person skilled in the art, a linear DNA has two possible orientations: the 5'-to-3' direction and the 3'-to-5' direction. For example, if a reference sequence is positioned in the 5'-to-3' direction, and if a second sequence is positioned in the 5'-to-3' direction within the same polynucleotide molecule/strand, then the reference sequence and the second sequence are orientated in the same direction, or have the same orientation. Typically, a promoter sequence and a gene of interest under the regulation of the given promoter are positioned in the same orientation. However, with respect to the reference sequence positioned in the 5'-to-3' direction, if a second sequence is positioned in the 3'-to-5' direction within the same polynucleotide molecule/strand, then the reference sequence and the second sequence are orientated in anti-sense direction, or have anti-sense orientation. Two sequences having anti-sense orientations with respect to each other can be alternatively described as having the same orientation, if the reference sequence (5'-to-3' direction) and the reverse complementary sequence of the reference sequence (reference sequence positioned in the 5'-to-3') are positioned within the same polynucleotide molecule/strand. The sequences set forth herein are shown in the 5'-to-3' direction. Recombinant constructs provided herein can be used to transform plants or plant cells in order to modulate protein expression or activity levels. A recombinant polynucleotide construct can comprise a polynucleotide encoding one or more polynucleotides as described herein, operably linked to a regulatory region suitable for expressing the polypeptide in the plant or plant cell. Thus, a polynucleotide can comprise a coding sequence that encodes the polypeptide as described herein. Plants in which protein expression or activity levels are modulated can include mutant plants, non-naturally occurring plants, transgenic plants, man-made plants or genetically engineered plants. Suitably, the transgenic plant comprises a genome that has been altered by the stable integration of recombinant DNA. Recombinant DNA includes DNA which has been a genetically engineered and constructed outside of a cell and includes DNA containing naturally occurring DNA or cDNA or synthetic DNA. A transgenic plant can include a plant regenerated from an originally-transformed plant cell and progeny transgenic plants from later generations or crosses of a transformed plant.

The polypeptide encoded by a recombinant polynucleotide can be a native polypeptide, or can be heterologous to the cell. In some cases, the recombinant construct contains a polynucleotide that modulates expression, operably linked to a regulatory region. Examples of suitable regulatory regions are described herein.

Vectors containing recombinant polynucleotide constructs such as those described herein are also provided. Suitable vector backbones include, for example, those routinely used in the art such as plasmids, viruses, artificial chromosomes, bacterial artificial chromosomes, yeast artificial chromosomes, or bacteriophage artificial chromosomes. Suitable expression vectors include, without limitation, plasmids and viral vectors derived from, for example, bacteriophage, baculoviruses, and retroviruses. Numerous vectors and expression systems are commercially available.

The vectors can also include, for example, origins of replication, scaffold attachment regions or markers. A marker gene can confer a selectable phenotype on a plant cell. For example, a marker can confer biocide resistance, such as resistance to an antibiotic (for example, kanamycin, G418, bleomycin, or hygromycin), or an herbicide (for example, glyphosate, chlorsulfuron or phosphinothricin). In addition, an expression vector can include a tag sequence designed to facilitate manipulation or detection (for example, purification or localization) of the expressed polypeptide. Tag sequences, such as luciferase, beta-glucuronidase, green fluorescent protein, glutathione S-transferase, polyhistidine, c-myc or hemagglutinin sequences typically are expressed as a fusion with the encoded polypeptide. Such tags can be inserted anywhere within the polypeptide, including at either the carboxyl or amino terminus.

A plant or plant cell can be transformed by having the recombinant polynucleotide integrated into its genome to become stably transformed. The plant or plant cell described herein can therefore be stably transformed. Stably transformed cells typically retain the introduced polynucleotide with each cell division. A plant or plant cell may also be transiently transformed such that the recombinant polynucleotide is not integrated into its genome. Transiently transformed cells typically lose all or some portion of the introduced recombinant polynucleotide with each cell division such that the introduced recombinant polynucleotide cannot be detected in daughter cells after a sufficient number of cell divisions.

A number of methods are available in the art for transforming a plant cell which are all encompassed herein, including biolistics, gene gun techniques, *Agrobacterium*-mediated transformation, viral vector-mediated transformation and electroporation. The *Agrobacterium* system for integration of foreign DNA into plant chromosomes has been extensively studied, modified, and exploited for plant genetic engineering. Naked recombinant DNA molecules comprising DNA sequences corresponding to the subject purified tobacco protein operably linked, in the sense or antisense orientation, to regulatory sequences are joined to appropriate T-DNA sequences by conventional methods. These are introduced into tobacco protoplasts by polyethylene glycol techniques or by electroporation techniques, both of which are standard. Alternatively, such vectors comprising recombinant DNA molecules encoding the subject purified tobacco protein are introduced into live *Agrobacterium* cells, which then transfer the DNA into the tobacco plant cells. Transformation by naked DNA without accompanying T-DNA vector sequences can be accomplished via fusion of tobacco protoplasts with DNA-containing liposomes or via electroporation. Naked DNA unaccompanied by T-DNA vector sequences can also be used to transform tobacco cells via inert, high velocity microprojectiles.

If a cell or cultured tissue is used as the recipient tissue for transformation, plants can be regenerated from transformed cultures if desired, by techniques known to those skilled in the art.

The choice of regulatory regions to be included in a recombinant construct depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning regulatory regions relative to the coding sequence. Transcription of a polynucleotide can be modulated in a similar manner. Some suitable regulatory regions initiate transcription only, or predominantly, in certain cell types. Methods for identifying and characterizing regulatory regions in plant genomic DNA are known in the art.

Suitable promoters include tissue-specific promoters recognized by tissue-specific factors present in different tissues or cell types (for example, root-specific promoters, shoot-specific promoters, xylem-specific promoters), or present during different developmental stages, or present in response to different environmental conditions. Suitable promoters include constitutive promoters that can be activated in most cell types without requiring specific inducers. Examples of suitable promoters for controlling RNAi polypeptide production include the cauliflower mosaic virus 35S (CaMV/35S), SSU, OCS, lib4, usp, STLS1, B33, nos or ubiquitin- or phaseolin-promoters. Persons skilled in the art are capable of generating multiple variations of recombinant promoters.

Tissue-specific promoters are transcriptional control elements that are only active in particular cells or tissues at specific times during plant development, such as in vegetative tissues or reproductive tissues. Tissue-specific expression can be advantageous, for example, when the expression of polynucleotides in certain tissues is preferred. Examples of tissue-specific promoters under developmental control include promoters that can initiate transcription only (or primarily only) in certain tissues, such as vegetative tissues, for example, roots or leaves, or reproductive tissues, such as fruit, ovules, seeds, pollen, pistils, flowers, or any embryonic tissue. Reproductive tissue-specific promoters may be, for example, anther-specific, ovule-specific, embryo-specific, endosperm-specific, integument-specific, seed and seed coat-specific, pollen-specific, petal-specific, sepal-specific, or combinations thereof.

Suitable leaf-specific promoters include pyruvate, orthophosphate dikinase (PPDK) promoter from C4 plant (maize), cab-m1Ca+2 promoter from maize, the *Arabidopsis thaliana* myb-related gene promoter (Atmyb5), the ribulose biphosphate carboxylase (RBCS) promoters (for example, the tomato RBCS 1, RBCS2 and RBCS3A genes expressed in leaves and light-grown seedlings, RBCS1 and RBCS2 expressed in developing tomato fruits or ribulose bisphosphate carboxylase promoter expressed almost exclusively in mesophyll cells in leaf blades and leaf sheaths at high levels).

Suitable senescence-specific promoters include a tomato promoter active during fruit ripening, senescence and abscission of leaves, a maize promoter of gene encoding a cysteine protease. Suitable anther-specific promoters can be used. Suitable root-preferred promoters known to persons skilled in the art may be selected. Suitable seed-preferred promoters include both seed-specific promoters (those promoters active during seed development such as promoters of seed storage proteins) and seed-germinating promoters (those promoters active during seed germination). Such seed-preferred promoters include, but are not limited to, Cim1 (cytokinin-induced message); cZ19B1 (maize 19 kDa zein); milps (myo-inositol-1-phosphate synthase); mZE40-2, also known as Zm-40; nucic; and celA (cellulose synthase). Gama-zein is an endosperm-specific promoter. Glob-1 is an embryo-specific promoter. For dicots, seed-specific promoters include, but are not limited to, bean beta-phaseolin, napin, β-conglycinin, soybean lectin, cruciferin, and the like. For monocots, seed-specific promoters include, but are not limited to, a maize 15 kDa zein promoter, a 22 kDa zein promoter, a 27 kDa zein promoter, a g-zein promoter, a 27 kDa gamma-zein promoter (such as gzw64A promoter, see Genbank Accession number S78780), a waxy promoter, a shrunken 1 promoter, a shrunken 2 promoter, a globulin 1 promoter (see Genbank Accession number L22344), an Itp2 promoter, cim1 promoter, maize end1 and end2 promoters, nuc1 promoter, Zm40 promoter, eep1 and eep2; lec1, thioredoxin H promoter; mlip15 promoter, PCNA2 promoter; and the shrunken-2 promoter.

Examples of inducible promoters include promoters responsive to pathogen attack, anaerobic conditions, elevated temperature, light, drought, cold temperature, or high salt concentration. Pathogen-inducible promoters include those from pathogenesis-related proteins (PR proteins), which are induced following infection by a pathogen (for example, PR proteins, SAR proteins, beta-1,3-glucanase, chitinase).

In addition to plant promoters, other suitable promoters may be derived from bacterial origin for example, the octopine synthase promoter, the nopaline synthase promoter and other promoters derived from Ti plasmids), or may be derived from viral promoters (for example, 35S and 19S RNA promoters of cauliflower mosaic virus (CaMV), constitutive promoters of tobacco mosaic virus, cauliflower mosaic virus (CaMV) 19S and 35S promoters, or figwort mosaic virus 35S promoter).

The term "NtABA4 polypeptide" refers to a polypeptide encoding so-called "neoxanthin synthase" from *Nicotiana tabacum* and includes other polypeptide variants comprising, consisting or consisting essentially of an amino acid sequence encoded by a polynucleotide variant with at least about 66%, 67%, 68%, 69%, 70%, 75%, 80%, 85%, 87%, 88%, 89%, 90%, 91%, 92%, 93%, 94%, 95% 96%, 97%, 98% or 99% sequence identity to SEQ ID NO:1 or a polynucleotide variant with at least about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98% or 99% sequence identity to SEQ ID NO:6; a polypeptide variant having at least about 66%, 67%, 68%, 69%, 70%, 75%, 80%, 85%, 87%, 88%, 89%, 90%, 91%, 92%, 93%, 94%, 95% 96%, 97%, 98%, or 99% sequence identity to SEQ ID NO:2 or a polypeptide variant having at least about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98% or 99% sequence identity SEQ ID No. 7; fragments of the NtABA4 polypeptide of SEQ ID NO:2 or SEQ ID NO:7; and fragments of SEQ ID NO:2 or SEQ ID NO: 7 that have at least about 60%, 65%, 70%, 75%, 80%, 85%, 87%, 88%, 89%, 90%, 91%, 92%, 93%, 94%, 95% 96%, 97%, 98%, 99% or 100% sequence identity to the corresponding fragments of SEQ ID NO:2 or SEQ ID NO: 7, respectively. The NtABA4 polypeptide(s) also includes sequences comprising a sufficient or substantial degree of identity or similarity to SEQ ID NO:2 or SEQ ID NO:7 to function as a neoxanthin synthase. The fragments of the NtABA4 polypeptide typically retain neoxanthin synthase activity. NtABA4 polypeptides also include mutants produced by introducing any type of alterations (for example, insertions, deletions, or substitutions of amino acids; changes in glycosylation states; changes that affect refolding or isomerizations, three-dimensional structures, or self-association states), which can be deliberately engineered or isolated naturally provided that they still function as a neoxanthin synthase. NtABA4 polypeptides may be in linear form or cyclized using known methods. The term "NtABA4 polypeptide" can also refer to a polypeptide encoded by SEQ ID NO:1 or SEQ ID NO:6 that has 100% sequence identity thereto or a polypeptide comprising, consisting or consisting essentially of the sequence set forth in SEQ ID NO:2 or SEQ ID NO:7 that has 100% sequence identity thereto.

The term "NtNeSy polypeptide" refers to a polypeptide encoding lycopene beta cyclase from *Nicotiana tabacum* and includes other polypeptide variants comprising, consisting or consisting essentially of an amino acid sequence encoded by a polynucleotide with at least about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99% or 100% sequence identity to SEQ ID NO:9; a polypeptide variant having at least 87%, 88%, 89%, 90%, 91%, 92%, 93%, 94%, 95% 96%, 97%, 98%, 99% or 100% sequence identity to SEQ ID NO:9; fragments of the NtNeSy polypeptide of SEQ ID NO:9; and fragments of SEQ ID NO:9 that have at least about 60%, 61%, 62%, 63%, 64%, 65%, 70%, 75%, 80%, 85%, 87%, 88%, 89%, 90%, 91%, 92%, 93%, 94%, 95% 96%, 97%, 98%, 99% or 100% sequence identity to the corresponding fragments of SEQ ID NO:9. The NtNeSy polypeptides also include sequences comprising a sufficient or substantial degree of identity or similarity to SEQ ID NO:9 to function as a lycopene beta cyclase. The fragments of the NtNeSy polypeptide typically retain lycopene beta cyclase activity. NtNeSy polypeptides also include variants and mutants produced by introducing any type of alterations (for example, insertions, deletions, or substitutions of amino acids; changes in glycosylation states; changes that affect refolding or isomerizations, three-dimensional structures, or self-association states), which can be deliberately engineered or isolated naturally provided that they still function as a lycopene beta cyclase. NtNeSy polypeptides may be in linear form or cyclized using known methods. The term "NtNeSy polypeptide" can also refer to a polypeptide comprising, consisting or consisting essentially of the sequence set forth in SEQ ID NO:9 with 100% sequence identity thereto.

The term "NtNCED2 polypeptide" refers to a polypeptide encoding 9-cis-epoxycarotenoid dioxygenase from *Nicotiana tabacum* and includes a polypeptide comprising, consisting or consisting essentially of an amino acid sequence encoded by a polynucleotide with 100% sequence identity to SEQ ID NO:13; or a polypeptide variant comprising, consisting or consisting essentially of an amino acid sequence encoded by a polynucleotide with at least about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98% or 99% sequence identity to SEQ ID NO:13. Fragments of the NtNCED2 polypeptide are also encompassed that typically retain 9-cis-epoxycarotenoid dioxygenase activity. NtNCED2 polypeptides also include variants and mutants produced by introducing any type of alterations (for example, insertions, deletions, or substitutions of amino acids; changes in glycosylation states; changes that affect refolding or isomerizations, three-dimensional structures, or self-association states), which can be deliberately engineered or isolated naturally provided that they still function as a 9-cis-epoxycarotenoid dioxygenase. NtNCED2 polypeptides may be in linear form or cyclized using known methods.

In another aspect, there is provided an isolated polypeptide comprising, consisting or consisting essentially of a polypeptide sequence having at least 60% sequence identity to any of the sequences described herein, including any of the polypeptides shown in the sequence listing. Suitably, the isolated polypeptide comprises, consists or consists essentially of a sequence having at least 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99% or 100% sequence identity thereto.

Polypeptides include variants produced by introducing any type of alterations (for example, insertions, deletions, or substitutions of amino acids; changes in glycosylation states; changes that affect refolding or isomerizations, three-dimensional structures, or self-association states), which can be deliberately engineered or isolated naturally. The variant may have alterations which produce a silent change and result in a functionally equivalent protein. Deliberate amino acid substitutions may be made on the basis of similarity in polarity, charge, solubility, hydrophobicity, hydrophilicity and the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine. Conservative substitutions may be made, for example according to the Table below. Amino acids in the same block in the second column and preferably in the same line in the third column may be substituted for each other:

| ALIPHATIC | Non-polar | Gly Ala Pro Ile Leu Val |
|---|---|---|
| | Polar - uncharged | Cys Ser Thr Met Asn Gly |
| | Polar - charged | Asp Glu Lys Arg |
| AROMATIC | | His Phe Trp Tyr |

The polypeptide may be a mature protein or an immature protein or a protein derived from an immature protein. Polypeptides may be in linear form or cyclized using known methods. Polypeptides typically comprise at least 10, at least 20, at least 30, or at least 40 contiguous amino acids.

In one embodiment, there is provided an isolated NtABA4 polypeptide comprising, consisting or consisting essentially of a sequence encoding a neoxanthin synthase and having at least about 66%, 67%, 68%, 69%, 70%, 75%, 80%, 85%, 87%, 88%, 89%, 90%, 91%, 92%, 93%, 94%, 95% 96%, 97%, 98%, 99% or 100% sequence identity to SEQ ID NO:2 or about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99% or 100% sequence identity to SEQ ID NO:7.

In another embodiment, there is provided an isolated NtNeSy polypeptide comprising, consisting or consisting essentially of a sequence encoding a lycopene beta cyclase and having at least about 87%, 88%, 89%, 90%, 91%, 92%, 93%, 94%, 95% 96%, 97%, 98%, 99% or 100% sequence identity to SEQ ID NO:9.

In another embodiment, there is provided an isolated NtNCED2 polypeptide encoded by the NtNCED2 polynucleotide that is described herein.

Fragments of the polypeptide sequences are also disclosed herein, suitably, such fragments retain the activity of the full length sequence.

Mutant polypeptide variants can be used to create mutant, non-naturally occurring or transgenic plants (for example, mutant, non-naturally occurring, transgenic, man-made or genetically engineered plants) comprising one or more mutant polypeptide variants. Suitably, the mutant polypeptide variants retain the activity of the unmutated polypeptide. The activity of the mutant polypeptide variant may be higher, lower or about the same as the unmutated polypeptide.

Mutations in the nucleotide sequences and polypeptides described herein can include man made mutations or synthetic mutations or genetically engineered mutations. Mutations in the nucleotide sequences and polypeptides described herein can be mutations that are obtained or obtainable via a process which includes an in vitro or an in vivo manipulation step. Mutations in the nucleotide sequences and polypeptides described herein can be mutations that are obtained or obtainable via a process which includes intervention by man. By way of example, the process may include mutagenesis using exogenously added chemicals—such as mutagenic, teratogenic, or carcinogenic organic compounds, for example ethyl methanesulfonate (EMS), that produce random mutations in genetic material. By way of further example, the process may include one or more genetic engineering steps—such as one or more of the genetic engineering steps that are described herein or combinations thereof. By way of further example, the process may include one or more plant crossing steps.

As used herein, the term 'non-naturally occurring' means that the entity—such as the polypeptide, the polynucleotide or the plant and the like is not found in nature and therefore expressly excludes entities that exist in nature. Such non-naturally occurring entities may be structurally modified, synthesised or manipulated by man. In certain embodiments, a mutation is not a naturally occurring mutation that exists naturally in a nucleotide sequence or a polypeptide—such as a gene or a protein.

A polypeptide may be prepared by culturing transformed or recombinant host cells under culture conditions suitable to express a polypeptide. The resulting expressed polypeptide may then be purified from such culture using known purification processes. The purification of the polypeptide may include an affinity column containing agents which will bind to the polypeptide; one or more column steps over such affinity resins; one or more steps involving hydrophobic interaction chromatography; or immunoaffinity chromatography. Alternatively, the polypeptide may also be expressed in a form that will facilitate purification. For example, it may be expressed as a fusion polypeptide, such as those of maltose binding polypeptide, glutathione-S-transferase or thioredoxin. Kits for expression and purification of fusion polypeptides are commercially available. The polypeptide may be tagged with an epitope and subsequently purified by using a specific antibody directed to such epitope. One or more liquid chromatography steps—such as reverse-phase high performance liquid chromatography can be employed to further purify the polypeptide. Some or all of the foregoing purification steps, in various combinations, can be employed to provide a substantially homogeneous recombinant polypeptide. The polypeptide thus purified may be substantially free of other polypeptides and is defined herein as a "substantially purified polypeptide"; such purified polypeptides include polypeptides, fragments, variants, and the like. Expression, isolation, and purification of the polypeptides and fragments can be accomplished by any suitable technique, including but not limited to the methods described herein.

It is also possible to utilise an affinity column such as a monoclonal antibody generated against polypeptides, to affinity-purify expressed polypeptides. These polypeptides can be removed from an affinity column using conventional techniques, for example, in a high salt elution buffer and then dialyzed into a lower salt buffer for use or by changing pH or other components depending on the affinity matrix utilized, or be competitively removed using the naturally occurring substrate of the affinity moiety.

A polypeptide may also be produced by known conventional chemical synthesis. Methods for constructing the polypeptides or fragments thereof by synthetic means are known to those skilled in the art. The synthetically-constructed polypeptide sequences, by virtue of sharing primary, secondary or tertiary structural or conformational characteristics with native polypeptides may possess biological properties in common therewith, including biological activity.

The term 'non-naturally occurring' as used herein describes an entity (for example, a polynucleotide, a genetic mutation, a polypeptide, a plant, a plant cell and plant material) that is not formed by nature or that does not exist in nature. Such non-naturally occurring entities or artificial entities may be made, synthesized, initiated, modified, intervened, or manipulated by methods described herein or that are known in the art. Thus, by way of example, a non-naturally occurring plant, a non-naturally occurring plant cell or non-naturally occurring plant material may be made using traditional plant breeding techniques—such as backcrossing—or by genetic manipulation technologies—such as antisense RNA, interfering RNA, meganuclease and the like. By way of further example, a non-naturally occurring plant, a non-naturally occurring plant cell or non-naturally occurring plant material may be made by introgression of or by transferring one or more genetic mutations (for example one or more polymorphisms) from a first plant or plant cell into a second plant or plant cell (which may itself be naturally occurring), such that the resulting plant, plant cell or plant material or the progeny thereof comprises a genetic constitution (for example, a genome, a chromosome or a segment thereof) that is not formed by nature or that does not exist in nature. The resulting plant, plant cell or plant material is thus artificial or non-naturally occurring. Accordingly, an artificial or non-naturally occurring plant or plant cell may be made by modifying a genetic sequence in a first naturally occurring plant or plant cell, even if the resulting genetic sequence occurs naturally in a second plant or plant cell that comprises a different genetic background from the first plant or plant cell. Differences in genetic background can be detected by phenotypic differences or by molecular biology techniques known in the art—such as nucleic acid sequencing, presence or absence of genetic markers (for example, microsatellite RNA markers).

Antibodies that are immunoreactive with the NtABA4 or NtNeSy or NtNCED2 polypeptides described herein are also provided. The polypeptides, fragments, variants, fusion polypeptides, and the like, as set forth herein, can be employed as "immunogens" in producing antibodies immunoreactive therewith. Such antibodies may specifically bind to the polypeptide via the antigen-binding sites of the antibody. Specifically binding antibodies are those that will specifically recognize and bind with a polypeptide, homologues, and variants, but not with other molecules. In one embodiment, the antibodies are specific for polypeptides having an amino acid sequence as set forth herein and do not cross-react with other polypeptides.

More specifically, the polypeptides, fragment, variants, fusion polypeptides, and the like contain antigenic determinants or epitopes that elicit the formation of antibodies. These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon polypeptide folding. Epitopes can be identified by any of the methods known in the art. Additionally, epitopes from the polypeptides can be used as research reagents, in assays, and to purify specific binding antibodies from substances such as polyclonal sera or supernatants from cultured hybridomas. Such epitopes or variants thereof can be produced using techniques known in the art such as solid-phase synthesis, chemical or enzymatic cleavage of a polypeptide, or using recombinant DNA technology.

Both polyclonal and monoclonal antibodies to the polypeptides can be prepared by conventional techniques. Hybridoma cell lines that produce monoclonal antibodies specific for the polypeptides are also contemplated herein. Such hybridomas can be produced and identified by conventional techniques. For the production of antibodies, various host animals may be immunized by injection with a polypeptide, fragment, variant, or mutants thereof. Such host animals may include, but are not limited to, rabbits, mice, and rats, to name a few. Various adjutants may be used to increase the immunological response. Depending on the host species, such adjuvants include, but are not limited to, Freund's (complete and incomplete), mineral gels such as aluminium hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. The monoclonal antibodies can be recovered by conventional techniques. Such monoclonal antibodies may be of any immunoglobulin class including IgG, IgM, IgE, IgA, IgD, and any subclass thereof.

The antibodies can also be used in assays to detect the presence of the polypeptides or fragments, either in vitro or in vivo. The antibodies also can be employed in purifying polypeptides or fragments by immunoaffinity chromatography.

Compositions that can modulate (for example, increase) the expression or the activity of NtABA4 or NtNeSy or NtNCED2 (or a combination of two or more or three or more thereof) include, but are not limited to, sequence-specific polynucleotides that can interfere with the transcription of one or more endogenous gene(s); sequence-specific polynucleotides that can interfere with the translation of RNA transcripts (for example, double-stranded RNAs, siRNAs, ribozymes); sequence-specific polypeptides that can interfere with the stability of one or more proteins; sequence-specific polynucleotides that can interfere with the enzymatic activity of one or more proteins or the binding activity of one or more proteins with respect to substrates or regulatory proteins; antibodies that exhibit specificity for one or more proteins; small molecule compounds that can interfere with the stability of one or more proteins or the enzymatic activity of one or more proteins or the binding activity of one or more proteins; zinc finger proteins that bind one or more polynucleotides; and meganucleases that have activity towards one or more polynucleotides. Gene editing technologies, genetic editing technologies and genome editing technologies are well known in the art.

Antisense technology is one well-known method that can be used to modulate the expression of a polypeptide. A polynucleotide of the gene to be repressed is cloned and operably linked to a regulatory region and a transcription termination sequence so that the antisense strand of RNA is transcribed. The recombinant construct is then transformed into plants and the antisense strand of RNA is produced. The polynucleotide need not be the entire sequence of the gene to be repressed, but typically will be substantially complementary to at least a portion of the sense strand of the gene to be repressed.

A polynucleotide may be transcribed into a ribozyme, or catalytic RNA, that affects expression of an mRNA. Ribozymes can be designed to specifically pair with virtually any target RNA and cleave the phosphodiester backbone at a specific location, thereby functionally inactivating the target RNA. Heterologous polynucleotides can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' nucleotide sequence. The construction and production of hammerhead ribozymes is known in the art.

Hammerhead ribozyme sequences can be embedded in a stable RNA such as a transfer RNA (tRNA) to increase cleavage efficiency in vivo.

In one embodiment, the sequence-specific polynucleotide that can interfere with the translation of RNA transcript(s) is interfering RNA. RNA interference or RNA silencing is an evolutionarily conserved process by which specific mRNAs can be targeted for enzymatic degradation. A double-stranded RNA (double-stranded RNA) is introduced or produced by a cell (for example, double-stranded RNA virus, or interfering RNA polynucleotides) to initiate the interfering RNA pathway. The double-stranded RNA can be converted into multiple small interfering RNA duplexes of 21-23 bp length by RNases III, which are double-stranded RNA-specific endonucleases. The small interfering RNAs can be subsequently recognized by RNA-induced silencing complexes that promote the unwinding of small interfering RNA through an ATP-dependent process. The unwound antisense strand of the small interfering RNA guides the activated RNA-induced silencing complexes to the targeted mRNA comprising a sequence complementary to the small interfering RNA anti-sense strand. The targeted mRNA and the anti-sense strand can form an A-form helix, and the major groove of the A-form helix can be recognized by the activated RNA-induced silencing complexes. The target mRNA can be cleaved by activated RNA-induced silencing complexes at a single site defined by the binding site of the 5'-end of the small interfering RNA strand. The activated RNA-induced silencing complexes can be recycled to catalyze another cleavage event.

interfering RNA expression vectors may comprise interfering RNA constructs encoding interfering RNA polynucleotides that exhibit RNA interference activity by reducing the expression level of mRNAs, pre-mRNAs, or related RNA variants. The expression vectors may comprise a promoter positioned upstream and operably-linked to an Interfering RNA construct, as further described herein. Interfering RNA expression vectors may comprise a suitable minimal core promoter, a Interfering RNA construct of interest, an upstream (5') regulatory region, a downstream (3') regulatory region, including transcription termination and polyadenylation signals, and other sequences known to persons skilled in the art, such as various selection markers.

The polynucleotides can be produced in various forms, including as double stranded structures (that is, a double-stranded RNA molecule comprising an antisense strand and a complementary sense strand), double-stranded hairpin-like structures, or single-stranded structures (that is, a ssRNA molecule comprising just an antisense strand). The structures may comprise a duplex, asymmetric duplex, hairpin or asymmetric hairpin secondary structure, having self-complementary sense and antisense strands. The double stranded interfering RNA can be enzymatically converted to double-stranded small interfering RNAs. One of the strands of the small interfering RNA duplex can anneal to a complementary sequence within the target mRNA and related RNA variants. The small interfering RNA/mRNA duplexes are recognized by RNA-induced silencing complexes that can cleave RNAs at multiple sites in a sequence-dependent manner, resulting in the degradation of the target mRNA and related RNA variants.

The double-stranded RNA molecules may include small interfering RNA molecules assembled from a single oligonucleotide in a stem-loop structure, wherein self-complementary sense and antisense regions of the small interfering RNA molecule are linked by means of a polynucleotide based or non-polynucleotide-based linker(s), as well as circular single-stranded RNA having two or more loop structures and a stem comprising self-complementary sense and antisense strands, wherein the circular RNA can be processed either in vivo or in vitro to generate an active small interfering RNA molecule capable of mediating Interfering RNA.

The use of small hairpin RNA molecules is also contemplated. They comprise a specific antisense sequence in addition to the reverse complement (sense) sequence, typically separated by a spacer or loop sequence. Cleavage of the spacer or loop provides a single-stranded RNA molecule and its reverse complement, such that they may anneal to form a double-stranded RNA molecule (optionally with additional processing steps that may result in addition or removal of one, two, three or more nucleotides from the 3' end or the 5' end of either or both strands). The spacer can be of a sufficient length to permit the antisense and sense sequences to anneal and form a double-stranded structure (or stem) prior to cleavage of the spacer (and, optionally, subsequent processing steps that may result in addition or removal of one, two, three, four, or more nucleotides from the 3' end or the 5' end of either or both strands). The spacer sequence is typically an unrelated nucleotide sequence that is situated between two complementary nucleotide sequence regions which, when annealed into a double-stranded polynucleotide, comprise a small hairpin RNA. The spacer sequence generally comprises between about 3 and about 100 nucleotides.

Any RNA polynucleotide of interest can be produced by selecting a suitable sequence composition, loop size, and stem length for producing the hairpin duplex. A suitable range for designing stem lengths of a hairpin duplex, includes stem lengths of at least about 10, 11, 12, 13, 14, 15, 16, 17, 18, 19 or 20 nucleotides—such as about 14-30 nucleotides, about 30-50 nucleotides, about 50-100 nucleotides, about 100-150 nucleotides, about 150-200 nucleotides, about 200-300 nucleotides, about 300-400 nucleotides, about 400-500 nucleotides, about 500-600 nucleotides, and about 600-700 nucleotides. A suitable range for designing loop lengths of a hairpin duplex, includes loop lengths of about 4-25 nucleotides, about 25-50 nucleotides, or longer if the stem length of the hair duplex is substantial. In certain embodiments, a double-stranded RNA or ssRNA molecule is between about 15 and about 40 nucleotides in length. In another embodiment, the small interfering RNA molecule is a double-stranded RNA or ssRNA molecule between about 15 and about 35 nucleotides in length. In another embodiment, the small interfering RNA molecule is a double-stranded RNA or ssRNA molecule between about 17 and about 30 nucleotides in length. In another embodiment, the small interfering RNA molecule is a double-stranded RNA or ssRNA molecule between about 19 and about 25 nucleotides in length. In another embodiment, the small interfering RNA molecule is a double-stranded RNA or ssRNA molecule between about 21 to about 23 nucleotides in length. In certain embodiments, hairpin structures with duplexed regions longer than 21 nucleotides may promote effective small interfering RNA-directed silencing, regardless of loop sequence and length.

The target mRNA sequence is typically between about 14 to about 50 nucleotides in length. The target mRNA can, therefore, be scanned for regions between about 14 and about 50 nucleotides in length that preferably meet one or more of the following criteria for a target sequence: an A+T/G+C ratio of between about 2:1 and about 1:2; an AA dinucleotide or a CA dinucleotide at the 5' end of the target sequence; a sequence of at least 10 consecutive nucleotides unique to the target mRNA (that is, the sequence is not present in other mRNA sequences from the same plant); and no "runs" of more than three consecutive guanine (G) nucleotides or more than three consecutive cytosine (C) nucleotides. These criteria can be assessed using various techniques known in the art, for example, computer programs such as BLAST can be used to search publicly available databases to determine whether the selected target sequence is unique to the target mRNA. Alternatively, a target sequence can be selected (and a small interfering RNA sequence designed) using computer software available commercially (for example, OligoEngine, Target Finder and the small interfering RNA Design Tool which are commercially available.

In one embodiment, target mRNA sequences are selected that are between about 14 and about 30 nucleotides in length that meet one or more of the above criteria. In another embodiment, target sequences are selected that are between about 16 and about 30 nucleotides in length that meet one or more of the above criteria. In a further embodiment, target sequences are selected that are between about 19 and about 30 nucleotides in length that meet one or more of the above criteria. In another embodiment, target sequences are selected that are between about 19 and about 25 nucleotides in length that meet one or more of the above criteria.

In an exemplary embodiment, the small interfering RNA molecules comprise a specific antisense sequence that is complementary to at least 12, 13, 14, 15, 16, 17, 18, 19, 20, 21, 22, 23, 24, 25, 26, 27, 28, 29, 30, or more contiguous nucleotides of any one of the polynucleotide sequences described herein.

The specific antisense sequence comprised by the small interfering RNA molecule can be identical or substantially identical to the complement of the target sequence. In one embodiment, the specific antisense sequence comprised by the small interfering RNA molecule is at least about 75%, 80%, 85%, 90%, 95%, 96%, 97%, 98%, 99% or 100% identical to the complement of the target mRNA sequence. Methods of determining sequence identity are known in the art and can be determined, for example, by using the BLASTN program of the University of Wisconsin Computer Group (GCG) software or provided on the NCBI website.

The specific antisense sequence of the small interfering RNA molecules may exhibit variability by differing (for example, by nucleotide substitution, including transition or transversion) at one, two, three, four or more nucleotides from the sequence of the target mRNA. When such nucleotide substitutions are present in the antisense strand of a double-stranded RNA molecule, the complementary nucleotide in the sense strand with which the substitute nucleotide would typically form hydrogen bond base-pairing may or may not be correspondingly substituted. Double-stranded RNA molecules in which one or more nucleotide substitution occurs in the sense sequence, but not in the antisense strand, are also contemplated. When the antisense sequence of an small interfering RNA molecule comprises one or more mismatches between the nucleotide sequence of the small interfering RNA and the target nucleotide sequence, as described above, the mismatches may be found at the 3' terminus, the 5' terminus or in the central portion of the antisense sequence.

In another embodiment, the small interfering RNA molecules comprise a specific antisense sequence that is capable of selectively hybridizing under stringent conditions to a portion of a naturally occurring target gene or target mRNA. As known to those of ordinary skill in the art, variations in stringency of hybridization conditions may be achieved by altering the time, temperature or concentration of the solutions used for the hybridization and wash steps. Suitable conditions can also depend in part on the particular nucleotide sequences used, for example the sequence of the target mRNA or gene.

One method for inducing double stranded RNA-silencing in plants is transformation with a gene construct producing hairpin RNA (see Smith et al. (2000) *Nature*, 407, 319-320). Such constructs comprise inverted regions of the target gene sequence, separated by an appropriate spacer. The insertion of a functional plant intron region as a spacer fragment additionally increases the efficiency of the gene silencing induction, due to generation of an intron spliced hairpin RNA (Wesley et al. (2001) *Plant J.*, 27, 581-590). Suitably, the stem length is about 50 nucleotides to about 1 kilobases in length. Methods for producing intron spliced hairpin RNA are well described in the art (see for example, *Bioscience, Biotechnology, and Biochemistry* (2008) 72, 2, 615-617).

Interfering RNA molecules having a duplex or double-stranded structure, for example double-stranded RNA or small hairpin RNA, can have blunt ends, or can have 3' or 5' overhangs. As used herein, "overhang" refers to the unpaired nucleotide or nucleotides that protrude from a duplex structure when a 3'-terminus of one RNA strand extends beyond the 5'-terminus of the other strand (3' overhang), or vice versa (5' overhang). The nucleotides comprising the overhang can be ribonucleotides, deoxyribonucleotides or modified versions thereof. In one embodiment, at least one strand of the interfering RNA molecule has a 3' overhang from about 1 to about 6 nucleotides in length. In other embodiments, the 3' overhang is from about 1 to about 5 nucleotides, from about 1 to about 3 nucleotides and from about 2 to about 4 nucleotides in length.

When the interfering RNA molecule comprises a 3' overhang at one end of the molecule, the other end can be blunt-ended or have also an overhang (5' or 3'). When the interfering RNA molecule comprises an overhang at both ends of the molecule, the length of the overhangs may be the same or different. In one embodiment, the interfering RNA molecule comprises 3' overhangs of about 1 to about 3 nucleotides on both ends of the molecule. In a further embodiment, the interfering RNA molecule is a double-stranded RNA having a 3' overhang of 2 nucleotides at both ends of the molecule. In yet another embodiment, the nucleotides comprising the overhang of the interfering RNA are TT dinucleotides or UU dinucleotides.

When determining the percentage identity of the interfering RNA molecule comprising one or more overhangs to the target mRNA sequence, the overhang(s) may or may not be taken into account. For example, the nucleotides from a 3' overhang and up to 2 nucleotides from the 5'- or 3'-terminus of the double strand may be modified without significant loss of activity of the small interfering RNA molecule.

The interfering RNA molecules can comprise one or more 5' or 3'-cap structures. The interfering RNA molecule can comprise a cap structure at the 3'-end of the sense strand, the antisense strand, or both the sense and antisense strands; or at the 5'-end of the sense strand, the antisense strand, or both the sense and antisense strands of the interfering RNA molecule. Alternatively, the interfering RNA molecule can comprise a cap structure at both the 3'-end and 5'-end of the interfering RNA molecule. The term "cap structure" refers to a chemical modification incorporated at either terminus of an oligonucleotide, which protects the molecule from exonuclease degradation, and may also facilitate delivery or localisation within a cell.

Another modification applicable to interfering RNA molecules is the chemical linkage to the interfering RNA molecule of one or more moieties or conjugates which enhance the activity, cellular distribution, cellular uptake, bioavailability or stability of the interfering RNA molecule. The polynucleotides may be synthesized or modified by methods well established in the art. Chemical modifications may include, but are not limited to 2' modifications, introduction of non-natural bases, covalent attachment to a ligand, and replacement of phosphate linkages with thiophosphate linkages. In this embodiment, the integrity of the duplex structure is strengthened by at least one, and typically two, chemical linkages. Chemical linking may be achieved by any of a variety of well-known techniques, for example by introducing covalent, ionic or hydrogen bonds; hydrophobic interactions, van der Waals or stacking interactions; by means of metal-ion coordination, or through use of purine analogues.

The nucleotides at one or both of the two single strands may be modified to modulate the activation of cellular enzymes, such as, for example, without limitation, certain nucleases. Techniques for reducing or inhibiting the activation of cellular enzymes are known in the art including, but not limited to, 2'-amino modifications, 2'-fluoro modifications, 2'-alkyl modifications, uncharged backbone modifications, morpholino modifications, 2'-O-methyl modifications, and phosphoramidate. Thus, at least one 2'-hydroxyl group of the nucleotides on a double-stranded RNA is replaced by a chemical group. Also, at least one nucleotide may be modified to form a locked nucleotide. Such locked nucleotide contains a methylene or ethylene bridge that connects the 2'-oxygen of ribose with the 4'-carbon of ribose. Introduction of a locked nucleotide into an oligonucleotide improves the affinity for complementary sequences and increases the melting temperature by several degrees.

Ligands may be conjugated to an interfering RNA molecule, for example, to enhance its cellular absorption. In certain embodiments, a hydrophobic ligand is conjugated to the molecule to facilitate direct permeation of the cellular membrane. These approaches have been used to facilitate cell permeation of antisense oligonucleotides. In certain instances, conjugation of a cationic ligand to oligonucleotides often results in improved resistance to nucleases. Representative examples of cationic ligands include propylammonium and dimethylpropylammonium. Anti-sense oligonucleotides can retain their high binding affinity to mRNA when the cationic ligand is dispersed throughout the oligonucleotide.

The molecules and polynucleotides described herein may be prepared using well-known techniques of solid-phase synthesis. Any other means for such synthesis known in the art may additionally or alternatively be employed.

Various embodiments are directed to expression vectors comprising one or more of the NtABA4 or NtNeSy or NtNCED2 polynucleotides or interfering RNA constructs that comprise one or more polynucleotides.

Various embodiments are directed to expression vectors comprising one or more of the NtABA4 or NtNeSy or NtNCED2 polynucleotides or one or more interfering RNA constructs.

Various embodiments are directed to expression vectors comprising one or more NtABA4 or NtNeSy or NtNCED2 polynucleotides or one or more interfering RNA constructs encoding one or more interfering RNA polynucleotides capable of self-annealing to form a hairpin structure, in which the construct comprises (a) one or more of the polynucleotides described herein; (b) a second sequence encoding a spacer element that forms a loop of the hairpin structure; and (c) a third sequence comprising a reverse complementary sequence of the first sequence, positioned in the same orientation as the first sequence, wherein the second sequence is positioned between the first sequence and the third sequence, and the second sequence is operably-linked to the first sequence and to the third sequence.

The disclosed sequences can be utilised for constructing various NtABA4 or NtNeSy or NtNCED2 polynucleotides that do not form hairpin structures. For example, a double-stranded RNA can be formed by (1) transcribing a first strand of the DNA by operably-linking to a first promoter, and (2) transcribing the reverse complementary sequence of the first strand of the DNA fragment by operably-linking to a second promoter. Each strand of the polynucleotide can be transcribed from the same expression vector, or from different expression vectors. The RNA duplex having RNA interference activity can be enzymatically converted to small interfering RNAs to modulate RNA levels.

Thus, various embodiments are directed to expression vectors comprising one or more NtABA4 or NtNeSy or NtNCED2 polynucleotide or interfering RNA constructs encoding interfering RNA polynucleotides capable of self-annealing, in which the construct comprises (a) one or more of the polynucleotides described herein; and (b) a second sequence comprising a complementary (for example, reverse complementary) sequence of the first sequence, positioned in the same orientation as the first sequence.

Various compositions and methods are provided for modulating the endogenous expression levels of one or more of the NtABA4 or NtNeSy or NtNCED2 polypeptides (or a combination of two or more or three or more thereof) by promoting co-suppression of gene expression. The phenomenon of co-suppression occurs as a result of introducing multiple copies of a transgene into a plant cell host. Integration of multiple copies of a transgene can result in modulated expression of the transgene and the targeted endogenous gene. The degree of co-suppression is dependent on the degree of sequence identity between the transgene and the targeted endogenous gene. The silencing of both the endogenous gene and the transgene can occur by extensive methylation of the silenced loci (that is, the endogenous promoter and endogenous gene of interest) that can preclude transcription. Alternatively, in some cases, co-suppression of the endogenous gene and the transgene can occur by post transcriptional gene silencing, in which transcripts can be produced but enhanced rates of degradation preclude accumulation of transcripts. The mechanism for co-suppression by post-transcriptional gene silencing is thought to resemble RNA interference, in that RNA seems to be both an important initiator and a target in these processes, and may be mediated at least in part by the same molecular machinery, possibly through RNA-guided degradation of mRNAs.

Co-suppression of nucleic acids can be achieved by integrating multiple copies of the nucleic acid or fragments thereof, as transgenes, into the genome of a plant of interest. The host plant can be transformed with an expression vector comprising a promoter operably-linked to the nucleic acid or fragments thereof. Various embodiments are directed to expression vectors for promoting co-suppression of endogenous genes comprising a promoter operably-linked to a polynucleotide.

Various embodiments are directed to methods for modulating the expression level of NtABA4 or NtNeSy or NtNCED2 polynucleotide(s) (or a combination of two or more or three or more thereof) by integrating multiple copies of the polynucleotide(s) into a (tobacco) plant genome, comprising: transforming a plant cell host with an expression vector that comprises a promoter operably-linked to a polynucleotide.

Various compositions and methods are provided for modulating the endogenous gene expression level by modulating the translation of mRNA. A host (tobacco) plant cell can be transformed with an expression vector comprising: a promoter operably-linked to a polynucleotide, positioned in anti-sense orientation with respect to the promoter to enable the expression of RNA polynucleotides having a sequence complementary to a portion of mRNA.

Various expression vectors for modulating the translation of mRNA may comprise: a promoter operably-linked to a polynucleotide in which the sequence is positioned in anti-sense orientation with respect to the promoter. The lengths of anti-sense RNA polynucleotides can vary, and may be from about 15-20 nucleotides, about 20-30 nucleotides, about 30-50 nucleotides, about 50-75 nucleotides, about 75-100 nucleotides, about 100-150 nucleotides, about 150-200 nucleotides, and about 200-300 nucleotides.

Methods for obtaining mutant polynucleotides and polypeptides are also provided. Any plant of interest, including a plant cell or plant material can be genetically modified by various methods known to induce mutagenesis, including site-directed mutagenesis, oligonucleotide-directed mutagenesis, chemically-induced mutagenesis, irradiation-induced mutagenesis, mutagenesis utilizing modified bases, mutagenesis utilizing gapped duplex DNA, double-strand break mutagenesis, mutagenesis utilizing repair-deficient host strains, mutagenesis by total gene synthesis, DNA shuffling and other equivalent methods.

Alternatively, genes can be targeted for inactivation by introducing transposons (for example, IS elements) into the genomes of plants of interest. These mobile genetic elements can be introduced by sexual cross-fertilization and insertion mutants can be screened for loss in protein activity. The disrupted gene in a parent plant can be introduced into other plants by crossing the parent plant with plant not subjected to transposon-induced mutagenesis by, for example, sexual cross-fertilization. Any standard breeding techniques known to persons skilled in the art can be utilized. In one embodiment, one or more genes can be inactivated by the insertion of one or more transposons. Mutations can result in homozygous disruption of one or more genes, in heterozygous disruption of one or more genes, or a combination of both homozygous and heterozygous disruptions if more than one gene is disrupted. Suitable transposable elements include retrotransposons, retroposons, and SINE-like elements. Such methods are known to persons skilled in the art.

Alternatively, genes can be targeted for inactivation by introducing ribozymes derived from a number of small circular RNAs that are capable of self-cleavage and replication in plants. These RNAs can replicate either alone (viroid RNAs) or with a helper virus (satellite RNAs). Examples of suitable RNAs include those derived from avocado sunblotch viroid and satellite RNAs derived from tobacco ringspot virus, lucerne transient streak virus, velvet tobacco mottle virus, *solanum* nodiflorum mottle virus, and subterranean clover mottle virus. Various target RNA-specific ribozymes are known to persons skilled in the art.

In some embodiments, the expression of a polypeptide is modulated by non-transgenic means, such as creating a mutation in a gene. Methods that introduce a mutation randomly in a gene sequence can include chemical mutagenesis, EMS mutagenesis and radiation mutagenesis. Methods that introduce one or more targeted mutations into a cell include but are not limited to genome editing technology, particularly zinc finger nuclease-mediated mutagenesis, tilling (targeting induced local lesions in genomes), homologous recombination, oligonucleotide-directed mutagenesis, and meganuclease-mediated mutagenesis.

Some non-limiting examples of mutations are deletions, insertions and missense mutations of at least one nucleotide, single nucleotide polymorphisms and a simple sequence repeat. After mutation, screening can be performed to identify mutations that create premature stop codons or otherwise non-functional genes. After mutation, screening can be performed to identify mutations that create functional genes that are capable of being expressed at elevated levels. Screening of mutants can be carried out by sequencing, or by the use of one or more probes or primers specific to the gene or protein. Specific mutations in polynucleotides can also be created that can result in modulated gene expression, modulated stability of mRNA, or modulated stability of protein. Such plants are referred to herein as "non-naturally occurring" or "mutant" plants. Typically, the mutant or non-naturally occurring plants will include at least a portion of foreign or synthetic or man-made nucleic acid (for example, DNA or RNA) that was not present in the plant before it was manipulated. The foreign nucleic acid may be a single nucleotide, two or more nucleotides, two or more contiguous nucleotides or two or more non-contiguous nucleotides—such as at least 10, 20, 30, 40, 50, 100, 200, 300, 400, 500, 600, 700, 800, 900, 1000, 1100, 1200, 1300, 1400 or 1500 or more contiguous or non-contiguous nucleotides.

The mutant or non-naturally occurring plants can have any combination of one or more mutations which results in modulated protein levels. For example, the mutant or non-naturally occurring plants may have a single mutation in a single gene; multiple mutations in a single gene; a single mutation in two or more or three or more genes; or multiple mutations in two or more or three or more genes. By way of further example, the mutant or non-naturally occurring plants may have one or more mutations in a specific portion of the gene(s)—such as in a region of the gene that encodes an active site of the protein or a portion thereof. By way of further example, the mutant or non-naturally occurring plants may have one or more mutations in a region outside of one or more gene(s)—such as in a region upstream or downstream of the gene it regulates provided that they modulate the activity or expression of the gene(s). Upstream elements can include promoters, enhancers or transcription factors. Some elements—such as enhancers—can be positioned upstream or downstream of the gene it regulates. The element(s) need not be located near to the gene that it regulates since some elements have been found located several hundred thousand base pairs upstream or downstream of the gene that it regulates. The mutant or non-naturally occurring plants may have one or more mutations located within the first 100 nucleotides of the gene(s), within the first 200 nucleotides of the gene(s), within the first 300 nucleotides of the gene(s), within the first 400 nucleotides of the gene(s), within the first 500 nucleotides of the gene(s), within the first 600 nucleotides of the gene(s), within the first 700 nucleotides of the gene(s), within the first 800 nucleotides of the gene(s), within the first 900 nucleotides of the gene(s), within the first 1000 nucleotides of the gene(s), within the first 1100 nucleotides of the gene(s), within the first 1200 nucleotides of the gene(s), within the first 1300 nucleotides of the gene(s), within the first 1400 nucleotides of the gene(s) or within the first 1500 nucleotides of the gene(s). The mutant or non-naturally occurring plants may have one or more mutations located within the first, second, third, fourth, fifth, sixth, seventh, eighth, ninth, tenth, eleventh, twelfth, thirteenth, fourteenth or fifteenth set of 100 nucleotides of the gene(s) or combinations thereof. Mutant or non-naturally occurring plants (for example, mutant, non-naturally occurring or transgenic plants and the like, as described herein) comprising the mutant polypeptide variants are disclosed.

In one embodiment, seeds from plants are mutagenised and then grown into first generation mutant plants. The first generation plants are then allowed to self-pollinate and seeds from the first generation plant are grown into second generation plants, which are then screened for mutations in their loci. Though the mutagenized plant material can be screened for mutations, an advantage of screening the second generation plants is that all somatic mutations correspond to germline mutations. One of skill in the art would understand that a variety of plant materials, including but not limited to, seeds, pollen, plant tissue or plant cells, may be mutagenised in order to create the mutant plants. However, the type of plant material mutagenised may affect when the plant nucleic acid is screened for mutations. For example, when pollen is subjected to mutagenesis prior to pollination of a non-mutagenized plant the seeds resulting from that pollination are grown into first generation plants. Every cell of the first generation plants will contain mutations created in the pollen; thus these first generation plants may then be screened for mutations instead of waiting until the second generation.

Mutagens that create primarily point mutations and short deletions, insertions, transversions, and or transitions, including chemical mutagens or radiation, may be used to create the mutations. Mutagens include, but are not limited to, ethyl methanesulfonate, methylmethane sulfonate, N-ethyl-N-nitrosurea, triethylmelamine, N-methyl-N-nitrosourea, procarbazine, chlorambucil, cyclophosphamide, diethyl sulfate, acrylamide monomer, melphalan, nitrogen mustard, vincristine, dimethylnitrosamine, N-methyl-N'-nitro-Nitrosoguanidine, nitrosoguanidine, 2-aminopurine, 7,12 dimethyl-benz(a)anthracene, ethylene oxide, hexamethylphosphoramide, bisulfan, diepoxyalkanes (diepoxyoctane, diepoxybutane, and the like), 2-methoxy-6-chloro-9[3-(ethyl-2-chloro-ethyl)aminopropylamino]acridine dihydrochloride and formaldehyde.

Spontaneous mutations in the locus that may not have been directly caused by the mutagen are also contemplated provided that they result in the desired phenotype. Suitable mutagenic agents can also include, for example, ionising radiation—such as X-rays, gamma rays, fast neutron irradiation and UV radiation. Any method of plant nucleic acid preparation known to those of skill in the art may be used to prepare the plant nucleic acid for mutation screening.

Prepared nucleic acid from individual plants, plant cells, or plant material can optionally be pooled in order to expedite screening for mutations in the population of plants originating from the mutagenized plant tissue, cells or material. One or more subsequent generations of plants, plant cells or plant material can be screened. The size of the optionally pooled group is dependent upon the sensitivity of the screening method used.

After the nucleic acid samples are optionally pooled, they can be subjected to polynucleotide-specific amplification techniques, such as Polymerase Chain Reaction. Any one or more primers or probes specific to the gene or the sequences immediately adjacent to the gene may be utilized to amplify the sequences within the optionally pooled nucleic acid sample. Exemplary primers are set forth in SEQ ID Nos: 3 to 5, 10 to 12 and 14 to 16. Preferably, the one or more primers or probes are designed to amplify the regions of the locus where useful mutations are most likely to arise. Most preferably, the primer is designed to detect mutations within regions of the polynucleotide. Additionally, it is preferable for the primer(s) and probe(s) to avoid known polymorphic sites in order to ease screening for point mutations. To facilitate detection of amplification products, the one or more primers or probes may be labelled using any conventional labelling method. Primer(s) or probe(s) can be designed based upon the sequences described herein using methods that are well understood in the art.

To facilitate detection of amplification products, the primer(s) or probe(s) may be labelled using any conventional labelling method. These can be designed based upon the sequences described herein using methods that are well understood in the art.

Polymorphisms may be identified by means known in the art and some have been described in the literature.

In a further aspect there is provided a method of preparing a mutant plant. The method involves providing at least one cell of a plant comprising a gene encoding a functional NtABA4 or NtNeSy or NtNCED2 polynucleotide (or a combination of two or more or three or more thereof). Next, the at least one cell of the plant is treated under conditions effective to modulate the activity of the NtABA4 or NtNeSy or NtNCED2 polynucleotide. The at least one mutant plant cell is then propagated into a mutant plant, where the mutant plant has a modulated level of NtABA4 or NtNeSy or NtNCED2 polypeptides (or a combination of two or more or three or more thereof) as compared to that of a control plant. In one embodiment of this method of making a mutant plant, the treating step involves subjecting the at least one cell to a chemical mutagenizing agent as described above and under conditions effective to yield at least one mutant plant cell. In another embodiment of this method, the treating step involves subjecting the at least one cell to a radiation source under conditions effective to yield at least one mutant plant cell. The term "mutant plant" includes mutants plants in which the genotype is modified as compared to a control plant, suitably by means other than genetic engineering or genetic modification.

In certain embodiments, the mutant plant, mutant plant cell or mutant plant material may comprise one or more mutations that have occurred naturally in another plant, plant cell or plant material and confer a desired trait. This mutation can be incorporated (for example, introgressed) into another plant, plant cell or plant material (for example, a plant, plant cell or plant material with a different genetic background to the plant from which the mutation was derived) to confer the trait thereto. Thus by way of example, a mutation that occurred naturally in a first plant may be introduced into a second plant—such as a second plant with a different genetic background to the first plant. The skilled person is therefore able to search for and identify a plant carrying naturally in its genome one or more mutant alleles of the genes described herein which confer a desired trait. The mutant allele(s) that occurs naturally can be transferred to the second plant by various methods including breeding, backcrossing and introgression to produce a lines, varieties or hybrids that have one or more mutations in the genes described herein. Plants showing a desired trait may be screened out of a pool of mutant plants. Suitably, the selection is carried out utilising the knowledge of the nucleotide sequences as described herein. Consequently, it is possible to screen for a genetic trait as compared to a control. Such a screening approach may involve the application of conventional nucleic acid amplification and/or hybridization techniques as discussed herein. Thus, a further aspect of the present invention relates to a method for identifying a mutant plant comprising the steps of: (a) providing a sample comprising a NtABA4 or NtNeSy or NtNCED2 polynucleotide from a plant; and (b) determining the nucleic acid sequence of the polynucleotide, wherein a difference in the sequence of the NtABA4 or NtNeSy or NtNCED2 polynucleotide as compared to the polynucleotide sequence of a control plant is indicative that said plant is a NtABA4 or NtNeSy or NtNCED2 mutant plant. In another aspect there is provided a method for identifying a mutant plant which accumulates increased levels of either (i) carotenoid or beta-damascenone; or (ii) carotenoid and beta-damascenone, as compared to a control plant comprising the steps of: (a) providing a sample from a plant to be screened; (b) determining if said sample comprises one or more mutations in the NtABA4 or NtNeSy or NtNCED2 polynucleotide; and (c) determining the (i) carotenoid or beta-damascenone; or (ii) carotenoid and beta-damascenone content of said plant; wherein if said sample comprises one or more mutations in the NtABA4 or NtNeSy or NtNCED2 polynucleotide that modulate the expression or the activity of the protein encoded as compared to a control plant and a part of the tobacco plant has an increase in either (i) carotenoid or beta-damascenone; or (ii) carotenoid and beta-damascenone of at least 5% as compared to a control tobacco plant in which the expression or the activity of NtABA4 or NtNeSy or NtNCED2 has not been modulated is indicative of a mutant plant which accumulates increased levels of either (i) carotenoid or beta-damascenone; or (ii) carotenoid and beta-damascenone. In another aspect there is provided a method for preparing a mutant plant which accumulates increased levels of either (i) carotenoid or beta-damascenone; or (ii) carotenoid and beta-damascenone, as compared to a control plant comprising the steps of: (a) providing a sample from a first plant; (b) determining if said sample comprises one or more mutations in the NtABA4 or NtNeSy or NtNCED2 polynucleotide that result in the accumulation of increased levels of either (i) carotenoid or beta-damascenone; or (ii) carotenoid and beta-damascenone; and (c) transferring the one or more mutations into a second plant. The mutation(s) can be transferred into the second plant using various methods that are known in the art—such as by genetic engineering, genetic manipulation, introgression, plant breeding, backcrossing and the like. In one embodiment, the first plant is a naturally occurring plant. In one embodiment, the second plant has a different genetic background to the first plant. In another aspect there is provided a method for preparing a mutant plant which accumulates increased levels of either (i) carotenoid or beta-damascenone; or (ii) carotenoid and beta-damascenone, as compared to a control plant comprising the steps of: (a) providing a sample from a first plant; (b) determining if said sample comprises one or more mutations in the NtABA4 or NtNeSy or NtNCED2 polynucleotide that results in the accumulation of increased levels of either (i) carotenoid or beta-damascenone; or (ii) carotenoid and beta-damascenone; and (c) introgressing the one or more mutations from the first plant into a second plant. In one embodiment, the step of introgressing comprises plant breeding, optionally including backcrossing and the like. In one embodiment, the first plant is a naturally occurring plant. In one embodiment, the second plant has a different genetic background to the first plant. In one embodiment, the first plant is not a cultivar or an elite cultivar. In one embodiment, the second plant is a cultivar or an elite cultivar. A further aspect relates to a mutant plant (including a cultivar or elite cultivar mutant plant) obtained or obtainable by the methods described herein. In certain embodiments, the "mutant plants" may have one or more mutations localised only to a specific region of the plant—such as within the sequence of the NtABA4 or NtNeSy or NtNCED2 polynucleotide(s). According to this embodiment, the remaining genomic sequence of the mutant plant will be the same or substantially the same as the plant prior to the mutagenesis.

In certain embodiments, the mutant plants may have one or more mutations localised in more than one region of the plant—such as within the sequence of the NtABA4 or NtNeSy or NtNCED2 polynucleotide and in one or more further regions of the genome. According to this embodiment, the remaining genomic sequence of the mutant plant will not be the same or will not be substantially the same as the plant prior to the mutagenesis. In certain embodiments, the mutant plants may not have one or more mutations in one or more, two or more, three or more, four or more or five or more exons of the NtABA4 or NtNeSy or NtNCED2 polynucleotide; or may not have one or more mutations in one or more, two or more, three or more, four or more or five or more introns of the NtABA4 or NtNeSy or NtNCED2 polynucleotide; or may not have one or more mutations in a promoter of the NtABA4 or NtNeSy or NtNCED2 polynucleotide; or may not have one or more mutations in the 3' untranslated region of the NtABA4 or NtNeSy or NtNCED2 polynucleotide; or may not have one or more mutations in the 5' untranslated region of the NtABA4 or NtNeSy or NtNCED2 polynucleotide; or may not have one or more mutations in the coding region of the NtABA4 or NtNeSy or NtNCED2 polynucleotide; or may not have one or more mutations in the non-coding region of the NtABA4 or NtNeSy or NtNCED2 polynucleotide; or any combination of two or more, three or more, four or more, five or more; or six or more thereof parts thereof.

In a further aspect there is provided a method of identifying a plant, a plant cell or plant material comprising a mutation in a gene encoding NtABA4 or NtNeSy or NtNCED2 comprising: (a) subjecting a plant, a plant cell or plant material to mutagenesis; (b) obtaining a nucleic acid sample from said plant, plant cell or plant material or descendants thereof; and (c) determining the nucleic acid sequence of the gene encoding NtABA4 or NtNeSy or NtNCED2 or a variant or a fragment thereof, wherein a difference in said sequence is indicative of one or more mutations therein. Zinc finger proteins can be used to modulate the expression or the activity of one or more of the NtABA4 or NtNeSy or NtNCED2 polynucleotides described herein. In various embodiments, a genomic DNA sequence comprising a part of or all of the coding sequence of the polynucleotide is modified by zinc finger nuclease-mediated mutagenesis. The genomic DNA sequence is searched for a unique site for zinc finger protein binding. Alternatively, the genomic DNA sequence is searched for two unique sites for zinc finger protein binding wherein both sites are on opposite strands and close together, for example, 1, 2, 3, 4, 5, 6 or more basepairs apart. Accordingly, zinc finger proteins that bind to polynucleotides are provided.

A zinc finger protein may be engineered to recognize a selected target site in a gene. A zinc finger protein can comprise any combination of motifs derived from natural zinc finger DNA-binding domains and non-natural zinc finger DNA-binding domains by truncation or expansion or a process of site-directed mutagenesis coupled to a selection method such as, but not limited to, phage display selection, bacterial two-hybrid selection or bacterial one-hybrid selection. The term "non-natural zinc finger DNA-binding domain" refers to a zinc finger DNA-binding domain that binds a three-basepair sequence within the target nucleic acid and that does not occur in the cell or organism comprising the nucleic acid which is to be modified. Methods for the design of zinc finger protein which binds specific nucleotide sequences which are unique to a target gene are known in the art.

A zinc finger nuclease may be constructed by making a fusion of a first polynucleotide coding for a zinc finger protein that binds to a polynucleotide, and a second polynucleotide coding for a non-specific endonuclease such as, but not limited to, those of a Type IIS endonuclease. A fusion protein between a zinc finger protein and the nuclease may comprise a spacer consisting of two basepairs or alternatively, the spacer can consist of three, four, five, six, seven or more basepairs. In various embodiments, a zinc finger nuclease introduces a double stranded break in a regulatory region, a coding region, or a non-coding region of a genomic DNA sequence of a polynucleotide and leads to a reduction of the level of expression of a polynucleotide, or a reduction in the activity of the protein encoded thereby. Cleavage by zinc finger nucleases frequently results in the deletion of DNA at the cleavage site following DNA repair by non-homologous end joining.

In other embodiments, a zinc finger protein may be selected to bind to a regulatory sequence of a polynucleotide. More specifically, the regulatory sequence may comprise a transcription initiation site, a start codon, a region of an exon, a boundary of an exon-intron, a terminator, or a stop codon. Accordingly, the invention provides a mutant, non-naturally occurring or transgenic plant or plant cells, produced by zinc finger nuclease-mediated mutagenesis in the vicinity of or within one or more polynucleotides described herein, and methods for making such a plant or plant cell by zinc finger nuclease-mediated mutagenesis. Methods for delivering zinc finger protein and zinc finger nuclease to a tobacco plant are similar to those described below for delivery of meganuclease.

In another aspect, methods for producing mutant, non-naturally occurring or transgenic or otherwise genetically-modified plants using meganucleases, such as I-CreI, are described. Naturally occurring meganucleases as well as recombinant meganucleases can be used to specifically cause a double-stranded break at a single site or at relatively few sites in the genomic DNA of a plant to allow for the disruption of one or more polynucleotides described herein. The meganuclease may be an engineered meganuclease with altered DNA-recognition properties. Meganuclease proteins can be delivered into plant cells by a variety of different mechanisms known in the art.

The inventions encompass the use of meganucleases to inactivate a NtABA4 or NtNeSy or NtNCED2 polynucleotide(s) (or a combination of two or more or three or more thereof) in a plant cell or plant. Particularly, the inventions provide a method for inactivating a polynucleotide in a plant using a meganuclease comprising: a) providing a plant cell comprising a polynucleotide as described herein; (b) introducing a meganuclease or a construct encoding a meganuclease into said plant cell; and (c) allowing the meganuclease to substantially inactivate the polynucleotide(s) Meganucleases can be used to cleave meganuclease recognition sites within the coding regions of a polynucleotide. Such cleavage frequently results in the deletion of DNA at the meganuclease recognition site following mutagenic DNA repair by non-homologous end joining. Such mutations in the gene coding sequence are typically sufficient to inactivate the gene. This method to modify a plant cell involves, first, the delivery of a meganuclease expression cassette to a plant cell using a suitable transformation method. For highest efficiency, it is desirable to link the meganuclease expression cassette to a selectable marker and select for successfully transformed cells in the presence of a selection agent. This approach will result in the integration of the meganuclease expression cassette into the genome, however, which may not be desirable if the plant is likely to require regulatory approval. In such cases, the meganuclease expression cassette (and linked selectable marker gene) may be segregated away in subsequent plant generations using conventional breeding techniques. Alternatively, plant cells may be initially be transformed with a meganuclease expression cassette lacking a selectable marker and may be grown on media lacking a selection agent. Under such conditions, a fraction of the treated cells will acquire the meganuclease expression cassette and will express the engineered meganuclease transiently without integrating the meganuclease expression cassette into the genome. Because it does not account for transformation efficiency, this latter transformation procedure requires that a greater number of treated cells be screened to obtain the desired genome modification. The above approach can also be applied to modify a plant cell when using a zinc finger protein or zinc finger nuclease.

Following delivery of the meganuclease expression cassette, plant cells are grown, initially, under conditions that are typical for the particular transformation procedure that was used. This may mean growing transformed cells on media at temperatures below 26° C., frequently in the dark. Such standard conditions can be used for a period of time, preferably 1-4 days, to allow the plant cell to recover from the transformation process. At any point following this initial recovery period, growth temperature may be raised to stimulate the activity of the engineered meganuclease to cleave and mutate the meganuclease recognition site.

For certain applications, it may be desirable to precisely remove the polynucleotide from the genome of the plant. Such applications are possible using a pair of engineered meganucleases, each of which cleaves a meganuclease recognition site on either side of the intended deletion. TAL Effector Nucleases (TALENs) that are able to recognize and bind to a gene and introduce a double-strand break into the genome can also be used. Thus, in another aspect, methods for producing mutant, non-naturally occurring or transgenic or otherwise genetically-modified plants as described herein using TAL Effector Nucleases are contemplated.

Plants suitable for use in genetic modification include, but are not limited to, monocotyledonous and dicotyledonous plants and plant cell systems, including species from one of the following families: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

Suitable species may include members of the genera *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Cit-*

*rullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis*, and *Zea*.

Suitable species may include *Panicum* spp., *Sorghum* spp., *Miscanthus* spp., *Saccharum* spp., *Erianthus* spp., *Populus* spp., *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cord-grass), *Medicago sativa* (alfalfa), *Arundo donax* (giant reed), *Secale cereale* (rye), *Salix* spp. (willow), *Eucalyptus* spp. (*eucalyptus*), Triticosecale (tritic wheat times rye), bamboo, *Helianthus annuus* (sunflower), *Carthamus tinctorius* (safflower), *Jatropha curcas* (jatropha), *Ricinus communis* (castor), *Elaeis guineensis* (palm), *Linum usitatissimum* (flax), *Brassica juncea, Beta vulgaris* (sugarbeet), *Manihot esculenta* (cassava), *Lycopersicon esculentum* (tomato), *Lactuca sativa* (lettuce), *Musyclise alca* (banana), *Solanum tuberosum* (potato), *Brassica oleracea* (broccoli, cauliflower, Brussels sprouts), *Camellia sinensis* (tea), *Fragaria ananassa* (strawberry), *Theobroma cacao* (cocoa), *Coffe ycliseca* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), *Solanum melongena* (eggplant), *Rosa* spp. (rose), *Dianthus caryophyllus* (carnation), *Petunia* spp. (*petunia*), *Poinsettia pulcherrima* (poinsettia), *Lupinus albus* (lupin), *Uniola paniculata* (oats), bentgrass (*Agrostis* spp.), *Populus tremuloides* (aspen), *Pinus* spp. (pine), *Abies* spp. (fir), *Acer* spp. (maple), *Hordeum vulgare* (barley), *Poa pratensis* (bluegrass), *Lolium* spp. (ryegrass) and *Phleum pratense* (timothy), *Panicum virgatum* (switchgrass), *Sorghu yclise* or (*sorghum*, sudangrass), *Miscanthus giganteus* (*miscanthus*), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet).

Various embodiments are directed to mutant tobacco plants, non-naturally occurring tobacco plants or transgenic tobacco plants modified to modulate gene expression levels thereby producing plants—such as tobacco plan—in which the expression level of a polypeptide is modulated within plant tissues of interest as compared to a control plant. The disclosed compositions and methods can be applied to any species of the genus *Nicotiana*, including *N. rustica* and *N. tabacum* (for example, LA B21, LN KY171, TI 1406, Basma, Galpao, Perique, Beinhart 1000-1, and Petico). Other species include *N. acaulis, N. yclise ta, N. yclise ta* var. *multiflora, N. yclise na, N. alata, N. amplexicaulis, N. arentsii, N yclise ta, N. benavidesii, N. benthamiana, N. bigelovii, N. bonariensis, N. cavicola, N. clevelandii, N. cordifolia, N. corymbosa, N. debneyi, N. excelsior, N. forgetiana, N. fragrans, N. glauca, N. glutinosa, N. goodspeedii, N. gossei, N. hybrid, N. ingulba, N. kawakamii, N. knightiana, N. langsdorffii, N. linearis, N. longiflora, N yclise ma, N. megalosiphon, N. miersii, N. noctiflora, N. nudicaulis, N. obtusifolia, N. occidentalis, N. occidentalis* subsp. *hesperis, N. otophora, N. paniculata, N. pauciflora, N. petunioides, N. plumbaginifolia, N. quadrivalvis, N. raimondii, N. repanda, N. rosulata, N. rosulata* subsp. *ingulba, N. rotundifolia, N. setchellii, N. simulans, N. solanifolia, N. spegazzinii, N. stocktonii, N. suaveolens, N. sylvestris, N. thyrsiflora, N. tomentosa, N. tomentosiformis, N. trigonophylla, N. umbratica, N. yclise ta, N. velutina, N. wigandioides*, and *N. x sanderae*.

The use of tobacco cultivars and elite tobacco cultivars is also contemplated herein. The transgenic, non-naturally occurring or mutant plant may therefore be a tobacco variety or elite tobacco cultivar that comprises one or more transgenes, or one or more genetic mutations or a combination thereof. The genetic mutation(s) (for example, one or more polymorphisms) can be mutations that do not exist naturally in the individual tobacco variety or tobacco cultivar (for example, elite tobacco cultivar) or can be genetic mutation(s) that do occur naturally provided that the mutation does not occur naturally in the individual tobacco variety or tobacco cultivar (for example, elite tobacco cultivar).

Particularly useful *Nicotiana tabacum* varieties include Burley type, dark type, flue-cured type, and Oriental type tobaccos. Non-limiting examples of varieties or cultivars are: BD 64, CC 101, CC 200, CC 27, CC 301, CC 400, CC 500, CC 600, CC 700, CC 800, CC 900, Coker 176, Coker 319, Coker 371 Gold, Coker 48, CD 263, DF911, DT 538 LC Galpao tobacco, GL 26H, GL 350, GL 600, GL 737, GL 939, GL 973, HB 04P, HB 04P LC, HB3307PLC, Hybrid 403LC, Hybrid 404LC, Hybrid 501 LC, K 149, K 326, K 346, K 358, K394, K 399, K 730, KDH 959, KT 200, KT204LC, KY10, KY14, KY 160, KY 17, KY 171, KY 907, KY907LC, KTY14xL8 LC, Little Crittenden, McNair 373, McNair 944, msKY 14xL8, Narrow Leaf Madole, Narrow Leaf Madole LC, NBH 98, N-126, N-777LC, N-7371LC, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, PD 7302 LC, PD 7309 LC, PD 7312 LC' 'Periq'e' tobacco, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN 97, TN97LC, TN D94, TN D950, TR (Tom Rosson) Madole, VA 309, VA359, AA 37-1, B 13P, Xanthi (Mitchell-Mor), Bel-W3, 79-615, Samsun Holmes NN, KTRDC number 2 Hybrid 49, Burley 21, KY 8959, KY 9, MD 609, PG 01, PG 04, PO1, PO2, PO3, RG 11, RG 8, VA 509, AS44, Banket A1, Basma Drama B84/31, Basma I Zichna ZP4/B, Basma Xanthi BX 2A, Batek, Besuki Jember, C104, Coker 347, Criollo Misionero, Delcrest, Djebel 81, DVH 405, Galpão Comum, HB04P, Hicks Broadleaf, Kabakulak Elassona, Kutsage E1, LA BU 21, NC 2326, NC 297, PVH 2110, Red Russian, Samsun, Saplak, Simmaba, Talgar 28, Wislica, Yayaldag, Prilep HC-72, Prilep P23, Prilep PB 156/1, Prilep P12-2/1, Yaka JK-48, Yaka JB 125/3, TI-1068, KDH-960, TI-1070, TW136, Basma, TKF 4028, L8, TKF 2002, GR141, Basma xanthi, GR149, GR153, Petit Havana. Low converter subvarieties of the above, even if not specifically identified herein, are also contemplated.

Embodiments are also directed to compositions and methods for producing mutant plants, non-naturally occurring plants, hybrid plants, or transgenic plants that have been modified to modulate the expression or activity of a NtABA4 or NtNeSy or NtNCED2 polynucleotide (or a combination of two or more or three or more thereof) or a NtABA4 or NtNeSy or NtNCED2 polypeptide (or a combination of two or more or three or more thereof). Advantageously, the mutant plants, non-naturally occurring plants, hybrid plants, or transgenic plants that are obtained may be similar or substantially the same in overall appearance to control plants. Various phenotypic characteristics such as degree of maturity, number of leaves per plant, stalk height, leaf insertion angle, leaf size (width and length), internode distance, and lamina-midrib ratio can be assessed by field observations.

One aspect relates to a seed of a mutant plant, a non-naturally occurring plant, a hybrid plant or a transgenic plant described herein. Preferably, the seed is a tobacco seed. A further aspect relates to pollen or an ovule of a mutant plant, a non-naturally occurring plant, a hybrid plant or a transgenic plant that is described herein. In addition, there is provided a mutant plant, a non-naturally occurring plant, a hybrid plant or a transgenic plant as described herein which further comprises a nucleic acid conferring male sterility.

Also provided is a tissue culture of regenerable cells of the mutant plant, non-naturally occurring plant, hybrid plant, or transgenic plant or a part thereof as described herein, which culture regenerates plants capable of expressing all the morphological and physiological characteristics of the parent. The regenerable cells include but are not limited to cells from leaves, pollen, embryos, cotyledons, hypocotyls, roots, root tips, anthers, flowers and a part thereof, ovules, shoots, stems, stalks, pith and capsules or callus or protoplasts derived therefrom.

One object is to provide mutant, transgenic or non-naturally occurring plants that exhibit modulated carotenoid or beta-damascenone levels or modulated carotenoid and beta-damascenone levels whilst maintaining substantially the same visual appearance as compared to a control plant. Accordingly, there is described herein mutant, transgenic or non-naturally occurring plants or plant cells that have modulated levels of carotenoid or beta-damascenone levels or modulated levels of carotenoid and beta-damascenone levels as compared to control cells or control plants. The mutant, transgenic or non-naturally occurring plants or plant cells have been modified to modulate the synthesis or activity of one or more of the enzymes described herein by modulating the expression of one or more polypeptides encoding the polynucleotide sequences described herein.

A further aspect, relates to a mutant, non-naturally occurring or transgenic plant or cell, wherein the expression of or the activity of one or more of the enzymes described herein is modulated and a part of the plant (for example, the leaves) has an increase or a decrease in carotenoid levels of at least 5% as compared to a control plant in which the expression or the activity said enzyme(s) has not been modulated. A still further aspect, relates to a mutant, non-naturally occurring or transgenic plant or cell, wherein expression of neoxanthin synthase or the activity of the protein encoded thereby is modulated and wherein the beta-damascenone levels in aerosol is increased or decreased by at least 5% as compared to the aerosol from the control plant.

The change in the carotenoid content as compared to the control plant may be a change of at least about 5%, at least about 10%, at least about 20%, at least about 25%, at least about 30%, at least about 40%, at least about 50%, at least about 60%, at least about 70%, at least about 75%, at least about 80%, at least about 90%, at least about 95%, at least about 96%, at least about 97%, at least about 98%, at least about 99%, or about 100% or more-such as 200% or 300% or more The change in the beta-damascenone content as compared to the control plant may be a change of at least about 5%, at least about 10%, at least about 20%, at least about 25%, at least about 30%, at least about 40%, at least about 50%, at least about 60%, at least about 70%, at least about 75%, at least about 80%, at least about 90%, at least about 95%, at least about 96%, at least about 97%, at least about 98%, at least about 99%, or about 100% or more—such as 200% or 300% or more.

Suitably, the lutein content in part of the plant (for example, the leaves) is at least about 18 mg/100 g, suitably, at least about 18.5 mg/100 g, suitably, at least about 19 mg/100 g, suitably, at least about 19.5 mg/100 g, suitably, at least about 20 mg/100 g, suitably, at least about 25 mg/100 g or more.

Suitably, the beta-carotene content in part of the plant (for example, the leaves) is at least about 11.5 mg/100 g of harvested plant (for example, leaf) material, suitably, at least about 12 mg/100 g, suitably, at least about 12.5 mg/100 g, suitably, at least about 13 mg/100 g, suitably, at least about 13.5 mg/100 g, suitably, at least 14 mg/100 g, suitably, at least about 14.5 mg/100 g, or suitably, at least about 15 mg/100 g, or more.

Suitably, the lutein content in part of the plant (for example, the leaves) is at least about 18 mg/100 g of harvested plant (for example, leaf) material, suitably, at least about 18.5 mg/100 g, suitably, at least about 19 mg/100 g, suitably, at least about 19.5 mg/100 g, suitably, at least about 20 mg/100 g, suitably, at least about 25 mg/100 g or more and the beta-carotene content in part of the plant (for example, the leaves) is at least about 11.5 mg/100 g, suitably, at least about 12 mg/100 g, suitably, at least about 12.5 mg/100 g, suitably, at least about 13 mg/100 g, suitably, at least about 13.5 mg/100 g, suitably, at least 14 mg/100 g, suitably, at least about 14.5 mg/100 g, or suitably, at least about 15 mg/100 g, or more.

Suitably, the beta-damascenone levels in aerosol of burnt or heated leaves is at least about 1 ng/mg of burnt or harvested plant (for example, leaf) material, suitably, at least about 1.05 ng/mg, suitably, at least about 1.1 ng/mg, suitably, at least about 1.15 ng/mg, or suitably, at least about 2 ng/mg or more.

Suitably, (i) the lutein content in part of the plant (for example, the leaves) is at least about 18 mg/100 g of harvested plant (for example, leaf) material, suitably, at least about 18.5 mg/100 g, suitably, at least about 19 mg/100 g, suitably, at least about 19.5 mg/100 g, suitably, at least about 20 mg/100 g; suitably, at least about 25 mg/100 g or more; suitably, (ii) the beta-carotene content in part of the plant (for example, the leaves) is at least about 11.5 mg/100 g of harvested plant (for example, leaf) material, suitably, at least about 12 mg/100 g, suitably, at least about 12.5 mg/100 g, suitably, at least about 13 mg/100 g, suitably, at least about 13.5 mg/100 g, suitably, at least 14 mg/100 g, suitably, at least about 14.5 mg/100 g, or suitably, at least about 15 mg/100 g, or more; and (iii) suitably, the beta-damascenone levels in aerosol of burnt or heated leaves is at least about 1 ng/mg of burnt or harvested plant (for example, leaf) material, suitably, at least about 1.05 ng/mg, suitably, at least about 1.1 ng/mg, suitably, at least about 1.15 ng/mg, or suitably, at least about 2 ng/mg or more.

The plant may be heated to 100° C. or above—such as at least 125° C., at least 150° C., at least 175° C. or at least 200°—to release the aerosol.

In a still further aspect, there is provided a mutant, non-naturally occurring or transgenic plant, wherein expression of an enzyme selected from the group consisting of neoxanthin synthase, lycopene beta cyclase and 9-cis-epoxycarotenoid dioxygenase or a combination of two or more or three or more thereof (said combinations are disclosed herein) or the activity of the protein encoded thereby is increased and (i) the lutein content in part of the plant (for example, the leaves) is at least about 18 mg/100 g of harvested plant (for example, leaf) material; (ii) the beta-carotene content in part of the plant (for example, the leaves) is at least about 11.5 mg/100 g of harvested plant (for example, leaf) material; and (iii) the beta-damascenone levels in aerosol of burnt or heated leaves is at least about 1 ng/mg of burnt or harvested plant (for example, leaf) material. Suitably the visual appearance of said plant is substantially the same as the control plant. Suitably, the plant is a tobacco plant.

Embodiments are also directed to compositions and methods for producing mutant, non-naturally occurring or transgenic plants that have been modified to modulate neoxanthin synthase expression or activity; or lycopene beta cyclase expression or activity; or 9-cis-epoxycarotenoid dioxygenase expression activity which can result in plants or plant components (for example, leaves—such as green leaves or cured leaves) with modulated levels of carotenoids (for example, but not limited to, lutein or beta-carotene or both) as compared to a control. Embodiments are also directed to compositions and methods for producing mutant, non-naturally occurring or transgenic plants that have been modified to modulate the expression or activity of a combination of two or more or three or more of neoxanthin synthase, lycopene beta cyclase and 9-cis-epoxycarotenoid dioxygenase. Thus one embodiment relates to modulating the expression or activity of neoxanthin synthase, lycopene beta cyclase and 9-cis-epoxycarotenoid dioxygenase; another embodiment, relates to modulating the expression or activity of neoxanthin synthase and lycopene beta cyclase; another embodiment relates to modulating the expression or activity of neoxanthin synthase and 9-cis-epoxycarotenoid dioxygenase; and another embodiment relates to modulating the expression or activity of lycopene beta cyclase and 9-cis-epoxycarotenoid dioxygenase or any other combination of these two or more sequences. Modulating the levels of carotenoids in plants may have nutritional benefits to the consumer, especially when the carotenoid levels in the plant are increased. Modulating the levels of carotenoids in plants may be used to generate plants that are resistant to herbicides that inhibit carotenoid biosynthesis, especially when the carotenoid levels in the plant are increased. Thus, in one specific embodiment, compositions and methods for producing mutant, non-naturally occurring or transgenic plants that have been modified to increase the expression or activity of the above-mentioned polynucleotides and combinations thereof are provided which can result in plants or plant components (for example, leaves—such as green leaves or cured leaves) with improved nutritional benefits or increased resistance to herbicides.

Embodiments are also directed to compositions and methods for producing mutant, non-naturally occurring or transgenic plants that have been modified to modulate neoxanthin synthase expression or activity which can result in plants or plant components (for example, heated cured leaves) with modulated levels of beta-damascenone as compared to a control. Thus, in a further embodiment, compositions and methods for producing mutant, non-naturally occurring or transgenic plants that have been modified to modulate neoxanthin synthase expression or activity are provided which can result in plants or plant material—such as heated or burned cured tobacco leave—in which the levels of beta-damascenone are modulated. Thus, increasing or reducing beta-damascenone content can result in plant material with an altered flavour profile. In one specific embodiment, compositions and methods for producing mutant, non-naturally occurring or transgenic plants that have been modified to increase neoxanthin synthase expression or activity are provided which can result in plants or plant material—such as heated or burned cured tobacco leave—in which the levels of beta-damascenone are increased. Increasing beta-damascenone content can result in plant material that has a flavour profile with a cooked apple flavour. Decreasing beta-damascenone content can result in plant material that has a modified flavour profile. According to certain embodiments, reference herein to beta-damascenone can also include precursors thereof. Such modification can also modulate the carotenoid content of the plants.

Advantageously, the mutant, non-naturally occurring or transgenic plants that are obtained according to the methods described herein are similar or substantially the same in visual appearance to the control plants. In one embodiment, the stalk height of the mutant, non-naturally occurring or transgenic plants is substantially the same as the control plants at, for example, one, two or three or more months after field transplant or 10, 20, 30 or 36 or more days after topping. For example, the stalk height of the mutant, non-naturally occurring or transgenic plants is not less than the stalk height of the control plants. In another embodiment, the chlorophyll content of the mutant, non-naturally occurring or transgenic plants is substantially the same as the control plants. In another embodiment, the stalk height of the mutant, non-naturally occurring or transgenic plants is substantially the same as the control plants and the chlorophyll content of the mutant, non-naturally occurring or transgenic plants is substantially the same as the control plants. In other embodiments, the size or form or number or coloration of the leaves of the mutant, non-naturally occurring or transgenic plants is substantially the same as the control plants. Suitably, the plant is a tobacco plant.

In another aspect, there is provided a method for modulating the carotenoid content in at least a part of a plant (for example, the leaves), comprising the steps of: (i) modulating the expression or activity of an enzyme selected from the group consisting of neoxanthin synthase, lycopene beta cyclase and 9-cis-epoxycarotenoid dioxygenase or a combination of two or more or three or more thereof (said combinations are disclosed above) in the plant, preferably, wherein the neoxanthin synthase, lycopene beta cyclase and 9-cis-epoxycarotenoid dioxygenase comprises the polynucleotide sequence described herein or the polypeptide sequence described herein; (ii) measuring the carotenoid content in at least a part (for example, the leaves) of the mutant, non-naturally occurring or transgenic plant obtained in step (i); and (iii) identifying a mutant, non-naturally occurring or transgenic plant in which the carotenoid content therein has been modulated in comparison to a control plant. Suitably, the visual appearance of said mutant, non-naturally occurring or transgenic plant is substantially the same as the control plant. Suitably, the plant is a tobacco plant.

In another aspect, there is provided a method for increasing the carotenoid content in at least a part of a plant (for example, the leaves), comprising the steps of: (i) increasing the expression or activity of an enzyme selected from the group consisting of neoxanthin synthase, lycopene beta cyclase and 9-cis-epoxycarotenoid dioxygenase or a combination of two or more or three or more thereof (said combinations are disclosed above) in the plant, preferably, wherein the neoxanthin synthase, lycopene beta cyclase and 9-cis-epoxycarotenoid dioxygenase comprises the polynucleotide sequence described herein or the polypeptide sequence described herein; (ii) measuring the carotenoid content in at least a part (for example, the leaves) of the mutant, non-naturally occurring or transgenic plant obtained in step (i); and (iii) identifying a mutant, non-naturally occurring or transgenic plant in which the carotenoid content therein has been increased in comparison to a control plant. Suitably, the visual appearance of said mutant, non-naturally occurring or transgenic plant is substantially the same as the control plant. Suitably, the plant is a tobacco plant.

In another aspect, there is provided a method for decreasing the carotenoid content in at least a part of a plant (for example, the leaves), comprising the steps of: (i) reducing the expression or activity of an enzyme selected from the group consisting of neoxanthin synthase, lycopene beta cyclase and 9-cis-epoxycarotenoid dioxygenase or a combination of two or more or three or more thereof (said combinations are disclosed above) in the plant, preferably, wherein the neoxanthin synthase, lycopene beta cyclase and 9-cis-epoxycarotenoid dioxygenase comprises the polynucleotide sequence described herein or the polypeptide sequence described herein; (ii) measuring the carotenoid content in at least a part (for example, the leaves) of the mutant, non-naturally occurring or transgenic plant obtained in step (i); and (iii) identifying a mutant, non-naturally occurring or transgenic plant in which the carotenoid content therein has been decreased in comparison to a control plant. Suitably, the visual appearance of said mutant, non-naturally occurring or transgenic plant is substantially the same as the control plant. Suitably, the plant is a tobacco plant.

The increase in expression as compared to the control plant may be from about 5% to about 100%, or an increase of at least 10%, at least 20%, at least 25%, at least 30%, at least 40%, at least 50%, at least 60%, at least 70%, at least 75%, at least 80%, at least 90%, at least 95%, at least 98%, or 100% or more—such as 200% or 300% or more, which includes an increase in transcriptional activity or protein expression or both.

The increase in the activity as compared to a control plant may be from about 5% to about 100%, or an increase of at least 10%, at least 20%, at least 25%, at least 30%, at least 40%, at least 50%, at least 60%, at least 70%, at least 75%, at least 80%, at least 90%, at least 95%, at least 98%, or 100% or more—such as 200% or 300% or more.

The reduction in expression as compared to the control plant may be from about 5% to about 100%, or a reduction of at least 10%, at least 20%, at least 25%, at least 30%, at least 40%, at least 50%, at least 60%, at least 70%, at least 75%, at least 80%, at least 90%, at least 95%, at least 98%, or 100%, which includes a reduction in transcriptional activity or protein expression or both.

The reduction in activity as compared to a control plant may be from about 5% to about 100%, or a reduction of at least 10%, at least 20%, at least 25%, at least 30%, at least 40%, at least 50%, at least 60%, at least 70%, at least 75%, at least 80%, at least 90%, at least 95%, at least 98%, or 100%.

The increase in carotenoid content as compared to a control plant may be from about 5% to about 100%, or an increase of at least 10%, at least 20%, at least 25%, at least 30%, at least 40%, at least 50%, at least 60%, at least 70%, at least 75%, at least 80%, at least 90%, at least 95%, at least 98%, or up to 100% or more—such as 200% or 300% or more.

The decrease in carotenoid content as compared to a control plant may be from about 5% to about 100%, or a decrease of at least 10%, at least 20%, at least 25%, at least 30%, at least 40%, at least 50%, at least 60%, at least 70%, at least 75%, at least 80%, at least 90%, at least 95%, at least 98%, or up to 100%.

In another aspect, there is provided a method for modulating the beta-damascenone content of a plant, comprising the steps of: (i) modulating the expression or activity of neoxanthin synthase in the plant, preferably, wherein the neoxanthin synthase comprises the polynucleotide sequence or the polypeptide sequence described herein; (ii) measuring the beta-damascenone content in at least a part of the mutant, non-naturally occurring or transgenic plant obtained in step (i) or an aerosol thereof; and (iii) identifying a mutant, non-naturally occurring or transgenic plant in which the beta-damascenone content therein has changed in comparison to a control plant in which the expression or activity of neoxanthin synthase has not been modulated. Suitably, the visual appearance of said mutant, non-naturally occurring or transgenic plant is substantially the same as the control plant. Suitably, the plant is a tobacco plant. Suitably, the beta-damascenone content is measured in aerosol formed after heating cured tobacco leaves.

In another aspect, there is provided a method for increasing the beta-damascenone content of a plant, comprising the steps of: (i) increasing the expression or activity of neoxanthin synthase in the plant, preferably, wherein the neoxanthin synthase comprises the polynucleotide sequence or the polypeptide sequence described herein; (ii) measuring the beta-damascenone content in at least a part of the mutant, non-naturally occurring or transgenic plant obtained in step (i); and (iii) identifying a mutant, non-naturally occurring or transgenic plant in which the beta-damascenone content therein has increased in comparison to a control plant in which the expression or activity of neoxanthin synthase has not been increased. Suitably, the visual appearance of said mutant, non-naturally occurring or transgenic plant is substantially the same as the control plant. Suitably, the plant is a tobacco plant. Suitably, the beta-damascenone content is measured in aerosol formed after heating cured tobacco leaves.

In another aspect, there is provided a method for reducing or inhibiting (for example, substantially inhibiting) the beta-damascenone content of a plant, comprising the steps of: (i) reducing or inhibiting the expression or activity of neoxanthin synthase in the plant, preferably, wherein the neoxanthin synthase comprises the polynucleotide sequence or the polypeptide sequence described herein; (ii) measuring the beta-damascenone content in at least a part of the mutant, non-naturally occurring or transgenic plant obtained in step (i); and (iii) identifying a mutant, non-naturally occurring or transgenic plant in which the beta-damascenone content therein has reduced or been inhibited in comparison to a control plant in which the expression or activity of neoxanthin synthase has not been reduced or inhibited. Suitably, the visual appearance of said mutant, non-naturally occurring or transgenic plant is substantially the same as the control plant. Suitably, the plant is a tobacco plant. Suitably, the beta-damascenone content is measured in aerosol formed after heating cured tobacco leaves.

The increase in expression of neoxanthin synthase as compared to the control plant may be from about 5% to about 100%, or an increase of at least 10%, at least 20%, at least 25%, at least 30%, at least 40%, at least 50%, at least 60%, at least 70%, at least 75%, at least 80%, at least 90%, at least 95%, at least 98%, or 100% or more—such as 200% or 300% or more—which includes an increase in transcriptional activity or protein expression or both.

The increase in the activity of neoxanthin synthase as compared to a control plant may be from about 5% to about 100%, or an increase of at least 10%, at least 20%, at least 25%, at least 30%, at least 40%, at least 50%, at least 60%, at least 70%, at least 75%, at least 80%, at least 90%, at least 95%, at least 98%, or 100% or more—such as 200% or 300% or more.

The reduction in expression of neoxanthin synthase as compared to the control plant may be from about 5% to about 100%, or a reduction of at least 10%, at least 20%, at least 25%, at least 30%, at least 40%, at least 50%, at least 60%, at least 70%, at least 75%, at least 80%, at least 90%, at least 95%, at least 98%, or 100%, which includes a reduction in transcriptional activity or protein expression or both.

The reduction in the activity of neoxanthin synthase as compared to a control plant may be from about 5% to about 100%, or a reduction of at least 10%, at least 20%, at least 25%, at least 30%, at least 40%, at least 50%, at least 60%, at least 70%, at least 75%, at least 80%, at least 90%, at least 95%, at least 98%, or 100% or more.

The increase in beta-damascenone content as compared to a control plant may be from about 5% to about 100%, or an increase of at least 10%, at least 20%, at least 25%, at least 30%, at least 40%, at least 50%, at least 60%, at least 70%, at least 75%, at least 80%, at least 90%, at least 95%, at least 98%, or up to 100% or more—such as 200% or 300% or more.

The decrease in beta-damascenone content as compared to a control plant may be from about 5% to about 100%, or a decrease of at least 10%, at least 20%, at least 25%, at least 30%, at least 40%, at least 50%, at least 60%, at least 70%, at least 75%, at least 80%, at least 90%, at least 95%, at least 98%, or up to 100%.

Polynucleotides and recombinant constructs described herein can be used to modulate the expression of the enzymes described herein in a plant species of interest, suitably tobacco.

A number of polynucleotide based methods can be used to increase gene expression in plants. By way of example, a construct, vector or expression vector that is compatible with the plant to be transformed can be prepared which comprises the gene of interest together with an upstream promoter that is capable of overexpressing the gene in the plant. Exemplary promoters are described herein. Following transformation and when grown under suitable conditions, the promoter can drive expression in order to modulate (for example, increase) the levels of this enzyme in the plant, or in a specific tissue thereof. In one exemplary embodiment, a vector carrying NtABA4 or NtNeSy or NtNCED2 polynucleotide (or any of the combinations thereof as described herein) is generated to overexpress the gene in a plant. The vector carries a suitable promoter—such as the cauliflower mosaic virus CaMV 35S promote—upstream of the transgene driving its constitutive expression in all tissues of the plant. The vector also carries an antibiotic resistance gene in order to confer selection of the transformed calli and cell lines. Various embodiments are therefore directed to methods for modulating (for example, increasing) the expression level of NtABA4 or NtNeSy or NtNCED2 polynucleotide (or any of the combinations thereof as described herein) by integrating multiple copies of the polynucleotide into a plant genome, comprising: transforming a plant cell host with an expression vector that comprises a promoter operably-linked to a NtABA4 or NtNeSy or NtNCED2 polynucleotide. The NtABA4 or NtNeSy or NtNCED2 polypeptide encoded by a recombinant polynucleotide can be a native polypeptide, or can be heterologous to the cell.

According to the invention, a tobacco plant carrying a mutant allele of NtABA4 or NtNeSy or NtNCED2 (or any of the combinations thereof as described herein) can be used in a plant breeding program to create useful lines, varieties and hybrids. In particular, the mutant allele is introgressed into the commercially important varieties described above. Thus, methods for breeding plants are provided, that comprise crossing a mutant plant, a non-naturally occurring plant or a transgenic plant as described herein with a plant comprising a different genetic identity. The method may further comprise crossing the progeny plant with another plant, and optionally repeating the crossing until a progeny with the desirable genetic traits or genetic background is obtained. One purpose served by such breeding methods is to introduce a desirable genetic trait into other varieties, breeding lines, hybrids or cultivars, particularly those that are of commercial interest. Another purpose is to facilitate stacking of genetic modifications of different genes in a single plant variety, lines, hybrids or cultivars. Intraspecific as well as interspecific matings are contemplated. The progeny plants that arise from such crosses, also referred to as breeding lines, are examples of non-naturally occurring plants of the invention.

In one embodiment, a method is provided for producing a non-naturally occurring tobacco plant comprising: (a) crossing a mutant or transgenic tobacco plant with a second tobacco plant to yield progeny tobacco seed; (b) growing the progeny tobacco seed, under plant growth conditions, to yield the non-naturally occurring tobacco plant. The method may further comprises: (c) crossing the previous generation of non-naturally occurring tobacco plant with itself or another tobacco plant to yield progeny tobacco seed; (d) growing the progeny tobacco seed of step (c) under plant growth conditions, to yield additional non-naturally occurring tobacco plants; and (e) repeating the crossing and growing steps of (c) and (d) multiple times to generate further generations of non-naturally occurring tobacco plants. The method may optionally comprises prior to step (a), a step of providing a parent plant which comprises a genetic identity that is characterized and that is not identical to the mutant or transgenic plant. In some embodiments, depending on the breeding program, the crossing and growing steps are repeated from 0 to 2 times, from 0 to 3 times, from 0 to 4 times, 0 to 5 times, from 0 to 6 times, from 0 to 7 times, from 0 to 8 times, from 0 to 9 times or from 0 to 10 times, in order to generate generations of non-naturally occurring tobacco plants. Backcrossing is an example of such a method wherein a progeny is crossed with one of its parents or another plant genetically similar to its parent, in order to obtain a progeny plant in the next generation that has a genetic identity which is closer to that of one of the parents. Techniques for plant breeding, particularly tobacco plant breeding, are well known and can be used in the methods of the invention. The invention further provides non-naturally occurring tobacco plants produced by these methods.

In some embodiments of the methods described herein, lines resulting from breeding and screening for variant genes are evaluated in the field using standard field procedures. Control genotypes including the original unmutagenized parent are included and entries are arranged in the field in a randomized complete block design or other appropriate field design. For tobacco, standard agronomic practices are used, for example, the tobacco is harvested, weighed, and sampled for chemical and other common testing before and during curing. Statistical analyses of the data are performed to confirm the similarity of the selected lines to the parental line. Cytogenetic analyses of the selected plants are optionally performed to confirm the chromosome complement and chromosome pairing relationships.

DNA fingerprinting, single nucleotide polymorphism, microsatellite markers, or similar technologies may be used in a marker-assisted selection (MAS) breeding program to transfer or breed mutant alleles of a gene into other tobaccos, as described herein. For example, a breeder can create segregating populations from hybridizations of a genotype containing a mutant allele with an agronomically desirable genotype. Plants in the F2 or backcross generations can be screened using a marker developed from a genomic sequence or a fragment thereof, using one of the techniques listed herein. Plants identified as possessing the mutant allele can be backcrossed or self-pollinated to create a second population to be screened. Depending on the expected inheritance pattern or the MAS technology used, it may be necessary to self-pollinate the selected plants before each cycle of backcrossing to aid identification of the desired individual plants. Backcrossing or other breeding procedure can be repeated until the desired phenotype of the recurrent parent is recovered.

According to the disclosure, in a breeding program, successful crosses yield F1 plants that are fertile. Selected F1 plants can be crossed with one of the parents, and the first backcross generation plants are self-pollinated to produce a population that is again screened for variant gene expression (for example, the null version of the gene). The process of backcrossing, self-pollination, and screening is repeated, for example, at least 4 times until the final screening produces a plant that is fertile and reasonably similar to the recurrent parent. This plant, if desired, is self-pollinated and the progeny are subsequently screened again to confirm that the plant exhibits variant gene expression. In some embodiments, a plant population in the F2 generation is screened for variant gene expression, for example, a plant is identified that fails to express a polypeptide due to the absence of the gene according to standard methods, for example, by using a PCR method with primers based upon the nucleotide sequence information for the polynucleotides including NtABA4 or NtNeSy or NtNCED2 polynucleotide (or any of the combinations thereof) as described herein.

Hybrid tobacco varieties can be produced by preventing self-pollination of female parent plants (that is, seed parents) of a first variety, permitting pollen from male parent plants of a second variety to fertilize the female parent plants, and allowing F1 hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by cytoplasmic male sterility (CMS), or transgenic male sterility wherein a transgene inhibits microsporogenesis and/or pollen formation, or self-incompatibility. Female parent plants containing CMS are particularly useful. In embodiments in which the female parent plants are CMS, pollen is harvested from male fertile plants and applied manually to the stigmas of CMS female parent plants, and the resulting F1 seed is harvested.

Varieties and lines described herein can be used to form single-cross tobacco F1 hybrids. In such embodiments, the plants of the parent varieties can be grown as substantially homogeneous adjoining populations to facilitate natural cross-pollination from the male parent plants to the female parent plants. The F1 seed formed on the female parent plants is selectively harvested by conventional means. One also can grow the two parent plant varieties in bulk and harvest a blend of F1 hybrid seed formed on the female parent and seed formed upon the male parent as the result of self-pollination. Alternatively, three-way crosses can be carried out wherein a single-cross F1 hybrid is used as a female parent and is crossed with a different male parent. As another alternative, double-cross hybrids can be created wherein the F1 progeny of two different single-crosses are themselves crossed.

A population of mutant, non-naturally occurring or transgenic plants can be screened or selected for those members of the population that have a desired trait or phenotype. For example, a population of progeny of a single transformation event can be screened for those plants having a desired level of expression or activity of NtABA4 or NtNeSy or NtNCED2 or the polypeptide encoded thereby. Physical and biochemical methods can be used to identify expression or activity levels. These include Southern analysis or PCR amplification for detection of a polynucleotide; Northern blots, 51 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining and enzyme assays also can be used to detect the presence or expression or activity of polypeptides or polynucleotides.

Mutant, non-naturally occurring or transgenic plant cells and plants are described herein comprising one or more recombinant polynucleotides—such as one or more isolated NtABA4 or NtNeSy or NtNCED2 polynucleotides (or a combination of two or more or three or more thereof), one or more polynucleotide constructs, one or more double-stranded RNAs, one or more conjugates or one or more vectors/expression vectors.

Without limitation, the plants described herein may be modified for other purposes either before or after the expression or activity has been modulated according to the present invention. One or more of the following genetic modifications can be present in the mutant, non-naturally occurring or transgenic plants. In one embodiment, one or more genes that are involved in heavy metal uptake or heavy metal transport are modified resulting in plants or parts of plants (such as leaves) having a lower heavy metal content than control plants or parts thereof without the modification(s). Non-limiting examples include genes in the family of multidrug resistance associated proteins, the family of cation diffusion facilitators (CDF), the family of Zrt-, Irt-like proteins (ZIP), the family of cation exchangers (CAX), the family of copper transporters (COPT), the family of heavy-metal P-type ATPases (HMAs, as described in WO2009074325), the family of homologs of natural resistance-associated macrophage proteins (NRAMP), and the family of ATP-binding cassette (ABC) transporters, which participate in transport of heavy metals, such as cadmium. The term heavy metal as used herein includes transition metals. In another embodiment, one or more genes that are involved in the conversion of nitrogenous metabolic intermediates is modified resulting in plants or parts of plants (such as leaves) that when heated, produces lower levels of at least one tobacco-specific nitrosamine (for example, 4-(methylnitrosamino)-1-(3-pyridyl)-1-butanone, N-nitrosonornicotine, N-nitrosoanatabine, and N-nitrosoanabasine) than control plants or parts thereof. Non-limiting examples of genes that can be modified include genes encoding a nicotine demethylase, such as CYP82E4, CYP82E5 and CYP82E10 which participate in the conversion of nicotine to nornicotine and are described in WO2006091194, WO2008070274, WO2009064771 and PCT/US2011/021088.

Examples of other modifications include herbicide tolerance, for example, glyphosate is an active ingredient of many broad spectrum herbicides. Glyphosate resistant transgenic plants have been developed by transferring the aroA gene (a glyphosate EPSP synthetase from *Salmonella typhimurium* and *E. coli*). Sulphonylurea resistant plants have been produced by transforming the mutant ALS (acetolactate synthetase) gene from *Arabidopsis*. QB protein of photosystem II from mutant *Amaranthus hybridus* has been transferred in to plants to produce atrazine resistant transgenic plants; and bromoxynil resistant transgenic plants have been produced by incorporating the bxn gene from the bacterium *Klebsiella pneumoniae*. Another exemplary modification results in plants that are resistant to insects. *Bacillus thuringiensis* (Bt) toxins can provide an effective way of delaying the emergence of Bt-resistant pests, as recently illustrated in broccoli where pyramided cry1Ac and cry1C Bt genes controlled diamondback moths resistant to either single protein and significantly delayed the evolution of resistant insects. Another exemplary modification results in plants that are resistant to diseases caused by pathogens (for example, viruses, bacteria, fungi). Plants expressing the Xa21 gene (resistance to bacterial blight) with plants expressing both a Bt fusion gene and a chitinase gene (resistance to yellow stem borer and tolerance to sheath) have been engineered. Another exemplary modification results in altered reproductive capability, such as male sterility. Another exemplary modification results in plants that are tolerant to abiotic stress (for example, drought, temperature, salinity), and tolerant transgenic plants have been produced by transferring acyl glycerol phosphate enzyme from *Arabidopsis*; genes coding mannitol dehydrogenase and sorbitol dehydrogenase which are involved in synthesis of mannitol and sorbitol improve drought resistance. Another exemplary modification results in plants that produce proteins which may have favourable immunogenic properties for use in humans. For example, plants capable of producing proteins which substantially lack alpha-1,3-linked fucose residues, beta-1,2-linked xylose residues, or both, in its N-glycan may be of use. Other exemplary modifications can result in plants with improved storage proteins and oils, plants with enhanced photosynthetic efficiency, plants with prolonged shelf life, plants with enhanced carbohydrate content, and plants resistant to fungi; plants encoding an enzyme involved in the biosynthesis of alkaloids. Transgenic plants in which the expression of S-adenosyl-L-methionine (SAM) and/or cystathionine gamma-synthase (CGS) has been modulated are also contemplated.

One or more such traits may be introgressed into the mutant, non-naturally occurring or transgenic tobacco plants from another tobacco cultivar or may be directly transformed into it. The introgression of the trait(s) into the mutant, non-naturally occurring or transgenic tobacco plants of the invention maybe achieved by any method of plant breeding known in the art, for example, pedigree breeding, backcrossing, doubled-haploid breeding, and the like (see, Wernsman, E. A, and Rufty, R. C. 1987. Chapter Seventeen. Tobacco. Pages 669-698 In: *Cultivar Development. Crop Species*. W. H. Fehr (ed.), MacMillan Publishing Co, Inc., New York, N.Y. 761 pp.). Molecular biology-based techniques described above, in particular RFLP and microsatelite markers, can be used in such backcrosses to identify the progenies having the highest degree of genetic identity with the recurrent parent. This permits one to accelerate the production of tobacco varieties having at least 90%, preferably at least 95%, more preferably at least 99% genetic identity with the recurrent parent, yet more preferably genetically identical to the recurrent parent, and further comprising the trait(s) introgressed from the donor parent. Such determination of genetic identity can be based on molecular markers known in the art.

The last backcross generation can be selfed to give pure breeding progeny for the nucleic acid(s) being transferred. The resulting plants generally have essentially all of the morphological and physiological characteristics of the mutant, non-naturally occurring or transgenic tobacco plants of the invention, in addition to the transferred trait(s) (for example, one or more single gene traits). The exact backcrossing protocol will depend on the trait being altered to determine an appropriate testing protocol. Although backcrossing methods are simplified when the trait being transferred is a dominant allele, a recessive allele may also be transferred. In this instance, it may be necessary to introduce a test of the progeny to determine if the desired trait has been successfully transferred. Various embodiments provide mutant plants, non-naturally occurring plants or transgenic plants, as well as biomass in which the expression level of a NtABA4 or NtNeSy or NtNCED2 polynucleotide (or any combination thereof) is modulated to modulate the carotenoid content or the beta-damascenone content in the aerosol formed after heating cured tobacco prepared from the plants. Parts of such plants, particularly tobacco plants, and more particularly the leaf lamina and midrib of tobacco plants, can be incorporated into or used in making various consumable products including but not limited to aerosol forming materials, aerosol forming devices, smoking articles, smokable articles, smokeless products, and tobacco products. Examples of aerosol forming materials include but are not limited to tobacco compositions, tobaccos, tobacco extract, cut tobacco, cut filler, cured tobacco, expanded tobacco, homogenized tobacco, reconstituted tobacco, and pipe tobaccos. Smoking articles and smokable articles are types of aerosol forming devices. Examples of smoking articles or smokable articles include but are not limited to cigarettes, cigarillos, and cigars. Examples of smokeless products comprise chewing tobaccos, and snuffs. In certain aerosol forming devices, rather than combustion, a tobacco composition or another aerosol forming material is heated by one or more electrical heating elements to produce an aerosol. In another type of heated aerosol forming device, an aerosol is produced by the transfer of heat from a combustible fuel element or heat source to a physically separate aerosol forming material, which may be located within, around or downstream of the heat source. Smokeless tobacco products and various tobacco-containing aerosol forming materials may contain tobacco in any form, including as dried particles, shreds, granules, powders, or a slurry, deposited on, mixed in, surrounded by, or otherwise combined with other ingredients in any format, such as flakes, films, tabs, foams, or beads. As used herein, the term 'smoke' is used to describe a type of aerosol that is produced by smoking articles, such as cigarettes, or by combusting an aerosol forming material.

In one embodiment, there is also provided cured material from the mutant, transgenic and non-naturally occurring tobacco plants described herein. Processes of curing green tobacco leaves are known by those having skills in the art and include without limitation air-curing, fire-curing, flue-curing and sun-curing. The process of curing green tobacco leaves depends on the type of tobacco harvested. For example, Virginia flue (bright) tobacco is typically flue-cured, Burley and certain dark strains are usually air-cured, and pipe tobacco, chewing tobacco, and snuff are usually fire-cured.

In another embodiment, there is described tobacco products including tobacco-containing aerosol forming materials comprising leaves, preferably cured leaves, from the mutant tobacco plants, transgenic tobacco plants or non-naturally occurring tobacco plants described herein. The tobacco products described herein can be a blended tobacco product which may further comprise unmodified tobacco.

The % carotenoid or beta-damascenone or % carotenoid and beta-damascenone in these smokable articles and smokeless products and aerosols thereof may be at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, and 100% or more—such as 200% or 300%—or more higher, when compared to consumable products derived from non-mutant, non-naturally occurring or non-transgenic counterparts.

The % carotenoid or % beta-damascenone or % carotenoid and beta-damascenone in these smokable articles and smokeless products and aerosols thereof may be at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, and 100% lower, when compared to consumable products derived from non-mutant, non-naturally occurring or non-transgenic counterparts.

The mutant, non-naturally occurring or transgenic plants may have other uses in, for example, agriculture. For example, mutant, non-naturally occurring or transgenic plants described herein can be used to make animal feed and human food products.

The invention also provides methods for producing seeds comprising cultivating the mutant plant, non-naturally occurring plant, or transgenic plant described herein, and collecting seeds from the cultivated plants. Seeds from plants described herein can be conditioned and bagged in packaging material by means known in the art to form an article of manufacture. Packaging material such as paper and cloth are well known in the art. A package of seed can have a label, for example, a tag or label secured to the packaging material, a label printed on the package that describes the nature of the seeds therein.

A further aspect relates to a method for producing beta-damascenone comprising the steps of: (a) providing part of a mutant, non-naturally occurring or transgenic plant; biomass, seed or leaves; or the tobacco product as described herein; and (b) providing heat thereto.

Compositions, methods and kits for genotyping plants for identification, selection, or breeding can comprise a means of detecting the presence of a NtABA4 or NtNeSy or NtNCED2 polynucleotide (or a combination of two or more or three or more thereof) in a sample of polynucleotide.

Accordingly, a composition is described comprising one of more primers (for example, one or more primers or probes comprising, consisting or consisting essentially of the sequence set forth in SEQ ID NOs: 3 to 5, 10 to 12 or 14 to 16) for specifically amplifying at least a portion of one or more of the polynucleotides and optionally one or more probes and optionally one or more reagents for conducting the amplification or detection.

Accordingly, gene specific oligonucleotide primers or probes comprising about 10 or more contiguous polynucleotides corresponding to the NtABA4 or NtNeSy or NtNCED2 polynucleotide are disclosed. Said primers or probes may comprise or consist of about 15, 20, 25, 30, 40, 45 or 50 more contiguous polynucleotides that hybridise (for example, specifically hybridise) to the NtABA4 or NtNeSy or NtNCED2 polynucleotide. In some embodiments, the primers or probes may comprise or consist of about 10 to 50 contiguous nucleotides, about 10 to 40 contiguous nucleotides, about 10 to 30 contiguous nucleotides or about 15 to 30 contiguous nucleotides that may be used in sequence-dependent methods of gene identification (for example, Southern hybridization) or isolation (for example, in situ hybridization of bacterial colonies or bacteriophage plaques) or gene detection (for example, as one or more amplification primers in nucleic acid amplification or detection). The one or more specific primers or probes can be designed and used to amplify or detect a part or all of the NtABA4 or NtNeSy or NtNCED2 polynucleotide. By way of specific example, two primers may be used in a polymerase chain reaction protocol to amplify a nucleic acid fragment encoding NtABA4 or NtNeSy or NtNCED2 nucleic acid—such as DNA or RNA. The polymerase chain reaction may also be performed using one primer that is derived from the NtABA4 or NtNeSy or NtNCED2 nucleic acid sequence and a second primer that hybridises to a sequence upstream or downstream of the NtABA4 or NtNeSy or NtNCED2 nucleic acid sequence—such as a NtABA4 or NtNeSy or NtNCED2 promoter sequence, the 3' end of the mRNA precursor or a sequence derived from a vector. Examples of thermal and isothermal techniques useful for in vitro amplification of polynucleotides are well known in the art. The sample may be or may be derived from a plant, a plant cell or plant material or a tobacco product made or derived from the plant, the plant cell or the plant material as described herein.

In a further aspect, there is also provided a method of detecting a NtABA4 or NtNeSy or NtNCED2 polynucleotide (or a combination of two or more or three or more thereof) in a sample comprising the step of: (a) providing a sample comprising, or suspected of comprising, a polynucleotide; (b) contacting said sample with one of more primers or one or more probes for specifically detecting at least a portion of the polynucleotide(s); and (c) detecting the presence of an amplification product, wherein the presence of an amplification product is indicative of the presence of the polynucleotide(s) in the sample. In a further aspect, there is also provided the use of one of more primers or probes for specifically detecting at least a portion of the polynucleotide(s). Kits for detecting at least a portion of the polynucleotide(s) are also provided which comprise one of more primers or probes for specifically detecting at least a portion of the polynucleotide(s). The kit may comprise reagents for polynucleotide amplification—such as PCR—or reagents for probe hybridization-detection technology—such as Southern Blots, Northern Blots, in-situ hybridization, or microarray. The kit may comprise reagents for antibody binding-detection technology such as Western Blots, ELISAs, SELDI mass spectrometry or test strips. The kit may comprise reagents for DNA sequencing. The kit may comprise reagents and instructions for determining carotenoid (for example, lutein or beta-carotene; or lutein and beta-carotene) and beta-damascenone content or beta-damascenone content. The kit may comprise reagents and instructions for determining carotenoid (for example, lutein or beta-carotene; or lutein and beta-carotene) and beta-damascenone content or beta-damascenone content.

In some embodiments, a kit may comprise instructions for one or more of the methods described. The kits described may be useful for genetic identity determination, phylogenetic studies, genotyping, haplotyping, pedigree analysis or plant breeding particularly with co-dominant scoring. The present invention also provides a method of genotyping a plant, a plant cell or plant material comprising a polynucleotide as described herein. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. The specific method of genotyping may employ any number of molecular marker analytic techniques including amplification fragment length polymorphisms (AFLPs). AFLPs are the product of allelic differences between amplification fragments caused by nucleotide sequence variability. Thus, the present invention further provides a means to follow segregation of one or more genes or nucleic acids as well as chromosomal sequences genetically linked to these genes or nucleic acids using such techniques as AFLP analysis.

In one embodiment, there is also provided cured material from the mutant, transgenic and non-naturally occurring plants described herein. For example, processes of curing green tobacco leaves are known by those having skills in the field and include without limitation air-curing, fire-curing, flue-curing and sun-curing. The process of curing green tobacco leaves depends on the type of tobacco harvested. For example, Virginia flue (bright) tobacco is typically flue-cured, Burley and certain dark strains are usually air-cured, and pipe tobacco, chewing tobacco, and snuff are usually fire-cured.

In another embodiment, there is described tobacco products including tobacco products comprising leaves, preferably cured leaves, from the mutant, transgenic and non-naturally occurring plants described herein or which are produced by the methods described herein. The tobacco products described herein may further comprise unmodified tobacco.

In another embodiment, there is described tobacco products comprising plant material, preferably leaves—such as cured leaves, from the mutant, transgenic and non-naturally occurring plants described herein. For example, the plant material may be added to the inside or outside of the tobacco product and so upon burning a desirable aroma is released. The tobacco product according to this embodiment may even be an unmodified tobacco or a modified tobacco. The tobacco product according to this embodiment may even be derived from a mutant, transgenic or non-naturally occurring plant which has modifications in one or more genes other than the genes disclosed herein.

A further aspect relates to an isolated polynucleotide comprising, consisting or consisting essentially of a sequence encoding a lycopene beta cyclase and having at least 60% sequence identity to SEQ ID NO:8. A further aspect relates to an isolated polypeptide encoded by this polynucleotide. A further aspect relates to an isolated polypeptide having at least 87% sequence identity to SEQ ID NO:9. A further aspect relates to a construct, vector or expression vector comprising the isolated polynucleotide. A further aspect relates to a mutant, non-naturally occurring or transgenic plant cell comprising the isolated polynucleotide, the polypeptide or the construct, vector or expression vector and wherein the expression or activity of lycopene beta cyclase is modulated as compared to a control or wild type plant, preferably, wherein the expression or activity of neoxanthin synthase or 9-cis-epoxycarotenoid dioxygenase; or neoxanthin synthase and 9-cis-epoxycarotenoid dioxygenase is also modulated. A further aspect relates to a mutant, non-naturally occurring or transgenic plant comprising the plant cell. A further aspect relates to a method for modulating the carotenoid content of a plant, comprising the steps of: (i) modulating the expression or activity of lycopene beta cyclase in the plant, preferably, wherein the lycopene beta cyclase comprises the polynucleotide sequence or the polypeptide sequence described herein; (ii) measuring the carotenoid content in at least a part of the mutant, non-naturally occurring or transgenic plant obtained in step (i); and (iii) identifying a mutant, non-naturally occurring or transgenic plant in which the carotenoid content therein has changed in comparison to a control plant in which the expression or activity of lycopene beta cyclase has not been modulated. In one embodiment, the expression or activity of lycopene beta cyclase or 9-cis-epoxycarotenoid dioxygenase; and lycopene beta cyclase and 9-cis-epoxycarotenoid dioxygenase is also modulated. A further aspect relates to a mutant, non-naturally occurring or transgenic plant or plant material derived or derivable therefrom that is obtained or obtainable by this method. A further aspect relates to a mutant, non-naturally occurring or transgenic plant, wherein expression of lycopene beta cyclase or the activity of the protein encoded thereby has been increased; wherein the green leaf lutein content or the beta-carotene content or the combined content of the plant is higher than a control plant in which the expression or the activity of lycopene beta cyclase has not been increased, preferably, wherein: (i) the green leaf lutein content of the plant is at least about 17 mg/100 g (for example, at least about 17.5 mg/100 g; at least about 18 mg/100 g, at least about 18.5 mg/100 g or at least about 19 mg/100 g) and (ii) the beta-carotene content of the plant is at least about 10 mg/100 g (for example, at least about 10.5 mg/100 g; at least about 11 mg/100 g, at least about 11.5 mg/100 g or at least about 12 mg/100 g). A further aspect relates to plant material including biomass, seed or leaves comprising cells or tissue from the plant. A further aspect relates to a tobacco product comprising the plant cells, at least a part of the plant or plant material.

A further aspect relates to an isolated polynucleotide comprising, consisting or consisting essentially of a sequence encoding 9-cis-epoxycarotenoid dioxygenase and having at least 60% sequence identity to SEQ ID NO:13. A further aspect relates to an isolated polypeptide encoded by this polynucleotide. A further aspect relates to a construct, vector or expression vector comprising the isolated polynucleotide. A further aspect relates to a mutant, non-naturally occurring or transgenic plant cell comprising the isolated polynucleotide, the polypeptide or the construct, vector or expression vector and wherein the expression or activity of 9-cis-epoxycarotenoid dioxygenase is modulated as compared to a control or wild type plant, preferably, wherein the expression or activity of neoxanthin synthase or lycopene beta cyclase; or neoxanthin synthase and lycopene beta cyclase is also modulated. A further aspect relates to a mutant, non-naturally occurring or transgenic plant comprising the plant cell. A further aspect relates to a method for modulating the carotenoid content of a plant, comprising the steps of: (i) modulating the expression or activity of 9-cis-epoxycarotenoid dioxygenase in the plant, preferably, wherein the 9-cis-epoxycarotenoid dioxygenase comprises the polynucleotide sequence or the polypeptide sequence described herein; (ii) measuring the carotenoid content in at least a part of the mutant, non-naturally occurring or transgenic plant obtained in step (i); and (iii) identifying a mutant, non-naturally occurring or transgenic plant in which the carotenoid content therein has changed in comparison to a control plant in which the expression or activity of 9-cis-epoxycarotenoid dioxygenase has not been modulated. In one embodiment, the expression or activity of neoxanthin synthase or lycopene beta cyclase; and neoxanthin synthase and lycopene beta cyclase is also modulated. A further aspect relates to a mutant, non-naturally occurring or transgenic plant or plant material derived or derivable therefrom that is obtained or obtainable by this method. A further aspect relates to a mutant, non-naturally occurring or transgenic plant, wherein expression of 9-cis-epoxycarotenoid dioxygenase or the activity of the protein encoded thereby has been increased; wherein the green leaf lutein content or the beta-carotene content or the combined content of the plant is higher than a control plant in which the expression or the activity of 9-cis-epoxycarotenoid dioxygenase has not been increased, preferably, wherein: (i) the green leaf lutein content of the plant is at least about 15 mg/100 g (for example, at least about 15.5 mg/100 g; at least about 16 mg/100 g, at least about 16.5 mg/100 g or at least about 17 mg/100 g); and (ii) the beta-carotene content of the plant is at least about 11 mg/100 g (for example, at least about 11.5 mg/100 g; at least about 12 mg/100 g, at least about 12.5 mg/100 g or at least about 13 mg/100 g). A further aspect relates to plant material including biomass, seed or leaves comprising cells or tissue from the plant. A further aspect relates to a tobacco product comprising the plant cells, at least a part of the plant or plant material.

The invention is further described in the Examples below, which are provided to describe the invention in further detail. These examples, which set forth a preferred mode presently contemplated for carrying out the invention, are intended to illustrate and not to limit the invention.

EXAMPLES

Example 1

Cloning of ABA4 from Nicotinia tabacum

Figure 3:
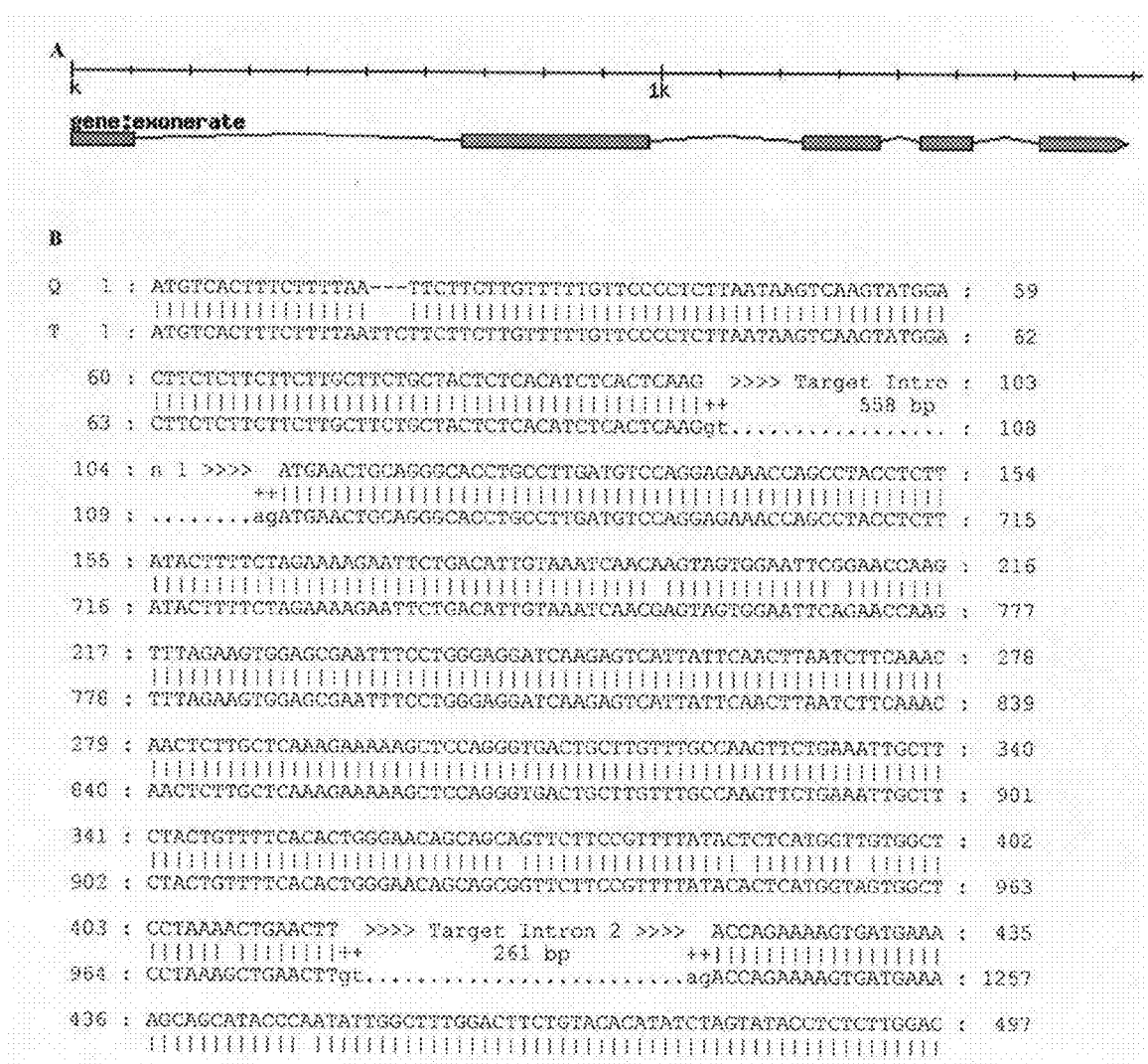
FIG. 3. Cloning and sequencing of a tobacco genomic sequence from Hicks Broadleaf corresponding to a copy of the NtABA4 gene. (A) This genomic sequence with five exons and four introns covers a total of 1808 bp (1792+16 bp intron borders). (B) The NtABA4 cDNA (T) and the cloned genomic N1ABA4 isoform (CQ) are not identical. (C) The predicted 786 bp-long NIABA4 copy deduced from the genomic sequence (Sbjct) differs in 7 amino acids from the cloned N1ABA4 cDNA (Query) including one serine at position 9 in the chloroplast transit peptide which is absent in the genomic copy.

A Nicotinia tabacum coding sequence homologous to ABA4 is ectopically expressed. The gene is called Nicotinia tabacum ABA4 (NtABA4) based on sequence homologies with A. thaliana ABA4. NtABA4 is a gene belonging to the extended "family" of neoxanthin synthase enzymes which catalyzes the formation of trans-neoxanthin from violaxanthin. The gene product is very likely to be localized in the plastids by analogy with AtABA4 and according to WoLFP-SORT analyses. A full length coding sequence of 663 kb is identified and amplified using leaf K326 cDNA as PCR template, cloned into a pENTR Gateway vector (Invitrogen), sequenced and transferred into pK2WG7 (Gateway vector obtained from Flanders Interuniversity Institute for Biotechnology, Gent, Belgium) for constitutive expression in Nicotinia tabacum. The nucleotide and amino acid sequences of NtABA4 are set forth in SEQ ID No.1 and SEQ ID No. 2, respectively and in FIG. 2. NtABA4 displays 65% identity at the amino acid level with the Arabidopsis protein AtABA4, At1g67080. PCR amplification starting from gDNA of Hicks Broadleaf as template, allowed us to identity a NtABA4 homolog of 1808 bp. By comparing the cDNA and gDNA sequences, the gene structure was deduced to demonstrate that NtABA4 possesses 4 introns and 5 exons (FIG. 3A). Differences between the K326 and Hicks BL NtABA4 isoforms exist (FIG. 3B). The NtABA4 amino acid sequence from Hicks Broadleaf has 97% identity with the K326 sequence which is due to a 6 amino acid difference and one missing serine at position 9 (FIG. 3C). As indicated by expressed sequence tag comparisons, the NtABA4 genomic sequence is not a pseudogene since an expressed sequence tag (AM824569) having identical features at the N-terminal end has been identified in a NCBI cold stress sequence library from SNN tobacco. For tobacco engineering, the NtABA4 K326 cDNA sequence is used and constitutively expressed in TN90 under the control of the strong viral CaMV35S promoter.

Example 2

Cloning of Neoxanthin Synthase (NeSy) from Nicotinia tabacum

NeSy (lycopene beta cyclase), like ABA4, catalyzes the formation of neoxanthin (cis-neoxanthin) from violaxanthin (see FIG. 1). This enzyme is likely localized in plastids (based on homology to Arabadopsis thaliana NeSy). Starting with a sequence available in the TGI database, a full length coding sequence of 1482 kb (see FIG. 4) is amplified from K326 RNA, cloned in a pENTR Gateway vector (Invitrogen), sequenced and subcloned in the Gateway vector pK2WG7 (obtained from Flanders Interuniversity Institute for Biotechnology, Gent, Belgium) for over-expression. A BAC clone is identified. The genomic sequence present on this BAC clone shows that NtNeSy has no intron in the genomic structure and is very likely a single-copy gene in tobacco. NtNeSy K326 cDNA is constitutively expressed in TN90 under the control of the CaMV35S promoter for comparison with 35S::NtABA4 plants.

Example 3

Cloning of 9-cis-epoxycarotenoid dioxygenase (CED2) from Nicotinia tabacum

CED2 (9-cis-epoxycarotenoid dioxygenase) catalyzes the cleavage of cis-neoxanthin in $C_{25}$-allenic-apo-aldehyde and xanthoxin (see FIG. 1). NtCED2 shares strong homology with Arabidopsis AtNCED4, which is present in plastoglobules and likely cleaves neoxanthin in the leaf chloroplast. A tobacco cDNA fragment is identified in the TGI database. From this, a partial sequence (407 bp) is cloned in a pENTR Gateway vector (Invitrogen), sequenced and subcloned in the Gateway vector pK7GWIWG2(II), obtained from Flanders Interuniversity Institute for Biotechnology, Gent, Belgium. In this case, the NtCED2 fragment is expressed as a RNA hairpin in tobacco plants inducing gene silencing of the corresponding endogenous NtCED2 transcript (FIG. 5).

Example 4

Engineering TN90 Burley Tobacco with NtABA4 cDNA

A binary plasmid pK2WG7 carrying the NtABA4 coding sequence (FIG. 2) is generated to over-express this gene in

*Nicotinia tabacum*. This vector includes the cauliflower mosaic virus CaMV 35S promoter upstream of the transgene driving its constitutive expression in all tissues of the plant and the kan/nptII gene for kanamycin (antibiotic) selection of transgenic *Nicotinia tabacum* lines on agar plates (100 mg/ml). Burley tobacco TN90 is transformed with this construct via *Agrobacterium tumefaciens* using a classical leaf disk procedure. From calli, individual lines are regenerated and selected on kanamycin. T0 over-expressing lines are then monitored by PCR on genomic DNA using one primer in the 35S promoter (5'-GAGCATCGTG-GAAAAAGAAGAC) (SEQ ID NO: 17) and one primer within the NtABA4 coding sequence specifically detecting the transgenic copy of NtABA4 by RT-PCR using specific NtABA4 primers. T1 seeds were collected, re-grown on kanamycin-containing agar plates and monitored exactly as for T0 plantlets. PCR on gDNA shows that the T-DNA harboring the NtABA4 cDNA was inserted in the genome in selected lines and RT-PCR analysis allowed to identify three lines in which the gene was over-expressed. Kanamycin resistant plants are subsequently grown in floating trays before cultivation in the field. Twenty plants of the three NtABA4 lines (NtABA4-I, NtABA-2 and NtABA-3), vector control (VC, empty pK7GWIWG2(II)) and TN90 US background tobacco are cultivated in four replicates of 20 plants. Three months after transplanting into the field (36 days after topping), one leaf in mid-stalk position is sampled in 10 identical plants out of the 20 plants in the subplot representing one experimental replicate. These leaves ("green leaves") are immediately stored in dry ice and lyophilized. 35S::NtABA4 plants did not exhibit any visual phenotypes different from TN90 and VC plants after two months in the field. Along the same lines, plant height and chlorophyll content analysis documents that the transgenic 35S::NtABA4 lines were similar to TN90 and VC controls suggesting that NtABA4 overexpression has no visible impact on phenotypic properties. The remaining leaf material of the 10 selected plants per subplot and line is sampled and cured according to Burley agricultural practices. After curing, three leaves at mid-stalk position are sampled. To monitor the effect of increased NtABA4 expression in the three transgenic lines (NtABA4-1, NtABA4-2 and NtABA4-3), "green leaves" and "cured leaves" are ground and subjected to carotenoid analyses.

Example 5

Carotenoid Analyses in Green and Cured Leaves of 35S::NtABA4 Transgenic Lines

In "green leaves" quantitative analyses of carotenoids is not possible for all xanthophylls due to technical limitations, particularly for neoxanthin quantification (low concentrations in *Nicotinia tabacum* and poor analytical separation). It is assumed that the pool of neoxanthin (based on semi-quantitative analyses, data not shown) has a similar trend to lutein (and also beta-carotene to a lesser extent) content in TN90, VC, NtABA4-1, NtABA4-2 and Nt-ABA4-3. Both latter pigments are used as representative measures of the concentrations of other carotenoids (xanthophylls) in green leaves. In contrast, in senescent and cured leaves such assumptions are not considered because the neoxanthin pool is known to be rapidly and fully degraded. The carotenoid analysis is performed using the classical HPLC method and visible detection. in NtABA4 over-expressing lines shows that lutein is significantly elevated in the NtABA4-2 and NtABA4-3 lines when compared to wild type and vector control. Over-expression of NtABA4 results in a leaf lutein increase of 30% and 26% in NtABA4-2 and NtABA4-3 lines, respectively, when compared to TN90 and vector control background lines. In addition, beta-carotene is also significantly higher in NtABA4 lines (about 15% higher) as compared to wild type TN90. These data indicate that over-expressing NtABA4 has an overall increasing effect on carotenoid content. The increase in carotenoids within the transgenic plant lines is significant ($P<0.05$; T test).

The analysis of carotenoids in cured leaves shows globally a decrease in lutein and beta-carotene pools compared to green leaves. 87 to 95% of the lutein and beta-carotene present in green samples is degraded during curing in all wild-type, vector control and 35S::NtABA4 transgenic lines. This suggests that these carotenoids are subjected to active enzymatic or chemical modifications during curing. The presence of large variations within each cured sample set indicates that carotenoid catabolism during curing is a less 'controlled' and homogenous process than carotenoid synthesis in green leaves. T-test analysis shows that the lutein content is significantly different when comparing the following lines: NtABA4-2 is higher than TN90 ($P<0.001I$) and the vector control ($P<0.05$); vector control is higher than TN90 ($P<0.05$) and NtABA4-1 is higher than TN90 ($P<0.05$). The beta-carotene content is higher in vector control ($P<0.05$) and NtABA4-1 ($P<0.011$) when compared to TN90.

Example 6

Carotenoid Analysis of Selected 35S::NeSy and NtCED2-Interfering RNA Lines

As described for 35S::NtABA4, the 35S::NtNeSy and NtNCED2-interfering RNA transformed lines are selected based on genotyping and RT-PCR. As a result, two 35S::NtNeSy and three NtNCED2-interfering RNA lines are identified and planted in four replicates at the same time and in the same field. The content of the major carotenoids (lutein and beta-carotene) is determined in NCED2-interfering RNA and 35S::NtNeSy lines. Both NCED2-interfering RNA and 35S::NtNeSy lines exhibit an increase in the main carotenoids in green leaves, confirming that these two gene candidates for plant transformation affect carotenoid metabolism in tobacco leaf. However, when comparing all selected transgenic lines, NtABA4 overexpression appears to be most efficient to achieve a general carotenoid increase in green leaves.

Figure 6:
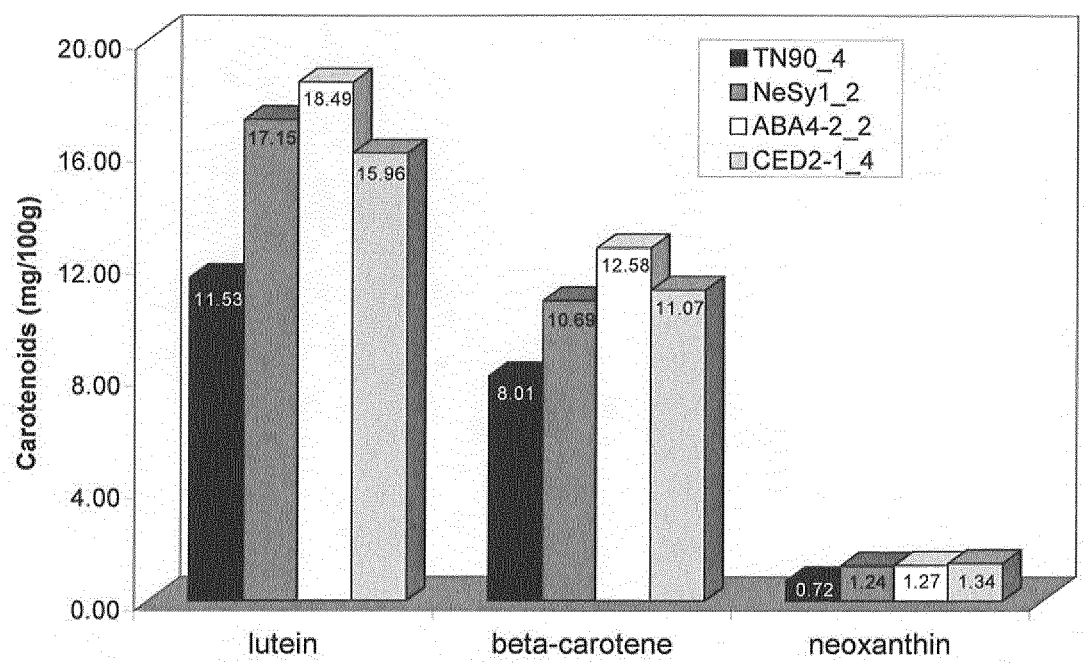
FIG. 6. Lutein, beta-carotene concentrations and semi-quantification of neoxanthin in 'green' samples (leaf pools) of TN90-4, 35S::NtNeSy-1_2 (NeSy1-2), 35S::NtABA4-2_2 (ABA4-2_2) and NtNCED2-interfering RNA-1_4 (CED2-1_4) selected lines.

Harvested leaf material is submitted to air-curing in order to confirm that the observed carotenoid changes result in altered amounts of beta-damascenone produced in the respective aerosol. In order to select the most promising cured samples, the sample/lines with the most drastic changes in lutein, beta-carotene and neoxanthin (semi-quantitative data) in green leaves are chosen. These sample/lines were NtNeSy-I_2, NtABA4-2_2 and NtNCED2-interfering RNA-I_4, respectively (FIG. 6). An assumption here is that neoxanthin or possibly other carotenoids which accumulate in green leaves are converted in cured leaves to beta-damascenone-glucoside or other beta-damascenone precursors, which are then released by heating.

Example 7

Beta-Damascenone Analysis in Selected Transgenic Lines

Figure 7:
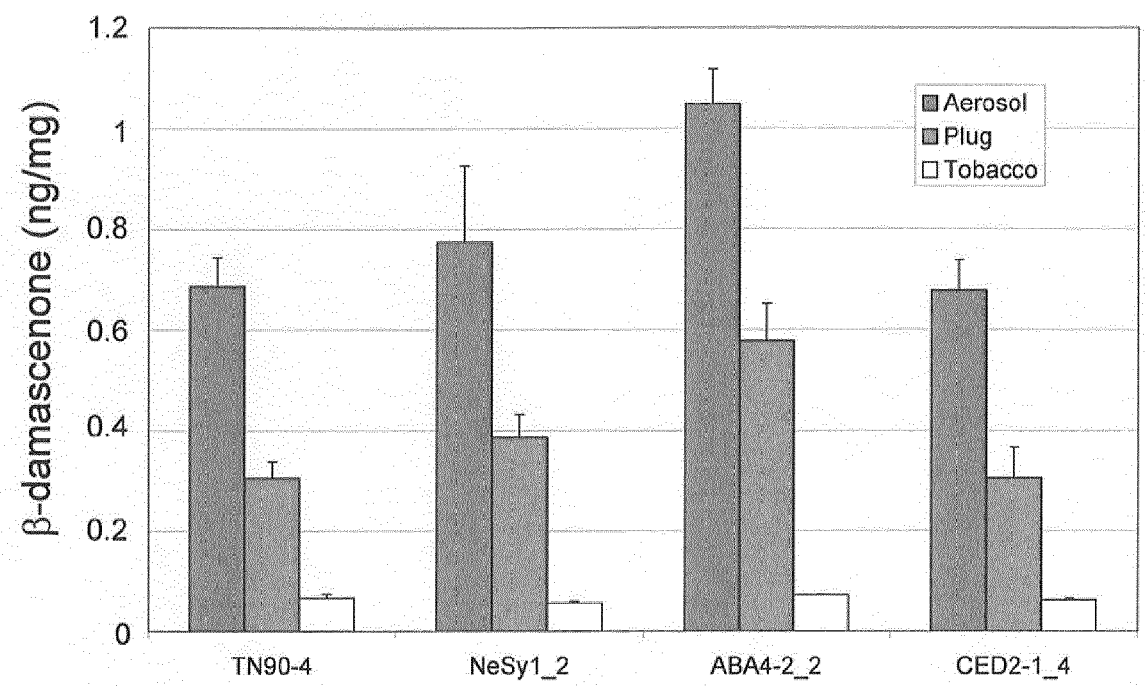
FIG. 7. Beta-damascenone content in the aerosol (Aerosol), cured tobacco (Tobacco) and tobacco plugs after aerosol formation (Plug) of the lines TN90-4 (TN90 control), 35S::NtNeSy-1_2 (NeSy1-2), 35S::NtABA4-2_2 (ABA4-2-2) and NtNCED2-interfering RNA-1_4 (CED2-1_4). Quantification of beta-damascenone is performed in triplicate, including smoke-simulator, aerosol trapping and beta-damascenone quantification. T-test analysis shows that the content of beta-damascenone in the aerosol of the line NtABA4-2_2 is statistically different from TN90-4 ($P<0.01$) and that the content of beta-damascenone in the plug of the line NtABA4-2_2 is statistically different from TN90-4 ($P<0.05$).

To analyze the content of beta-damascenone in the aerosol formed after heating the cured tobacco of TN90-4 (control), NtNeSy-I_2, NtABA4-2_2 and NtNCED2-interfering RNA-I_4 sample lines, aerosols from impregnated tobacco cut-filler are generated. The smoking platform used is a smoke-simulator with NHS heat source (54W) including a regime of 12 Puffs of 2 seconds each. Before smoking, tobacco cured lamina is cut and impregnated with 20% glycerin. The aerosols produced by heating impregnated cured tobaccos (100 mg, 3 full replicates) are trapped in Cambridge filter PAD. The PADs were introduced into a vial containing 10 mL water/EtOH (9/1, v/v). Beta-damascenone was extracted by the Stir Bar Sorbtive Extraction method (as described in Lancas et al. (2009) *J. Sep. Sci.* 32, 813-824). This method allows the extraction of chemical compounds which exhibit affinity for the adsorption phase. The stir bar is thermally desorbed in a GC-MS injector and analyzed for beta-damascenone. Compared to TN90 (control), the NtABA4-2_2 sample showed a 68% increase of beta-damascenone in the aerosol (FIG. 7). This difference is statistically relevant (P<0.01, T-test). These results suggest that the pool of precursor(s) for beta-damascenone in cured leaves is enhanced by NtABA4 ectopic expression while the effect of the two other target genes, NtNeSy (over-expression) and NtNCED2 (interfering RNA silencing), is resembling the TN90 control. Thus, overexpressing NtABA4 but not engineering NtNeSy or NtNCED in tobacco leaves likely leads to elevated production of beta-damascenone precursor(s).

Any publication cited or described herein provides relevant information disclosed prior to the filing date of the present application. Statements herein are not to be construed as an admission that the inventors are not entitled to antedate such disclosures. All publications mentioned in the above specification are herein incorporated by reference. Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in cellular, molecular and plant biology or related fields are intended to be within the scope of the following claims.

The invention claimed is:

1. A transgenic tobacco plant cell comprising:
   (i) a polynucleotide comprising or consisting of a sequence encoding a neoxanthin synthase and having at least 95% sequence identity to SEQ ID NO:1 or SEQ ID NO:6;
   (ii) a polypeptide encoded by the polynucleotide set forth in (i);
   (iii) a polypeptide having at least 95% sequence identity to SEQ ID NO:2 or at least 95% sequence identity to SEQ ID NO:7; or
   (iv) a construct, vector or expression vector comprising the polynucleotide set forth in (i), and
   wherein the expression or activity of the neoxanthin synthase is increased as compared to a control or wild type tobacco plant.

2. A transgenic tobacco plant comprising the tobacco plant cell according to claim 1.

3. A method for increasing the carotenoid content of a tobacco plant, comprising the steps of:
   (a) increasing the expression or activity of neoxanthin synthase in the tobacco plant by transforming the tobacco plant with a neoxanthin synthase, wherein the neoxanthin synthase comprises:
      (i) a polynucleotide comprising or consisting of a sequence encoding a neoxanthin synthase and having at least 95% sequence identity to SEQ ID NO:1 or SEQ ID NO:6;
      (ii) a polypeptide encoded by the polynucleotide set forth in (i); or
      (iii) a polypeptide having at least 95% sequence identity to SEQ ID NO:2 or at least 4095% sequence identity to SEQ ID NO:7;
   (b) measuring the carotenoid content in at least a part of a transgenic tobacco plant obtained in step (a); and
   (c) identifying a transgenic tobacco plant in which the carotenoid content therein has increased in comparison to a control tobacco plant in which the expression or activity of neoxanthin synthase has not been increased.

4. The method according to claim 3, wherein the expression or activity of lycopene beta cyclase is increased, or the expression or activity of 9-cis-epoxycarotenoid dioxygenase is decreased, or a combination thereof, in the tobacco plant.

5. The method according to claim 4, wherein the lycopene beta cyclase comprises the polynucleotide sequence set forth in SEQ ID NO:8 or has at least 90% sequence identity thereto or the polypeptide sequence comprises the set forth in SEQ ID NO:9 or has at least 95% sequence identity thereto and wherein the 9-cis-epoxycarotenoid dioxygenase comprises the polynucleotide sequence set forth in SEQ ID NO:13 or has at least 95% sequence identity thereto.

6. A method for increasing the beta-damascenone content in a tobacco plant, comprising the steps of:
   (a) increasing the expression or activity of neoxanthin synthase in the tobacco plant by transforming the tobacco plant with a neoxanthin synthase, wherein the neoxanthin synthase comprises:
      (i) a polynucleotide comprising or consisting of a sequence encoding a neoxanthin synthase and having at least 95% sequence identity to SEQ ID NO:1 or SEQ ID No. 6;
      (ii) a polypeptide encoded by the polynucleotide set forth in (i); or
      (iii) a polypeptide having at least 95% sequence identity to SEQ ID NO:2 or at least 95% sequence identity to SEQ ID No. 7;
   (b) measuring the beta-damascenone content in at least a part of a transgenic tobacco plant obtained in step (a) or an aerosol thereof; and
   (c) identifying a transgenic tobacco plant in which the beta-damascenone content has increased in comparison to a control tobacco plant in which the expression or activity of neoxanthin synthase has not been increased.

7. A transgenic tobacco plant or plant material derived or derivable therefrom that is obtained or obtainable by the method according to claim 6.

8. A transgenic tobacco plant, wherein expression of neoxanthin synthase or the activity of the protein encoded thereby has been increased; wherein the green leaf lutein content or the beta-carotene content or the combined lutein and beta-carotene content of the tobacco plant is higher than a control tobacco plant in which the expression or the activity of neoxanthin synthase has not been increased; and wherein the beta-damascenone content in aerosol of cured plant material is at least 10% higher than the aerosol from the control tobacco plant, preferably, wherein: (i) the green leaf lutein content of the plant is at least about 18 mg/100 g; (ii) wherein the beta-carotene content of the tobacco plant is at least about 12 mg/100 g; and (iii) wherein the beta-damascenone content in aerosol upon heating is at least about 1 ng/mg.

9. Plant material including biomass, seed or leaves from the tobacco plant of claim 2.

10. A tobacco product comprising the tobacco plant cell of claim 1.

11. A method for producing beta-damascenone comprising the steps of:
   (a) providing at least part of a tobacco plant according to claim 2; and
   (b) providing heat thereto to produce an aerosol comprising beta-damascenone.

12. Plant material including biomass, seed or leaves from the tobacco plant of claim 7.

13. Plant material including biomass, seed or leaves from the tobacco plant of claim 8.

14. A tobacco product comprising at least a part of the tobacco plant of claim 2.

15. A tobacco product comprising at least a part of the tobacco plant of claim 7.

16. A tobacco product comprising at least a part of the tobacco plant of claim 8.

17. A tobacco product comprising at least a part of the tobacco plant material according to claim 9.

18. A tobacco product comprising at least a part of the tobacco plant material according to claim 12.

19. A tobacco product comprising at least a part of the tobacco plant material according to claim 13.

20. A method for producing beta-damascenone comprising the steps of:
   (a) providing at least part of a tobacco plant according to claim 7; and
   (b) providing heat thereto to produce an aerosol comprising beta-damascenone.

21. A method for producing beta-damascenone comprising the steps of:
   (a) providing at least part of a tobacco plant according to claim 8; and
   (b) providing heat thereto to produce an aerosol comprising beta-damascenone.

22. A method for producing beta-damascenone comprising the steps of:
   (a) providing at least part of a tobacco plant material according to claim 9; and
   (b) providing heat thereto to produce an aerosol comprising beta-damascenone.

23. A method for producing beta-damascenone comprising the steps of:
   (a) providing at least part of a tobacco plant material according to claim 12; and
   (b) providing heat thereto to produce an aerosol comprising beta-damascenone.

24. A method for producing beta-damascenone comprising the steps of:
   (a) providing at least part of a tobacco plant material according to claim 13; and
   (b) providing heat thereto to produce an aerosol comprising beta-damascenone.

25. A method for producing beta-damascenone comprising the steps of:
   (a) providing at least part of the tobacco product according to claim 10; and
   (b) providing heat thereto to produce an aerosol comprising beta-damascenone.

26. A method for producing beta-damascenone comprising the steps of:
   (a) providing at least part of the tobacco product according to claim 14; and
   (b) providing heat thereto to produce an aerosol comprising beta-damascenone.

27. A method for producing beta-damascenone comprising the steps of:
   (a) providing at least part of the tobacco product according to claim 15; and
   (b) providing heat thereto to produce an aerosol comprising beta-damascenone.

28. A method for producing beta-damascenone comprising the steps of:
   (a) providing at least part of the tobacco product according to claim 16; and
   (b) providing heat thereto to produce an aerosol comprising beta-damascenone.

29. A method for producing beta-damascenone comprising the steps of:
   (a) providing at least part of the tobacco product according to claim 17; and
   (b) providing heat thereto to produce an aerosol comprising beta-damascenone.

30. A method for producing beta-damascenone comprising the steps of:
   (a) providing at least part of the tobacco product according to claim 18; and
   (b) providing heat thereto to produce an aerosol comprising beta-damascenone.

31. A method for producing beta-damascenone comprising the steps of:
   (a) providing at least part of the tobacco product according to claim 19; and
   (b) providing heat thereto to produce an aerosol comprising beta-damascenone.

* * * * *

SEQUENCE LISTING

<160> NUMBER OF SEQ ID NOS: 22

<210> SEQ ID NO 1
<211> LENGTH: 786
<212> TYPE: DNA
<213> ORGANISM: Nicotiana tabacum

<400> SEQUENCE: 1

```
atgtcacttt cttttaattc ttcttgtttt tgttcccctc ttaataagtc aagtatggac      60
ttctcttctt cttgcttctg ctactctcac atctcactca agatgaactg cagggcacct     120
gccttgatgt ccaggagaaa ccagcctacc tcttatactt ttctagaaaa gaattctgac     180
attgtaaatc aacaagtagt ggaattcgga accaagttta gaagtggagc gaatttcctg     240
ggaggatcaa gagtcattat tcaacttaat cttcaaacaa ctcttgctca aagaaaaagc     300
tccagggtga ctgcttgttt gccaagttct gaaattgctt ctactgtttt cacactggga     360
acagcagcag ttcttccgtt ttatactctc atggttgtgg ctcctaaaac tgaacttacc     420
agaaaagtga tgaaaagcag catacccaat attggctttg gacttctgta cacatatcta     480
gtatacctct cttggacacc agatacagtt cggctgatgt ttgctagtaa atactggctt     540
ccggagctgc ccggcataac taagatgttc tccaacgaga tgacattagc ttctgcatgg     600
attcacttgt tggctgtaga tcttttttgct gcaaggcagg tttatcatga tggattgcaa     660
aatgatattg aaacccgcca ttctgtgtct ctgtgcttgc tgttttgccc cgtcggaatt     720
gttactcact tcatccaccaa agctctagcc agtagcccag aaaagagaca gcataggact     780
cattaa                                                               786
```

<210> SEQ ID NO 2
<211> LENGTH: 261
<212> TYPE: PRT
<213> ORGANISM: Nicotiana tabacum

<400> SEQUENCE: 2

```
Met Ser Leu Ser Phe Asn Ser Ser Cys Phe Cys Ser Pro Leu Asn Lys
 1               5                  10                  15

Ser Ser Met Asp Phe Ser Ser Ser Cys Phe Cys Tyr Ser His Ile Ser
            20                  25                  30
```

-continued

```
Leu Lys Met Asn Cys Arg Ala Pro Ala Leu Met Ser Arg Arg Asn Gln
         35                  40                  45

Pro Thr Ser Tyr Thr Phe Leu Glu Lys Asn Ser Asp Ile Val Asn Gln
 50                  55                  60

Gln Val Val Glu Phe Gly Thr Lys Phe Arg Ser Gly Ala Asn Phe Leu
 65                  70                  75                  80

Gly Gly Ser Arg Val Ile Ile Gln Leu Asn Leu Gln Thr Thr Leu Ala
                 85                  90                  95

Gln Arg Lys Ser Ser Arg Val Thr Ala Cys Leu Pro Ser Ser Glu Ile
                100                 105                 110

Ala Ser Thr Val Phe Thr Leu Gly Thr Ala Ala Val Leu Pro Phe Tyr
                115                 120                 125

Thr Leu Met Val Val Ala Pro Lys Thr Glu Leu Thr Arg Lys Val Met
130                 135                 140

Lys Ser Ser Ile Pro Asn Ile Gly Phe Gly Leu Leu Tyr Thr Tyr Leu
145                 150                 155                 160

Val Tyr Leu Ser Trp Thr Pro Asp Thr Val Arg Leu Met Phe Ala Ser
                165                 170                 175

Lys Tyr Trp Leu Pro Glu Leu Pro Gly Ile Thr Lys Met Phe Ser Asn
                180                 185                 190

Glu Met Thr Leu Ala Ser Ala Trp Ile His Leu Leu Ala Val Asp Leu
                195                 200                 205

Phe Ala Ala Arg Gln Val Tyr His Asp Gly Leu Gln Asn Asp Ile Glu
                210                 215                 220

Thr Arg His Ser Val Ser Leu Cys Leu Leu Phe Cys Pro Val Gly Ile
225                 230                 235                 240

Val Thr His Phe Ile Thr Lys Ala Leu Ala Ser Ser Pro Glu Lys Arg
                245                 250                 255

Gln His Arg Thr His
                260

<210> SEQ ID NO 3
<211> LENGTH: 31
<212> TYPE: DNA
<213> ORGANISM: Artificial sequence
<220> FEATURE:
<221> NAME/KEY: source
<222> LOCATION: 1..31
<223> OTHER INFORMATION: /note= "Description of artificial sequence:
      Nucleotide sequence of forward primer used to amplify NtABA4 from
      Nicotiana tabacum K326 with the cacc sequence in the primer for
      cloning"

<400> SEQUENCE: 3
caccatgtca ctttctttta attcttcttg t                              31

<210> SEQ ID NO 4
<211> LENGTH: 27
<212> TYPE: DNA
<213> ORGANISM: Artificial sequence
<220> FEATURE:
<221> NAME/KEY: source
<222> LOCATION: 1..27
<223> OTHER INFORMATION: /note= "Description of artificial sequence:
      Nucleotide sequence of forward primer used to amplify NtABA4 from
      Nicotiana tabacum K326 without the cacc sequence in the primer for
      cloning"

<400> SEQUENCE: 4
atgtcacttt cttttaattc ttcttgt                                   27
```

<210> SEQ ID NO 5
<211> LENGTH: 27
<212> TYPE: DNA
<213> ORGANISM: Artificial sequence
<220> FEATURE:
<221> NAME/KEY: source
<222> LOCATION: 1..27
<223> OTHER INFORMATION: /note= "Description of artificial sequence:
      Nucleotide sequence of reverse primer used to amplify NtABA4 from
      Nicotiana tabacum K326"

<400> SEQUENCE: 5
ttaatgagtc ctatgctgtc tcttttc                                          27

<210> SEQ ID NO 6
<211> LENGTH: 789
<212> TYPE: DNA
<213> ORGANISM: Nicotiana tabacum

<400> SEQUENCE: 6
atgtcacttt cttttaattc ttcttcttgt ttttgttccc ctcttaataa gtcaagtatg      60
gacttctctt cttcttgctt ctgctactct cacatctcac tcaagatgaa ctgcagggca     120
cctgccttga tgtccaggag aaaccagcct acctcttata cttttctaga aaagaattct     180
gacattgtaa atcaacgagt agtggaattc agaaccaagt ttagaagtgg agcgaatttc     240
ctgggaggat caagagtcat tattcaactt aatcttcaaa caactcttgc tcaaagaaaa     300
agctccaggg tgactgcttg tttgccaagt tctgaaattg cttctactgt tttcacactg     360
ggaacagcag cggttcttcc gttttataca ctcatggtag tggctcctaa agctgaactt     420
accagaaaag tgatgaaaag cagcataccc tatattggct ttggacttct gtacacatat     480
ctagtatacc tctcttggac accagataca gttcggctga tgtttgctag taaatactgg     540
cttccggagc tgcccggcat aactaagatg ttctccaacg agatgacatt agcttctgca     600
tggattcact tgttggccgt agatcttttt gctgcaaggc aggtttatca tgatggattg     660
caaaatgata ttgaaacccg ccattctgtg tctctgtgct tgctgttttg ccccttcgga     720
attgttactc acttcatcac caaagctcta accagtagcc cagaaaagag acagcatagg     780
actcattaa                                                             789

<210> SEQ ID NO 7
<211> LENGTH: 262
<212> TYPE: PRT
<213> ORGANISM: Nicotiana tabacum

<400> SEQUENCE: 7

Met Ser Leu Ser Phe Asn Ser Ser Cys Phe Cys Ser Pro Leu Asn
1               5                   10                  15

Lys Ser Ser Met Asp Phe Ser Ser Ser Cys Phe Cys Tyr Ser His Ile
                20                  25                  30

Ser Leu Lys Met Asn Cys Arg Ala Pro Ala Leu Met Ser Arg Arg Asn
            35                  40                  45

Gln Pro Thr Ser Tyr Thr Phe Leu Glu Lys Asn Ser Asp Ile Val Asn
        50                  55                  60

Gln Arg Val Val Glu Phe Arg Thr Lys Phe Arg Ser Gly Ala Asn Phe
65                  70                  75                  80

Leu Gly Gly Ser Arg Val Ile Ile Gln Leu Asn Leu Gln Thr Thr Leu
                85                  90                  95

```
Ala Gln Arg Lys Ser Ser Arg Val Thr Ala Cys Leu Pro Ser Ser Glu
            100                 105                 110

Ile Ala Ser Thr Val Phe Thr Leu Gly Thr Ala Ala Val Leu Pro Phe
        115                 120                 125

Tyr Thr Leu Met Val Val Ala Pro Lys Ala Glu Leu Thr Arg Lys Val
    130                 135                 140

Met Lys Ser Ser Ile Pro Tyr Ile Gly Phe Gly Leu Leu Tyr Thr Tyr
145                 150                 155                 160

Leu Val Tyr Leu Ser Trp Thr Pro Asp Thr Val Arg Leu Met Phe Ala
                165                 170                 175

Ser Lys Tyr Trp Leu Pro Glu Leu Pro Gly Ile Thr Lys Met Phe Ser
            180                 185                 190

Asn Glu Met Thr Leu Ala Ser Ala Trp Ile His Leu Leu Ala Val Asp
        195                 200                 205

Leu Phe Ala Ala Arg Gln Val Tyr His Asp Gly Leu Gln Asn Asp Ile
    210                 215                 220

Glu Thr Arg His Ser Val Ser Leu Cys Leu Leu Phe Cys Pro Phe Gly
225                 230                 235                 240

Ile Val Thr His Phe Ile Thr Lys Ala Leu Thr Ser Ser Pro Glu Lys
                245                 250                 255

Arg Gln His Arg Thr His
            260
```

<210> SEQ ID NO 8
<211> LENGTH: 1482
<212> TYPE: DNA
<213> ORGANISM: Nicotiana tabacum

<400> SEQUENCE: 8

```
atggaaactc ttctcaaacc ttttccatct cctttacttt tcactcctac acctcacagg      60
tctattttc aactgaattc tacttttctg aatccaacca cccagaactt ttcaagaaaa     120
gttcatcgca gaaacaaaag tagtagtaac aaatttgta gctttcttga cttagcaccc     180
acatcaaaac cagagtcttt agatgttgac atctcatggg ttgatcctaa tcgggccgg     240
gctctattcg acgtgatcat catcggagct ggtcctgcgg gcctccggct agctgagcaa     300
gtatcaagat atggtattaa ggtatgttgt gttgacccctt caccactttc catgtggcca     360
aataattatg gtgtttgggt tgatgagttt gagaagttag gattgaaga ttgtttagat     420
cataagtggc ctatgacttg tgttcatata aatgataaca agactaagta tttgggaaga     480
ccatatggta gagtcagtag aaaaaagttg aagttgaaat tgttgaatag ttgtgttgat     540
aatggaggga gttttataa agccaaggtt tggaaagtgg agcatgaaga atttgagtct     600
tcagttgttt gtgatgatgg taggaagata aggggtagtt tgattgtaga tgcaagtggt     660
tttgctagtc cttttataga atatgacaag ccaagaaacc atggttatca aatagctcat     720
gggattttag cacaagtgga taatcatcca tttgatttgg ataaaatggt gcttatggat     780
tggagggatt ctcatctggg aaatgagcca tatttgaggg tgaacaatac taaagaacca     840
acattcttgt atgtgatgcc atttgatagg aattttggtat tcttggaaga gacttctttg     900
gtgagtcggc ctgtgctatc gtataggaa gtgaaaaata ggatggtgc aaggttaagg     960
catttgggga tcaaagtgac aagtgttatt gaggatgaga atgtgtgat ccccatggga    1020
ggaccacttc cgcggatccc tcaaaatgtt atggcaattg gtggaaattc agggatagtt    1080
catccatcga cagggtacat ggtggctcgg agcatggcat ggcaccagt tttggctgag    1140
```

```
gccattgctg agagcctcgg cacaaccaga atgataagag gatctccact ttaccataaa    1200
gtttggaatg gtttgtggcc tctagagaga agaagtgtga gagaatgtta ctcttttggg    1260
atggagactt tgttgaagct tgatttgaaa gggactagga gattgtttga tgctttcttt    1320
gatcttgatc ccaaatactg gcaagggttc ctttcctcaa ggttgtctgt caaagaactt    1380
gctatgctta gcttgtacct ttttgggcat gcctcaaatt tggctaggtt ggatattgtt    1440
acaaaatgcc cggtgccctt ggttaaaatg atggaaatct ag                      1482
```

<210> SEQ ID NO 9
<211> LENGTH: 493
<212> TYPE: PRT
<213> ORGANISM: Nicotiana tabacum

<400> SEQUENCE: 9

```
Met Glu Thr Leu Leu Lys Pro Phe Pro Ser Pro Leu Leu Phe Thr Pro
1               5                   10                  15

Thr Pro His Arg Ser Ile Phe Gln Leu Asn Ser Thr Phe Leu Asn Pro
            20                  25                  30

Thr Thr Gln Asn Phe Ser Arg Lys Val His Arg Arg Asn Lys Ser Ser
        35                  40                  45

Ser Asn Lys Phe Cys Ser Phe Leu Asp Leu Ala Pro Thr Ser Lys Pro
    50                  55                  60

Glu Ser Leu Asp Val Asp Ile Ser Trp Val Asp Pro Asn Ser Gly Arg
65                  70                  75                  80

Ala Leu Phe Asp Val Ile Ile Ile Gly Ala Gly Pro Ala Gly Leu Arg
                85                  90                  95

Leu Ala Glu Gln Val Ser Arg Tyr Gly Ile Lys Val Cys Cys Val Asp
            100                 105                 110

Pro Ser Pro Leu Ser Met Trp Pro Asn Asn Tyr Gly Val Trp Val Asp
        115                 120                 125

Glu Phe Glu Lys Leu Gly Leu Glu Asp Cys Leu Asp His Lys Trp Pro
    130                 135                 140

Met Thr Cys Val His Ile Asn Asp Asn Lys Thr Lys Tyr Leu Gly Arg
145                 150                 155                 160

Pro Tyr Gly Arg Val Ser Arg Lys Lys Leu Lys Leu Lys Leu Leu Asn
                165                 170                 175

Ser Cys Val Asp Asn Gly Gly Lys Phe Tyr Lys Ala Lys Val Trp Lys
            180                 185                 190

Val Glu His Glu Glu Phe Glu Ser Ser Val Val Cys Asp Asp Gly Arg
        195                 200                 205

Lys Ile Arg Gly Ser Leu Ile Val Asp Ala Ser Gly Phe Ala Ser Pro
    210                 215                 220

Phe Ile Glu Tyr Asp Lys Pro Arg Asn His Gly Tyr Gln Ile Ala His
225                 230                 235                 240

Gly Ile Leu Ala Gln Val Asp Asn His Pro Phe Asp Leu Asp Lys Met
                245                 250                 255

Val Leu Met Asp Trp Arg Asp Ser His Leu Gly Asn Glu Pro Tyr Leu
            260                 265                 270

Arg Val Asn Asn Thr Lys Glu Pro Thr Phe Leu Tyr Val Met Pro Phe
        275                 280                 285

Asp Arg Asn Leu Val Phe Leu Glu Glu Thr Ser Leu Val Ser Arg Pro
    290                 295                 300

Val Leu Ser Tyr Arg Glu Val Lys Asn Arg Met Val Ala Arg Leu Arg
305                 310                 315                 320
```

His Leu Gly Ile Lys Val Thr Ser Val Ile Glu Asp Glu Lys Cys Val
                325                 330                 335

Ile Pro Met Gly Gly Pro Leu Pro Arg Ile Pro Gln Asn Val Met Ala
            340                 345                 350

Ile Gly Gly Asn Ser Gly Ile Val His Pro Ser Thr Gly Tyr Met Val
        355                 360                 365

Ala Arg Ser Met Ala Leu Ala Pro Val Leu Ala Glu Ala Ile Ala Glu
    370                 375                 380

Ser Leu Gly Thr Thr Arg Met Ile Arg Gly Ser Pro Leu Tyr His Lys
385                 390                 395                 400

Val Trp Asn Gly Leu Trp Pro Leu Glu Arg Arg Ser Val Arg Glu Cys
                405                 410                 415

Tyr Ser Phe Gly Met Glu Thr Leu Leu Lys Leu Asp Leu Lys Gly Thr
            420                 425                 430

Arg Arg Leu Phe Asp Ala Phe Phe Asp Leu Asp Pro Lys Tyr Trp Gln
        435                 440                 445

Gly Phe Leu Ser Ser Arg Leu Ser Val Lys Glu Leu Ala Met Leu Ser
    450                 455                 460

Leu Tyr Leu Phe Gly His Ala Ser Asn Leu Ala Arg Leu Asp Ile Val
465                 470                 475                 480

Thr Lys Cys Pro Val Pro Leu Val Lys Met Met Glu Ile
                485                 490

<210> SEQ ID NO 10
<211> LENGTH: 29
<212> TYPE: DNA
<213> ORGANISM: Artificial sequence
<220> FEATURE:
<221> NAME/KEY: source
<222> LOCATION: 1..29
<223> OTHER INFORMATION: /note= "Description of artificial sequence:
      Nucleotide sequence of forward primer used to amplify NeSy from
      Nicotiana tabacum K326 with the cacc sequence in the primer for
      cloning"

<400> SEQUENCE: 10
caccatggaa actcttctca aaccttttc                                      29

<210> SEQ ID NO 11
<211> LENGTH: 25
<212> TYPE: DNA
<213> ORGANISM: Artificial sequence
<220> FEATURE:
<221> NAME/KEY: source
<222> LOCATION: 1..25
<223> OTHER INFORMATION: /note= "Description of artificial sequence:
      Nucleotide sequence of forward primer used to amplify NeSy from
      Nicotiana tabacum K326 without the cacc sequence in the primer for
      cloning"

<400> SEQUENCE: 11
atggaaactc ttctcaaacc ttttc                                          25

<210> SEQ ID NO 12
<211> LENGTH: 25
<212> TYPE: DNA
<213> ORGANISM: Artificial sequence
<220> FEATURE:
<221> NAME/KEY: source
<222> LOCATION: 1..25
<223> OTHER INFORMATION: /note= "Description of artificial sequence:
      Nucleotide sequence of reverse primer used to amplify NeSy from
      Nicotiana tabacum K326"

```
<400> SEQUENCE: 12
ctagatttcc atcattttaa ccaag                                          25

<210> SEQ ID NO 13
<211> LENGTH: 407
<212> TYPE: DNA
<213> ORGANISM: Nicotiana tabacum

<400> SEQUENCE: 13
acacaagctt ggctttattc ggaggcaaac tattcgctct tggtgaatct gatttaccgt    60
atgcagtaaa attagcccca gatggtgata ttattaccct cggccgttac gatttcgacg   120
gaaaactttt catgagcatg acggcacatc ccaaaattga cccagatact aacgaggctt   180
ttgctttccg ttacggtcca atgcctcctt ttttaactta ctttagaatc gaaccaaatg   240
gtacaaaaac accagacgtg ccaatatttt ctatgacacg tccgtcattt cttcatgact   300
ttgcaattac aaataaattt gcgatattct cggacataca aataggaatg aacccacttg   360
agttcatcac cggtggttca ccggtgagtt cagactcggg gaaaatc                 407

<210> SEQ ID NO 14
<211> LENGTH: 25
<212> TYPE: DNA
<213> ORGANISM: Artificial sequence
<220> FEATURE:
<221> NAME/KEY: source
<222> LOCATION: 1..25
<223> OTHER INFORMATION: /note= "Description of artificial sequence:
      Nucleotide sequence of forward primer used to amplify NCED2 from
      Nicotiana tabacum with the cacc sequence in the primer for
      cloning"

<400> SEQUENCE: 14
caccacacaa gcttggcttt attcg                                          25

<210> SEQ ID NO 15
<211> LENGTH: 21
<212> TYPE: DNA
<213> ORGANISM: Artificial sequence
<220> FEATURE:
<221> NAME/KEY: source
<222> LOCATION: 1..21
<223> OTHER INFORMATION: /note= "Description of artificial sequence:
      Nucleotide sequence of forward primer used to amplify NCED2 from
      Nicotiana tabacum without the cacc sequence in the primer for
      cloning"

<400> SEQUENCE: 15
acacaagctt ggctttattc g                                              21

<210> SEQ ID NO 16
<211> LENGTH: 21
<212> TYPE: DNA
<213> ORGANISM: Artificial sequence
<220> FEATURE:
<221> NAME/KEY: source
<222> LOCATION: 1..21
<223> OTHER INFORMATION: /note= "Description of artificial sequence:
      Nucleotide sequence of reverse primer used to amplify NCED2 from
      Nicotiana tabacum"

<400> SEQUENCE: 16
gattttcccc gagtctgaac t                                              21

<210> SEQ ID NO 17
```

<211> LENGTH: 22
<212> TYPE: DNA
<213> ORGANISM: Cauliflower mosaic virus

<400> SEQUENCE: 17
gagcatcgtg gaaaaagaag ac                                            22

<210> SEQ ID NO 18
<211> LENGTH: 107
<212> TYPE: DNA
<213> ORGANISM: Nicotiana tabacum

<400> SEQUENCE: 18
atgtcacttt cttttaattc ttcttcttgt ttttgttccc ctcttaataa gtcaagtatg    60
gacttctctt cttcttgctt ctgctactct cacatctcac tcaaggt                 107

<210> SEQ ID NO 19
<211> LENGTH: 319
<212> TYPE: DNA
<213> ORGANISM: Nicotiana tabacum

<400> SEQUENCE: 19
agatgaactg cagggcacct gccttgatgt ccaggagaaa ccagcctacc tcttatactt    60
ttctagaaaa gaattctgac attgtaaatc aacgagtagt ggaattcaga accaagttta   120
gaagtggagc gaatttcctg ggaggatcaa gagtcattat tcaacttaat cttcaaacaa   180
ctcttgctca agaaaaagc tccagggtga ctgcttgttt gccaagttct gaaattgctt    240
ctactgtttt cacactggga acagcagcgg ttcttccgtt ttatacactc atggtagtgg   300
ctcctaaagc tgaacttgt                                               319

<210> SEQ ID NO 20
<211> LENGTH: 133
<212> TYPE: DNA
<213> ORGANISM: Nicotiana tabacum

<400> SEQUENCE: 20
agaccagaaa agtgatgaaa agcagcatac cctatattgg ctttggactt ctgtacacat    60
atctagtata cctctcttgg acaccagata cagttcggct gatgtttgct agtaaatact   120
ggcttccgga ggt                                                     133

<210> SEQ ID NO 21
<211> LENGTH: 93
<212> TYPE: DNA
<213> ORGANISM: Nicotiana tabacum

<400> SEQUENCE: 21
agctgcccgg cataactaag atgttctcca acgagatgac attagcttct gcatggattc    60
acttgttggc cgtagatctt tttgctgcaa ggt                                93

<210> SEQ ID NO 22
<211> LENGTH: 153
<212> TYPE: DNA
<213> ORGANISM: Nicotiana tabacum -continued

```
<400> SEQUENCE: 22
aggcaggttt atcatgatgg attgcaaaat gatattgaaa cccgccattc tgtgtctctg    60
tgcttgctgt tttgcccctt cggaattgtt actcacttca tcaccaaagc tctaaccagt   120
agcccagaaa agagacagca taggactcat taa                                153
```